US012760354B2

(12) United States Patent
Thrippleton

(10) Patent No.: US 12,760,354 B2
(45) Date of Patent: Oct. 13, 2026

(54) IN-SITU CONCATENATION OF OLIGO-NUCLEOTIDE PROBES FOR TARGET DETECTION

(71) Applicant: QBIOTIX LIMITED, Ledbury (GB)

(72) Inventor: Ian Thrippleton, Ledbury (GB)

(73) Assignee: QBIOTIX LIMITED, Ledbury (GB)

( * ) Notice: Subject to any disclaimer, the term of this patent is extended or adjusted under 35 U.S.C. 154(b) by 1025 days.

(21) Appl. No.: 17/618,384

(22) PCT Filed: Jun. 15, 2020

(86) PCT No.: PCT/GB2020/051444
§ 371 (c)(1),
(2) Date: Dec. 10, 2021

(87) PCT Pub. No.: WO2020/249982
PCT Pub. Date: Dec. 17, 2020

(65) Prior Publication Data

US 2022/0315994 A1 Oct. 6, 2022

(30) Foreign Application Priority Data

Jun. 13, 2019 (GB) ..................................... 1908481

(51) Int. Cl.
*C12Q 1/6818* (2018.01)

(52) U.S. Cl.
CPC .................................. *C12Q 1/6818* (2013.01)

(58) Field of Classification Search
CPC ............ C12Q 1/6818; C12Q 2525/161; C12Q 2525/301; C12Q 2527/107; C12Q 2543/10; C12Q 2565/101
See application file for complete search history.

(56) References Cited

U.S. PATENT DOCUMENTS 6,472,156 B1 10/2002 Wittwer et al.
2005/0287548 A1 12/2005 Bao et al.
2014/0194316 A1 7/2014 Thrippleton et al.
2014/0255924 A1* 9/2014 Sampas ................ C12Q 1/6818 436/501
2016/0289747 A1 10/2016 Eboigbodin et al.

FOREIGN PATENT DOCUMENTS

GB 2378245 A 2/2003
WO 2005/090608 A2 9/2005

OTHER PUBLICATIONS

International Search Report and Written Opinion in corresponding PCT application No. PCT/GB2020/051444 dated Jul. 8, 2020.
Guo et al. Fluorescent hybridization probes for nucleic acid detection. Analytical and Bioanalytical Chemistry, vol. 402, pp. 3115-3125. 2012.
Jockusch et al. Spectroscopic investigation of a FRET molecular beacon containing two fluorophores for probing DNA/RNA sequences. Photochemical and Photobiological Sciences, vol. 5, pp. 493-498. 2006.
Zhang et al. Design of a Molecular Beacon DNA Probe with Two Fluorophores. Angewandte Chemie International Edition, vol. 40, pp. 402-405. 2001.

* cited by examiner

*Primary Examiner* — Anne M. Gussow
*Assistant Examiner* — Allison E Schloop
(74) *Attorney, Agent, or Firm* — Day Pitney LLP; Christopher R. Cowles; Jacob J. Golan

(57) ABSTRACT

The present invention relates to a multiplicity of nucleic acid probes, a composition comprising said probes and uses thereof. The invention relates to a multiplicity of non-beacon, hairpin loop forming nucleic acid probes. In particular, the invention relates to a multiplicity of nucleic acid probes, each nucleic acid probe comprising a nucleic acid sequence complementary to the target nucleic acid sequence; wherein said nucleic acid probes are capable of forming a multimer in-situ with at least a neighbouring probe. The invention relates to the use of nucleic acid probes to detect the presence or absence of organisms in biological samples.

7 Claims, 45 Drawing Sheets

Specification includes a Sequence Listing.

Determination of target overlaps:

| | 3 (a / b) | 4 (a / b) | 5 (a / b) |
|---|---|---|---|
| DNA Target sequence (3 to 10) | ta gta taa aag cag aca/ ttt tat gca cca aaa ga | g aac tgc aat gtt tca/ gga ccc aca gga | gcg acc cag aaa/gtt acc aca gtt atg c |
| Probe sequences (3 to 9) | *tc ttt tgg tgc ata aaa tgt ctg ctt tta tac ta* | *tcc tgt ggg tcc tga aac att gca gtt c* | *tg cat aac tgt ggt aac ttt ctg ggt cgc* |
| Total free energy per target | 3: ΔG = - 25.0 ΔH = - 260.3 ΔS = -728.1 Tm = 61.4°C | 4: ΔG = -25.2 ΔH = -205.4 ΔS = -557.5 Tm = 65.0°C | 5: ΔG = -24.9 ΔH = -227.9 ΔS = -628.2 Tm = 62.9°C |
| Half targets b | 3b: ttt tat gca cca aaa ga | 4b: gga ccc aca gga | 5b: gtt acc aca gtt atg c |
| Half probes b | 3b': tc ttt tgg tgc ataaaa | 4b': tcc tgt ggg tcc | 5b' g cat aac tgt ggt aac |
| Two-state folding data in kcal/mol: | 3b: ΔG = - 11.7 ΔH = -125.0 ΔS = -350.8 Tm = 38.8°C | 4b: ΔG = -10.9 ΔH = -87.7 ΔS = -237.8 Tm = 31.7°C | 5b: ΔG = -11.3 ΔH = -121.9 ΔS = -342.2 Tm = 37.8°C |
| Half targets a | 3a: ta gta taa aag cag aca | 4a: g aac tgc aat gtt tca | 5a: gcg acc cag aaa |
| Half probes a | 3a': tgt ctg ctt tta tac ta | 4a': tga aac att gca gtt c | 5a': ttt ctg ggt cgc |
| Hybridisation of halfs | 3a: ΔG = -10.9 ΔH = -123.5 ΔS = -348.4 Tm = 36.9°C | 4a: ΔG = -11.5 ΔH = -107.5 ΔS = -297.1 Tm = 36.7°C | 5a: ΔG = -10.3 ΔH = -90.9 ΔS = -249.4 Tm = 30.6°C |
| | delta ΔG = 3-(3a+3b) = -3.4 kcal/mol | delta ΔG = 4-(4a+4b) = -2.8 kcal/mol | delta ΔG = 5-(5b+5a) = -3.3 kcal/mol |

A

1

FIG. 2

| 6 | 7 | 8 | 9 | 10 |
|---|---|---|---|---|
| a … b | a … b | a … b | a … b | a |
| ac aga gct gca aac/aac tat aca tga tat aat att | aga atg tgt gta ctg/caa gca aca gtt act g | cg acg tga ggt ata/ tga ctt tgc tt ttc g | gg att tat gca tagt ata/ tag aga tgg gaa tcc at | a tgc tgt atg tga taa atg |
| *aat att ata tca tgt ata gtt gtt tgc agc tct gt* | *c agt aac tgt tgc ttg cag tac aca cat tc* | *c gaa aa gca aag tca/ tat acc tca cgt cg* | *at gga ttc cca tct cta / tat acta tgc ata aat cc* | cat tta tcacat aca gca t |
| 6: ΔG = -24.3 ΔH = -254.9 ΔS = -713.6 Tm = 60.7°C | 7: ΔG = -25.0 ΔH = -242.5 ΔS = -673.0 Tm = 62.3°C | 8: ΔG = -24.0 ΔH = -233.0 ΔS = -646.8 Tm = 61.3°C | 9: ΔG = -24.5 ΔH = -263.5 ΔS = -739.6 Tm = 60.6°C | |
| 6b: aac tat aca tga tat aat att | 7b: caa gca aca gtt act g | 8b: tga ctt tgc tt ttc g | 9b: tag aga tgg gaa tcc at | a tgc tgt atg tga taa at |
| 6b': aat att ata tca tgt ata gtt | 7b': c agt aac tgt tgc ttg | 8b': c gaa aa gca aag tca | 9b' at gga ttc cca tct cta | |
| 6b: ΔG = -10.2 ΔH = -144.0 ΔS = -414.1 Tm = 37.2°C | 7b: ΔG = -11.6 ΔH = -123.1 ΔS = -345.2 Tm = 38.5°C | 8b: ΔG = -11.1 ΔH = -114.9 ΔS = -321.3 Tm = 36.4°C | 9b: ΔG = -12.7 ΔH = -121.9 ΔS = -338.0 Tm = 41.1°C | |
| 6a: ac aga gct gca aac | 7a: aga atg tgt gta ctg | 8a: cg acg tga ggt ata | 9a: gg att tat gca tagt ata | |
| 6a': gtt tgc agc tct gt | 7a': cag tac aca cat tc | 8a': tat acc tca cgt cg | 9a': tat acta tgc ata aat cc | |
| 6a: ΔG = -11.5 ΔH = -106.9 ΔS = -295.3 Tm = 36.5°C | 7a: ΔG = -10.1 ΔH = -111.3 ΔS = -313.0 Tm = 33.5°C | 8a: ΔG = -11.1 ΔH = -106.7 ΔS = -295.9 Tm = 35.4°C | 9a: ΔG = -10.6 ΔH = -130.6 ΔS = -371.3 Tm = 36.9°C | |
| delta ΔG = 6-(6b+6a) = - 2.6 kcal/mol | delta ΔG = 7-(7a+7b) = - 3.4 kcal/mol | delta ΔG = 8-(8b+8a) = - 1.6 kcal/mol | delta ΔG = 9-(9a+9b) = - 1.2 kcal/mol | |

(A) (2)

FIG. 2 (cont.)

| | | | |
|---|---|---|---|
| | 3b+4a | 4b+5a | 5b+6a |
| resultinng cDNA Targets: | ttt tat gca cca aaa ga + g aac tgc aat gtt tca | gga ccc aca gga + gcg acc cag aaa | gtt acc aca gtt atg c + ac aga gct gca aac |
| | 7' | 6' | 5' |
| esulting cDNA Probes: | tga aac att gca gtt c tc ttt tgg tgc ata aaa | ttt ctg ggt cgc tcc tgt ggg tcc | gtt tgc agc tct gt g cat aac |
| Two-state folding data in kcal/mol: | ΔG = -25.8 ΔH = -256.3 ΔS = -713.4 Tm = 62.6°C | ΔG = -23.8 ΔH = -188.7 ΔS = -510.3 Tm = 63.7°C | ΔG = -25.8 ΔH = -239.7 ΔS = -661.9 Tm = 63.6°C |
| | 2015-06-30-A-B 1.png | 2015-06-30-A-B 2.png | 2015-06-30-A-B 3.png |
| resulting cDNA Probes with helper: starting with 1' and 3' as "anti" sequence and 5' complementary to respective 3' sequence | accctg tga aac att gca gtt c tc ttt tgg tgc ata aaa | tttgaggg ttt ctg ggt cgc tcc tgt ggg tcc cagggt | ggatgt gtt tgcagc tct gt g cat aac tgt ggt aac |
| | ΔG = -4.3 ΔH = -47.1 ΔS = -132.5 Tm = -14.9°C | ΔG = -5.3 ΔH = -62.7 ΔS = -177.6 Tm = 2.5°C | ΔG = -4.5 ΔH = -47.6 ΔS = -133.4 Tm = -13.4°C |
| | 2015-07-11-A-B 6.png | 2015-07-11-A-B 5.png | 2015-07-11-A-B 4.png |
| Two-state folding data in kcal/mol: | ΔG = -0.4 ΔH = -26.1 ΔS = -82.0 Tm = 45.2°C | ΔG = -1.3 ΔH = -46.3 ΔS = -139.2 Tm = 59.6°C | ΔG = -0.1 ΔH = -26.1 ΔS = -80.4 Tm = 51.6°C |
| | 2015-07-11-A 13.png | 2015-07-11-A 11.png | 2015-07-11-A 10.png |

FIG. 2 (cont.)

| 6b+7a | 7b+8a | 8b+9a | 9b+10a |
|---|---|---|---|
| aac tat aca tga tat<br>aat att + aga atg<br>tgt gta ctg | caa gca aca gtt<br>act g + cg acg<br>tga ggt ata | tga ctt tgc tt ttc<br>g + gg att tat<br>gca tagt ata | tag aga tgg gaa<br>tcc at + a tgc tgt<br>atg tga taa at |
| 4' | 3' | 2' | 1' |
| cag tac aca cat tct aat<br>att ata tca tgt ata gtt | tat acc tca cgt cg c<br>agt aac tgt tgc ttg | tat acta tgc ata aat cc<br>cgaa aa gca aag tca | at tta tca cat aca gca t<br>at gga ttc cca tct cta |
| ΔG = -22.1 ΔH =<br>-260.2 ΔS = -736.9<br>Tm = 57.6°C | ΔG = -26.5 ΔH =<br>-239.8 ΔS = -660.1<br>Tm = 64.6°C | ΔG = -25.2 ΔH =<br>-253.7 ΔS = -707.2<br>Tm = 62.0°C | ΔG = -26.1 ΔH =<br>-264.7 ΔS = -738.4<br>Tm = 62.7°C |
| 2015-06-30-A-B 4.png | 2015-06-30-A-B 5.png | 2015-06-30-A-B 6.png | 2015-06-30-A-B 7.png |
| cgtca cag tac aca<br>cat tct aat att ata<br>tca tgt ata gtt | cgcg tat acc tca<br>cgt cg c agt aac<br>tgt tgc ttg tgacg | acgcg tat acta tgc<br>ata aat cc cgaa aa<br>gca aag tca | at tta tca cat aca<br>gca t at gga ttc<br>cca tct cta cgc gt |
| ΔG = -4.7 ΔH =<br>-50.4 ΔS = -141.3<br>Tm = -9.6°C | ΔG = -5.0 ΔH = -37.1<br>ΔS = -99.2 Tm =<br>-24.4°C | ΔG = -5.8 ΔH =<br>-42.2 ΔS = -112.5<br>Tm = -13.3°C | |
| 2015-07-11-A-B 3.png | 2015-07-11-A-B 2.png | 2015-07-11-A-B 1.png | |
| ΔG = -1.1 ΔH =<br>-23.4 ΔS = -75.9 Tm<br>= 35.0°C | ΔG = -2.3 ΔH = -2.3<br>ΔS = -14.3 Tm =<br>-112.9°C | ΔG = -3.9 ΔH = -85.1<br>ΔS = -251.4 Tm =<br>65.4°C | |
| 2015-07-11-A 9.png | 2015-07-11-A 8.png | 2015-07-11-A 7.png | |

FIG. 2 (cont.)

Probe Staaur
G CAA GCT TCT CGT CCG TTC GC
Target GC GAA CGG ACG AGA AGC TTG C

| Select for downloading or viewing reports | Description | Max score | Total score | Query cover | E value | Ident | Accession |
|---|---|---|---|---|---|---|---|
| Select seq AP018376.1 | Staphylococcus aureus SA003 DNA, nearly complete genome | 42.1 | 168 | 100% | **0.049** | 100% | AP018376.1 |
| Select seq MG976635.1 | Staphylococcus aureus strain J1 16S ribosomal RNA gene, partial sequence | 42.1 | 42.1 | 100% | **0.049** | 100% | MG976635.1 |
| Select seq MG976629.1 | Staphylococcus aureus strain S4 16S ribosomal RNA gene, partial sequence | 42.1 | 42.1 | 100% | **0.049** | 100% | MG976629.1 |
| Select seq MG971399.1 | Staphylococcus aureus strain NBRC 100910 16S ribosomal RNA gene, partial sequence | 42.1 | 42.1 | 100% | **0.049** | 100% | MG971399.1 |
| Select seq MG971398.1 | Staphylococcus aureus strain NBRC 100910 16S ribosomal RNA gene, partial sequence | 42.1 | 42.1 | 100% | **0.049** | 100% | MG971398.1 |
| Select seq CP012119.2 | Staphylococcus aureus subsp. aureus strain USA300 2014.C01 chromosome, complete genome | 42.1 | 252 | 100% | **0.049** | 100% | CP012119.2 |
| Select seq MG966418.1 | Staphylococcus aureus strain AS2 16S ribosomal RNA gene, partial sequence | 42.1 | 42.1 | 100% | **0.049** | 100% | MG966418.1 |
| Select seq CP026968.1 | Staphylococcus aureus strain FDAARGOS 1 chromosome, complete genome | 42.1 | 294 | 100% | **0.049** | 100% | CP026968.1 |
| Select seq CP026964.1 | Staphylococcus aureus strain FDAARGOS 2 chromosome, complete genome | 42.1 | 252 | 100% | **0.049** | 100% | CP026964.1 |
| Select seq CP026962.1 | Staphylococcus aureus strain FDAARGOS 6 chromosome, complete genome | 42.1 | 252 | 100% | **0.049** | 100% | CP026962.1 |
| Select seq CP026961.1 | Staphylococcus aureus strain FDAARGOS 10 chromosome, complete genome | 42.1 | 252 | 100% | **0.049** | 100% | CP026961.1 |
| Select seq CP026960.1 | Staphylococcus aureus strain FDAARGOS 15 chromosome, complete genome | 42.1 | 252 | 100% | **0.049** | 100% | CP026960.1 |
| Select seq CP026958.1 | Staphylococcus aureus strain FDAARGOS 40 chromosome, complete genome | 42.1 | 210 | 100% | **0.049** | 100% | CP026958.1 |

FIG. 4a-1

Probe Staaur
G CAA GCT TCT CGT CCG TTC GC
Target GC GAA CGG ACG AGA AGC TTG C

| Select for downloading or viewing reports | Description | Max score | Total score | Query cover | E value | Ident | Accession |
|---|---|---|---|---|---|---|---|
| Select seq CP026957.1 | Staphylococcus aureus strain FDAARGOS 43 chromosome, complete genome | 42.1 | 252 | 100% | **0.049** | 100% | CP026957.1 |
| Select seq CP026953.1 | Staphylococcus aureus strain FDAARGOS 48 chromosome, complete genome | 42.1 | 244 | 100% | **0.049** | 100% | CP026953.1 |
| Select seq CP016858.2 | Staphylococcus aureus subsp. aureus strain 1971.C01 chromosome, complete genome | 42.1 | 210 | 100% | **0.049** | 100% | CP016858.2 |
| Select seq CP016855.2 | Staphylococcus aureus subsp. aureus strain 5118.N chromosome, complete genome | 42.1 | 252 | 100% | **0.049** | 100% | CP016855.2 |
| Select seq CP007539.3 | Staphylococcus aureus subsp. aureus strain FDAARGOS 5 chromosome, complete genome | 42.1 | 252 | 100% | **0.049** | 100% | CP007539.3 |
| Select seq CP014064.2 | Staphylococcus aureus strain FDAARGOS 159 chromosome, complete genome | 42.1 | 244 | 100% | **0.049** | 100% | CP014064.2 |
| Select seq MG871238.1 | Staphylococcus aureus strain FC1388 16S ribosomal RNA gene, partial sequence | 42.1 | 42.1 | 100% | **0.049** | 100% | MG871238.1 |
| Select seq CP020656.1 | Staphylococcus aureus strain K5 chromosome, complete genome | 42.1 | 42.1 | 100% | **0.049** | 100% | CP020656.1 |
| Select seq CP026080.1 | Staphylococcus aureus strain NRS137 chromosome, complete genome | 42.1 | 252 | 100% | **0.049** | 100% | CP026080.1 |
| Select seq CP026077.1 | Staphylococcus aureus strain NRS107 chromosome, complete genome | 42.1 | 252 | 100% | **0.049** | 100% | CP026077.1 |
| Select seq CP026074.1 | Staphylococcus aureus strain HPV107 chromosome, complete genome | 42.1 | 244 | 100% | **0.049** | 100% | CP026077.1 |
| Select seq CP026064.1 | Staphylococcus aureus strain NRS271 chromosome, complete genome | 42.1 | 202 | 100% | **0.049** | 100% | CP026064.1 |
| Select seq CP026079.1 | Staphylococcus aureus strain NRS70 chromosome, complete genome | 42.1 | 202 | 100% | **0.049** | 100% | CP026079.1 |

FIG. 4a-2

Probe Staaur
G CAA GCT TCT CGT CCG TTC GC
Target GC GAA CGG ACG AGA AGC TTG C

| **Select for downloading or viewing reports** | **Description** | Max score | Total score | Query cover | **E value** | Ident | **Accession** |
|---|---|---|---|---|---|---|---|
| Select seq CP026076.1 | Staphylococcus aureus strain TCH 959 chromosome, complete genome | 42.1 | 252 | 100% | **0.049** | 100% | CP026076.1 |
| Select seq CP026073.1 | Staphylococcus aureus strain Mw2 chromosome, complete genome | 42.1 | 252 | 100% | **0.049** | 100% | CP026073.1 |
| Select seq CP026072.1 | Staphylococcus aureus strain NRS120 chromosome, complete genome | 42.1 | 202 | 100% | **0.049** | 100% | CP026072.1 |
| Select seq CP026071.1 | Staphylococcus aureus strain NRS143 chromosome, complete genome | 42.1 | 252 | 100% | **0.049** | 100% | CP026071.1 |
| Select seq CP026070.1 | Staphylococcus aureus strain NRS133 chromosome, complete genome | 42.1 | 252 | 100% | **0.049** | 100% | CP026070.1 |
| Select seq CP026069.1 | Staphylococcus aureus strain NRS1 chromosome, complete genome | 42.1 | 202 | 100% | **0.049** | 100% | CP026069.1 |
| Select seq CP026068.1 | Staphylococcus aureus strain NRS146 chromosome, complete genome | 42.1 | 252 | 100% | **0.049** | 100% | CP026068.1 |
| Select seq CP026067.1 | Staphylococcus aureus strain NRS153 chromosome, complete genome | 42.1 | 252 | 100% | **0.049** | 100% | CP026067.1 |
| Select seq CP026066.1 | Staphylococcus aureus strain NRS484 chromosome, complete genome | 42.1 | 252 | 100% | **0.049** | 100% | CP026066.1 |
| Select seq CP026063.1 | Staphylococcus aureus strain NRS149 chromosome, complete genome | 42.1 | 244 | 100% | **0.049** | 100% | CP026063 1 |
| Select seq MG818959.1 | Staphylococcus aureus strain FA-1 16S ribosomal RNA gene, partial sequence | 42.1 | 42.1 | 100% | **0.049** | 100% | MG818959 1 |
| Select seq CP018629.1 | Staphylococcus aureus strain MRSA107 chromosome, complete genome | 42.1 | 210 | 100% | **0.049** | 100% | CP018629.1 |
| Select seq MG757682.1 | Staphylococcus aureus strain ZS-35C 16S ribosomal RNA gene, partial sequence | 42.1 | 42.1 | 100% | **0.049** | 100% | MG757682.1 |

FIG. 4a-3

Probe Staaur
G CAA GCT TCT CGT CCG TTC GC
Target GC GAA CGG ACG AGA AGC TTG C

| **Select for downloading or viewing reports** | **Description** | Max score | Total score | Query cover | **E value** | Ident | **Accession** |
|---|---|---|---|---|---|---|---|
| Select seq MG757681.1 | Staphylococcus aureus strain ZS-28C 16S ribosomal RNA gene, partial sequence | 42.1 | 42.1 | 100% | **0.049** | 100% | MG757681.1 |
| Select seq CP016856.2 | Staphylococcus aureus subsp. aureus strain 2148.N chromosome, complete genome | 42.1 | 244 | 100% | **0.049** | 100% | CP016856.2 |
| Select seq P012120.2 | Staphylococcus aureus subsp. aureus strain USA300 2014. C02 chromosome, complete genome | 42.1 | 252 | 100% | **0.049** | 100% | CP012120.2 |
| Select seq P017094.2 | Staphylococcus aureus subsp. aureus strain 2148.C01 chromosome, complete genome | 42.1 | 252 | 100% | **0.049** | 100% | CP017094.2 |
| Select seq P016861.2 | Staphylococcus aureus subsp. aureus strain 1969.N chromosome, complete genome | 42.1 | 252 | 100% | **0.049** | 100% | CP016861.2 |
| Select seq P025495.1 | Staphylococcus aureus subsp. aureus strain 3020.C01 chromosome, complete genome | 42.1 | 252 | 100% | **0.049** | 100% | CP025495.1 |
| Select seq P020714.1 | Staphylococcus aureus strain K18 chromosome, complete genome | 42.1 | 42.1 | 100% | **0.049** | 100% | CP020714.1 |
| Select seq P020713.1 | Staphylococcus aureus strain K17 chromosome, complete genome | 42.1 | 42.1 | 100% | **0.049** | 100% | CP020713.1 |
| Select seq CP016863.2 | Staphylococcus aureus subsp. aureus strain 1625.C01 chromosome, complete genome | 42.1 | 252 | 100% | **0.049** | 100% | CP016863.2 |
| Select seq CP025395.1 | Staphylococcus aureus O46 chromosome, complete genome | 42.1 | 168 | 100% | **0.049** | 100% | CP025395.1 |
| Select seq MG675880.1 | Staphylococcus aureus strain 2065MA 16S ribosomal RNA gene, partial sequence | 42.1 | 42.1 | 100% | **0.049** | 100% | MG675880.1 |
| Select seq CP025023.1 | Staphylococcus argenteus strain XNO106 chromosome, complete genome | 42.1 | 210 | 100% | **0.049** | 100% | CP025023.1 |
| Select seq CP024998.1 | Staphylococcus aureus strain 55-99-44 chromosome, complete genome | 42.1 | 210 | 100% | **0.049** | 100% | CP024998.1 |

FIG. 4a-4

Probe Staaur
G CAA GCT TCT CGT CCG TTC GC
Target GC GAA CGG ACG AGA AGC TTG C

| Select for downloading or viewing reports | Description | Max score | Total score | Query cover | E value | Ident | Accession |
|---|---|---|---|---|---|---|---|
| Select seq KY421198.1 | Staphylococcus aureus strain MT4 16S ribosomal RNA gene, partial sequence | 42.1 | 42.1 | 100% | **0.049** | 100% | KY421198.1 |
| Select seq KY421197.1 | Staphylococcus aureus strain MT1 16S ribosomal RNA gene, partial sequence | 42.1 | 42.1 | 100% | **0.049** | 100% | KY421197.1 |
| Select seq MG575995.1 | Staphylococcus argenteus strain OX0626 165 ribosomal RNA gene, partial sequence | 42.1 | 42.1 | 100% | **0.049** | 100% | MG575995.1 |
| Select seq CP023076.1 | Staphylococcus argenteus strain XNO62 chromosome, complete genome | 42.1 | 210 | 100% | **0.049** | 100% | CP023076.1 |
| Select seq MG557810.1 | Staphylococcus aureus strain 309-9 165 ribosomal RNA gene, partial sequence | 42.1 | 42.1 | 100% | **0.049** | 100% | MG557810.1 |
| Select seq CP019574.1 | Staphylococcus aureus strain USA400-0051 chromosome, complete genome | 42.1 | 202 | 100% | **0.049** | 100% | CP019574.1 |
| Select seq MG546552.1 | Staphylococcus aureus strain nwu49 16S ribosomal RNA gene, partial sequence | 42.1 | 42.1 | 100% | **0.049** | 100% | MG546552.1 |
| Select seq MG546551.1 | Staphylococcus aureus strain nwu48 165 ribosomal RNA gene, partial sequence | 42.1 | 42.1 | 100% | **0.049** | 100% | MG546551.1 |
| Select seq MG546550.1 | Staphylococcus aureus strain nwu47 165 ribosomal RNA gene, partial sequence | 42.1 | 42.1 | 100% | **0.049** | 100% | MG546550.1 |
| Select seq MG546545.1 | Staphylococcus aureus strain nwu42 165 ribosomal RNA gene, partial sequence | 42.1 | 42.1 | 100% | **0.049** | 100% | MG546545.1 |
| Select seq MG546541.1 | Staphylococcus aureus strain nwu37 165 ribosomal RNA gene, partial sequence | 42.1 | 42.1 | 100% | **0.049** | 100% | MG546541.1 |
| Select seq CP022291.1 | Staphylococcus aureus subsp. aureus strain EDCC5464 chromosome, complete genome | 42.1 | 244 | 100% | **0.049** | 100% | CP022291.1 |
| Select seq CP022290.1 | Staphylococcus aureus subsp. aureus strain EDCC5458 chromosome, complete genome | 42.1 | 252 | 100% | **0.049** | 100% | CP022290.1 |

FIG. 4a-5

Probe Staaur

G CAA GCT TCT CGT CCG TTC GC

Target GC GAA CGG ACG AGA AGC TTG C

| Select for downloading or viewing reports | Description | Max score | Total score | Query cover | E value | Ident | Accession |
|---|---|---|---|---|---|---|---|
| Select seq CP024649.1 | Staphylococcus aureus 011 chromosome, complete genome | 42.1 | 168 | 100% | **0.049** | 100% | CP024649.1 |
| Select seq AP017891.1 | Staphylococcus aureus DNA, complete genome, strain: GN3 | 42.1 | 252 | 100% | **0.049** | 100% | AP017891.1 |
| Select seq AP018349.1 | Staphylococcus aureus DNA. complete genome, strain: GN1 | 42.1 | 252 | 100% | **0.049** | 100% | AP018349.1 |
| Select seq NR_037007.2 | Staphylococcus aureus strain S33 R 16S ribosomal RNA, complete sequence | 42.1 | 42.1 | 100% | **0.049** | 100% | NR 037007.2 |
| Select seq NR_118997.2 | Staphylococcus aureus strain ATCC 12600 16S ribosomal RNA, complete sequence | 42.1 | 42.1 | 100% | **0.049** | 100% | NR 118997.2 |
| Select seq MG230264.1 | Staphylococcus aureus strain AM 16S ribosomal RNA gene, partial sequence | 42.1 | 42.1 | 100% | **0.049** | 100% | MG230264.1 |
| Select seq CP017685.1 | Staphylococcus aureus strain CFSAN007835 chromosome, complete genome | 42.1 | 252 | 100% | **0.049** | 100% | CP017685.1 |
| Select seq CP017684.1 | Staphylococcus aureus strain CFSAN007847 chromosome, complete genome | 42.1 | 252 | 100% | **0.049** | 100% | CP017684.1 |
| Select seq CP017682.1 | Staphylococcus aureus strain CFSAN007850 chromosome, complete genome | 42.1 | 244 | 100% | **0.049** | 100% | CP017682.1 |
| Select seq CP017680.1 | Staphylococcus aureus strain CFSAN007851 chromosome, complete genome | 42.1 | 244 | 100% | **0.049** | 100% | CP017680.1 |
| Select seq CP017679.1 | Staphylococcus aureus strain CFSAN007883 chromosome, complete genome | 42.1 | 252 | 100% | **0.049** | 100% | CP017679 1 |
| Select seq CP017677.1 | Staphylococcus aureus strain CFSAN007894 chromosome, complete genome | 42.1 | 244 | 100% | **0.049** | 100% | CP017677 1 |
| Select seq CP020741.1 | Staphylococcus aureus strain HZW450 chromosome, complete genome | 42.1 | 252 | 100% | **0.049** | 100% | CP020741.1 |

FIG. 4a-6

Probe Staaur
G CAA GCT TCT CGT CCG TTC GC
Target GC GAA CGG ACG AGA AGC TTG C

| Select for downloading or viewing reports | Description | Max score | Total score | Query cover | E value | Ident | Accession |
|---|---|---|---|---|---|---|---|
| Select seq CP023560.1 | Staphylococcus aureus strain NMR08 chromosome | 42.1 | 168 | 100% | **0.049** | 100% | CP023560.1 |
| Select seq CP023500.1 | Staphylococcus aureus strain FDAARGOS 412 chromosome, complete genome | 42.1 | 252 | 100% | **0.049** | 100% | CP023500.1 |
| Select seq CP023391.1 | Staphylococcus aureus subsp. aureus strain Newman D2C chromosome, complete genome | 42.1 | 210 | 100% | **0.049** | 100% | CP023391.1 |
| Select seq CP023390.1 | Staphylococcus aureus subsp. aureus str. Newman strain NYU Newman chromosome, complete genome | 42.1 | 210 | 100% | **0.049** | 100% | CP023390.1 |
| Select seq MF784283.1 | Staphylococcus aureus strain s1266-9 16S ribosomal RNA gene, partial sequence | 42.1 | 42.1 | 100% | **0.049** | 100% | MF784283.1 |
| Select seq MF375202.1 | Staphylococcus sp. strain S96 16S ribosomal RNA gene, partial sequence | 42.1 | 42.1 | 100% | **0.049** | 100% | MF375202.1 |
| Select seq MF375199.1 | Staphylococcus sp. strain S91 16S ribosomal RNA gene, partial sequence | 42.1 | 42.1 | 100% | **0.049** | 100% | MF375199.1 |
| Select seq LC036194.1 | Staphylococcus aureus genes for genomic island SaPIT, complete sequence, strain: TOHH628 | 42.1 | 42.1 | 100% | **0.049** | 100% | LC036194.1 |
| Select seq AP017922.1 | Staphylococcus aureus DNA, complete genome, strain: JP080 | 42.1 | 210 | 100% | **0.049** | 100% | AP017922.1 |
| Select seq AP015012.1 | Staphylococcus aureus DNA, almost complete genome, strain: No.10 | 42.1 | 244 | 100% | **0.049** | 100% | AP015012.1 |
| Select seq MF158084.1 | Staphylococcus aureus strain SABRC30 16S ribosomal RNA gene, partial sequence | 42.1 | 42.1 | 100% | **0.049** | 100% | MF158084.1 |
| Select seq MF158082.1 | Staphylococcus aureus strain SABRC28 16S ribosomal RNA gene, partial sequence | 42.1 | 42.1 | 100% | **0.049** | 100% | MF158082.1 |
| Select seq MF158081.1 | Staphylococcus aureus strain SABRC27 16S ribosomal RNA gene, partial sequence | 42.1 | 42.1 | 100% | **0.049** | 100% | MF158081.1 |

FIG. 4a-7

| | |
|---|---|
| Probe | Staaur<br>G CAA GCT TCT CGT CCG TTC GC |
| Target | GC GAA CGG ACG AGA AGC TTG C |

| **Select for downloading or viewing reports** | **Description** | Max score | Total score | Query cover | **E value** | Ident | **Accession** |
|---|---|---|---|---|---|---|---|
| Select seq MF158080.1 | Staphylococcus aureus strain SABRC26 16S ribosomal RNA gene, partial sequence | 42.1 | 42.1 | 100% | **0.049** | 100% | MF158080.1 |
| Select seq MF158078.1 | Staphylococcus aureus strain SABRC24 16S ribosomal RNA gene, partial sequence | 42.1 | 42.1 | 100% | **0.049** | 100% | MF158078.1 |
| Select seq MF158077.1 | Staphylococcus aureus strain SABRC23 16S ribosomal RNA gene, partial sequence | 42.1 | 42.1 | 100% | **0.049** | 100% | MF158077.1 |
| Select seq MF158076.1 | Staphylococcus aureus strain SABRC22 16S ribosomal RNA gene, partial sequence | 42.1 | 42.1 | 100% | **0.049** | 100% | MF158076.1 |
| Select seq MF158075.1 | Staphylococcus aureus strain SABRC21 16S ribosomal RNA gene, partial sequence | 42.1 | 42.1 | 100% | **0.049** | 100% | MF158075.1 |
| Select seq MF158073.1 | Staphylococcus aureus strain SABRC19 16S ribosomal RNA gene, partial sequence | 42.1 | 42.1 | 100% | **0.049** | 100% | MF158073.1 |
| Select seq MF158072.1 | Staphylococcus aureus strain SABRC18 16S ribosomal RNA gene, partial sequence | 42.1 | 42.1 | 100% | **0.049** | 100% | MF158072.1 |
| Select seq MF158070.1 | Staphylococcus aureus strain SABRC16 16S ribosomal RNA gene, partial sequence | 42.1 | 42.1 | 100% | **0.049** | 100% | MF158070.1 |
| Select seq MF158068.1 | Staphylococcus aureus strain SABRC14 16S ribosomal RNA gene, partial sequence | 42.1 | 42.1 | 100% | **0.049** | 100% | MF158068.1 |

FIG. 4a-8

Staaur probe 5'-1; Staaur probe with stem; Staaur probe 3'+1

Concattinated probe gctcgacttgcatgtattaggccagaagcaagcttctcgtccgtccggtccgccgctaacatcagag Concattinated target tggcctaatacatgcaagtcgagccgaacggacgagaagcttgcttcctctgatgttagcggcggac

| Select for downloading or viewing reports | Description | Max score | Total score | Query cover | E value | Ident | Accession |
|---|---|---|---|---|---|---|---|
| Select seq LT685570.1 | Staphylococcus aureus partial 16S rRNA gene, isolate 75T 10985 | 105 | 105 | 97% | **9.00E-20** | 97% | LT685570.1 |
| Select seq JF919996.1 | Staphylococcus aureus strain 9-6-2-9 16S ribosomal RNA gene, partial sequence | 105 | 105 | 97% | **9.00E-20** | 97% | JF919996.1 |
| Select seq AP018376.1 | Staphylococcus aureus SA003 DNA, nearly complete genome | 97.6 | 390 | 97% | **2.00E-17** | 97% | AP018376.1 |
| Select seq MG971399.1 | Staphylococcus aureus strain NBRC 100910 16S ribosomal RNA gene, partial sequence | 97.6 | 97.6 | 97% | **2.00E-17** | 97% | MG971399.1 |
| Select seq MG971398.1 | Staphylococcus aureus strain NBRC 100910 16S ribosomal RNA gene, partial sequence | 97.6 | 97.6 | 97% | **2.00E-17** | 97% | MG971398.1 |
| Select seq CP012119.2 | Staphylococcus aureus subsp. aureus strain USA300 2014.C01 chromosome, complete genome | 97.6 | 577 | 97% | **2.00E-17** | 97% | CP012119.2 |
| Select seq MG966418.1 | Staphylococcus aureus strain AS2 16S ribosomal RNA gene, partial sequence | 97.6 | 97.6 | 97% | **2.00E-17** | 97% | MG966418.1 |
| Select seq CP026968.1 | Staphylococcus aureus strain FDAARGOS 1 chromosome, complete genome | 97.6 | 683 | 97% | **2.00E-17** | 97% | CP026968.1 |
| Select seq CP026964.1 | Staphylococcus aureus strain FDAARGOS 2 chromosome, complete genome | 97.6 | 585 | 97% | **2.00E-17** | 97% | CP026964.1 |
| Select seq CP026962.1 | Staphylococcus aureus strain FDAARGOS 6 chromosome, complete genome | 97.6 | 585 | 97% | **2.00E-17** | 97% | CP026962.1 |
| Select seq CP026961.1 | Staphylococcus aureus strain FDAARGOS 10 chromosome, complete genome | 97.6 | 585 | 97% | **2.00E-17** | 97% | CP026961.1 |
| Select seq CP026960.1 | Staphylococcus aureus strain FDAARGOS 15 chromosome, complete genome | 97.6 | 585 | 97% | **2.00E-17** | 97% | CP026960.1 |
| Select seq CP026958.1 | Staphylococcus aureus strain FDAARGOS 40 chromosome, complete genome | 97.6 | 488 | 97% | **2.00E-17** | 97% | CP026958.1 |

FIG. 4b-1

Staaur probe 5'-1; Staaur probe with stem; Staaur probe 3'+1

Concattinated probe gctcgacttgcatgtattaggccagaagcaagcttctcgtccgtccggtccgccgctaacatcagag Concattinated target tggcctaatacatgcaagtcgagccgaacggacgagaagcttgcttcctctgatgttagcggcggac

| **Select for downloading or viewing reports** | **Description** | Max score | Total score | Query cover | **E value** | Ident | **Accession** |
|---|---|---|---|---|---|---|---|
| Select seq CP026957.1 | Staphylococcus aureus strain FDAARGOS 43 chromosome. complete genome | 97.6 | 585 | 97% | **2.00E-17** | 97% | CP026957.1 |
| Select seq CP026953.1 | Staphylococcus aureus strain FDAARGOS 48 chromosome, complete genome | 97.6 | 577 | 97% | **2.00E-17** | 97% | CP026953.1 |
| Select seq CP016858.2 | Staphylococcus aureus subsp. aureus strain 1971.C01 chromosome, complete genome | 97.6 | 488 | 97% | **2.00E-17** | 97% | CP016858.2 |
| Select seq CP016855.2 | Staphylococcus aureus subsp. aureus strain 5118.N chromosome, complete genome | 97.6 | 577 | 97% | **2.00E-17** | 97% | CP016855.2 |
| Select seq CP007539.3 | Staphylococcus aureus subsp. aureus strain FDAARGOS 5 chromosome, complete genome | 97.6 | 585 | 97% | **2.00E-17** | 97% | CP007539.3 |
| Select seq CP014064.2 | Staphylococcus aureus strain FDAARGOS 159 chromosome, complete genome | 97.6 | 577 | 97% | **2.00E-17** | 97% | CP014064.2 |
| Select seq CP026080.1 | Staphylococcus aureus strain NRS137 chromosome, complete genome | 97.6 | 585 | 97% | **2.00E-17** | 97% | CP026080.1 |
| Select seq CP026077.1 | Staphylococcus aureus strain NRS107 chromosome, complete genome | 97.6 | 585 | 97% | **2.00E-17** | 97% | CP026077.1 |
| Select seq CP026074.1 | Staphylococcus aureus strain HPV107 chromosome, complete genome | 97.6 | 577 | 97% | **2.00E-17** | 97% | CP026074.1 |
| Select seq CP026064.1 | Staphylococcus aureus strain NRS271 chromosome, complete genome | 97.6 | 480 | 97% | **2.00E-17** | 97% | CP026064.1 |
| Select seq CP026079.1 | Staphylococcus aureus strain NRS70 chromosome, complete genome | 97.6 | 480 | 97% | **2.00E-17** | 97% | CP026079.1 |
| Select seq CP026076.1 | Staphylococcus aureus strain TCH 959 chromosome, complete genome | 97.6 | 577 | 97% | **2.00E-17** | 97% | CP026076.1 |
| Select seq CP026073.1 | Staphylococcus aureus strain Mw2 chromosome, complete genome | 97.6 | 585 | 97% | **2.00E-17** | 97% | CP026073.1 |

FIG. 4b-2

Staaur probe 5'-1; Staaur probe with stem; Staaur probe 3'+1

Concattinated probe gctcgacttgcatgtattaggccagaagcaagcttctcgtccgtccggtccgccgctaacatcagag Concattinated target tggcctaatacatgcaagtcgagccgaacggacgagaagcttgcttcctctgatgttagcggcggac

| Select for downloading or viewing reports | Description | Max score | Total score | Query cover | E value | Ident | Accession |
|---|---|---|---|---|---|---|---|
| Select seq CP026072.1 | Staphylococcus aureus strain NRS120 chromosome, complete genome | 97.6 | 480 | 97% | **2.00E-17** | 97% | CP026072.1 |
| Select seq CP026071.1 | Staphylococcus aureus strain NRS143 chromosome, complete genome | 97.6 | 585 | 97% | **2.00E-17** | 97% | CP026071.1 |
| Select seq CP026070.1 | Staphylococcus aureus strain NRS133 chromosome, complete genome | 97.6 | 585 | 97% | **2.00E-17** | 97% | CP026070.1 |
| Select seq CP026069.1 | Staphylococcus aureus strain NRS1 chromosome, complete genome | 97.6 | 480 | 97% | **2.00E-17** | 97% | CP026069.1 |
| Select seq CP026068.1 | Staphylococcus aureus strain NRS146 chromosome, complete genome | 97.6 | 585 | 97% | **2.00E-17** | 97% | CP026068.1 |
| Select seq CP026067.1 | Staphylococcus aureus strain NRS153 chromosome, complete genome | 97.6 | 585 | 97% | **2.00E-17** | 97% | CP026067.1 |
| Select seq CP026066.1 | Staphylococcus aureus strain NRS484 chromosome, complete genome | 97.6 | 585 | 97% | **2.00E-17** | 97% | CP026066.1 |
| Select seq CP026063.1 | Staphylococcus aureus strain NRS149 chromosome, complete genome | 97.6 | 577 | 97% | **2.00E-17** | 97% | CP026063.1 |
| Select seq MG818959.1 | Staphylococcus aureus strain FA-1 16S ribosomal RNA gene, partial sequence | 97.6 | 97.6 | 97% | **2.00E-17** | 97% | MG818959.1 |
| Select seq CP018629.1 | Staphylococcus aureus strain MRSA107 chromosome, complete genome | 97.6 | 488 | 97% | **2.00E-17** | 97% | CP018629.1 |
| Select seq MG757681.1 | Staphylococcus aureus strain ZS-28C 16S ribosomal RNA gene, partial sequence | 97.6 | 97.6 | 97% | **2.00E-17** | 97% | MG757681.1 |
| Select seq CP016856.2 | Staphylococcus aureus subsp. aureus strain 2148.N chromosome, complete genome | 97.6 | 577 | 97% | **2.00E-17** | 97% | CP016856.2 |
| Select seq CP012120.2 | Staphylococcus aureus subsp. aureus strain USA300 2014.C02 chromosome, complete genome | 97.6 | 577 | 97% | **2.00E-17** | 97% | CP012120.2 |

FIG. 4b-3

Staaur probe 5'-1; Staaur probe with stem; Staaur probe 3'+1
Concattinated probe gctcgacttgcatgtattaggccagaagcaagcttctcgtccgtccggtccgccgctaacatcagag
Concattinated target tggcctaatacatgcaagtcgagccgaacggacgagaagcttgcttcctctgatgttagcggcggac

| Select for downloading or viewing reports | Description | Max score | Total score | Query cover | E value | Ident | Accession |
|---|---|---|---|---|---|---|---|
| Select seq CP017094.2 | Staphylococcus aureus subsp. aureus strain 2148.C01 chromosome, complete genome | 97.6 | 577 | 97% | **2.00E-17** | 97% | CP017094.2 |
| Select seq CP016861.2 | Staphylococcus aureus subsp. aureus strain 1969.N chromosome.complete genome | 97.6 | 577 | 97% | **2.00E-17** | 97% | CP016861.2 |
| Select seq CP025495.1 | Staphylococcus aureus subsp. aureus strain 3020.C01 chromosome, complete genome | 97.6 | 577 | 97% | **2.00E-17** | 97% | CP025495.1 |
| Select seq CP020714.1 | Staphylococcus aureus strain K18 chromosome, complete genome | 97.6 | 97.6 | 97% | **2.00E-17** | 97% | CP020714.1 |
| Select seq CP020713.1 | Staphylococcus aureus strain K17 chromosome, complete genome | 97.6 | 97.6 | 97% | **2.00E-17** | 97% | CP020713.1 |
| Select seq CP016863.2 | Staphylococcus aureus subsp. aureus strain 1625.C01 chromosome, complete genome | 97.6 | 577 | 97% | **2.00E-17** | 97% | CP016863.2 |
| Select seq CP025395.1 | Staphylococcus aureus 046 chromosome, complete genome | 97.6 | 390 | 97% | **2.00E-17** | 97% | CP025395.1 |
| Select seq CP025023.1 | Staphylococcus argenteus strain XNO106 chromosome, complete genom | 97.6 | 488 | 97% | **2.00E-17** | 97% | CP025023.1 |
| Select seq CP024998.1 | Staphylococcus aureus strain 55-99-44 chromosome, complete genome | 97.6 | 488 | 97% | **2.00E-17** | 97% | CP024998.1 |
| Select seq MG575995.1 | Staphylococcus argenteus strain OX0626 16S ribosomal RNA gene, partial sequence | 97.6 | 97.6 | 97% | **2.00E-17** | 97% | MG575995.1 |
| Select seq CP023076.1 | Staphylococcus argenteus strain XN062 chromosome, complete genome | 97.6 | 488 | 97% | **2.00E-17** | 97% | CP023076.1 |
| Select seq CP019574.1 | Staphylococcus aureus strain USA400-0051 chromosome, complete genome | 97.6 | 480 | 97% | **2.00E-17** | 97% | CP019574.1 |
| Select seq CP022291.1 | Staphylococcus aureus subsp. aureus strain EDCC5464 chromosome, complete genome | 97.6 | 577 | 97% | **2.00E-17** | 97% | CP022291.1 |

FIG. 4b-4

Staaur probe 5'-1; Staaur probe with stem; Staaur probe 3'+1

Concattinated probe gctcgacttgcatgtattaggccagaagcaagcttctcgtccgtccggtccgccgctaacatcagag Concattinated target tggcctaatacatgcaagtcgagccgaacggacgagaagcttgcttcctctgatgttagcggcggac

| **Select for downloading or viewing reports** | **Description** | Max score | Total score | Query cover | **E value** | Ident | **Accession** |
|---|---|---|---|---|---|---|---|
| Select seq CP022290.1 | Staphylococcus aureus subsp. aureus strain EDCC5458 chromosome, complete genome | 97.6 | 577 | 97% | **2.00E-17** | 97% | CP022290.1 |
| Select seq CP024649.1 | Staphylococcus aureus 011 chromosome, complete genome | 97.6 | 390 | 97% | **2.00E-17** | 97% | CP024649.1 |
| Select seq AP017891.1 | Staphylococcus aureus DNA, complete genome, strain: GN3 | 97.6 | 585 | 97% | **2.00E-17** | 97% | AP017891.1 |
| Select seq AP018349.1 | Staphylococcus aureus DNA, complete genome, strain: GN1 | 97.6 | 585 | 97% | **2.00E-17** | 97% | AP018349.1 |
| Select seq NR 037007.2 | Staphylococcus aureus strain S33 R 16S ribosomal RNA, complete sequence | 97.6 | 97.6 | 97% | **2.00E-17** | 97% | NR 037007.2 |
| Select seq NR 118997.2 | Staphylococcus aureus strain ATCC 12600 16S ribosomal RNA, complete sequence | 97.6 | 97.6 | 97% | **2.00E-17** | 97% | NR 118997.2 |
| Select seq CP017685.1 | Staphylococcus aureus strain CFSAN007835 chromosome, complete genome | 97.6 | 585 | 97% | **2.00E-17** | 97% | CP017685.1 |
| Select seq CP017684.1 | Staphylococcus aureus strain CFSAN007847 chromosome, complete genome | 97.6 | 585 | 97% | **2.00E-17** | 97% | CP017684.1 |
| Select seq CP017682.1 | Staphylococcus aureus strain CFSAN007850 chromosome, complete genome | 97.6 | 577 | 97% | **2.00E-17** | 97% | CP017682.1 |
| Select seq CP017680.1 | Staphylococcus aureus strain CFSAN007851 chromosome, complete genome | 97.6 | 577 | 97% | **2.00E-17** | 97% | CP017680.1 |
| Select seq CP017679.1 | Staphylococcus aureus strain CFSAN007883 chromosome, complete genome | 97.6 | 585 | 97% | **2.00E-17** | 97% | CP017679.1 |
| Select seq CP017677.1 | Staphylococcus aureus strain CFSAN007894 chromosome, complete genome | 97.6 | 577 | 97% | **2.00E-17** | 97% | CP017677.1 |
| Select seq CP020741.1 | Staphylococcus aureus strain HZW450 chromosome, complete genome | 97.6 | 585 | 97% | **2.00E-17** | 97% | CP020741.1 |
| Select seq CP023560.1 | Staphylococcus aureus strain NMR08 chromosome | 97.6 | 390 | 97% | **2.00E-17** | 97% | CP023560.1 |

FIG. 4b-5

Staaur probe 5'-1; Staaur probe with stem; Staaur probe 3'+1

Concattinated probe gctcgacttgcatgtattaggccagaagcaagcttctcgtccgtccggtccgccgctaacatcagag Concattinated target tggcctaatacatgcaagtcgagccgaacggacgagaagcttgcttcctctgatgttagcggcggac

| **Select for downloading or viewing reports** | **Description** | Max score | Total score | Query cover | **E value** | Ident | **Accession** |
|---|---|---|---|---|---|---|---|
| Select seq CP023500.1 | Staphylococcus aureus strain FDAARGOS 412 chromosome. complete renome | 97.6 | 585 | 97% | **2.00E-17** | 97% | CP023500.1 |
| Select seq CP023391.1 | Staphylococcus aureus subsp. aureus strain Newman D2C chromosome,complete renome | 97.6 | 488 | 97% | **2.00E-17** | 97% | CP023391.1 |
| Select seq CP023390.1 | Staphylococcus aureus subsp. aureus str. Newman strain NYU Newman chromosome, complete genome | 97.6 | 488 | 97% | **2.00E-17** | 97% | CP023390.1 |
| Select seq MF784283.1 | Staphylococcus aureus strain s1266-9 16S ribosomal RNA gene, partial sequence | 97.6 | 97.6 | 97% | **2.00E-17** | 97% | MF784283.1 |
| Select seq AP017922.1 | Staphylococcus aureus DNA, complete genome, strain: JP080 | 97.6 | 488 | 97% | **2.00E-17** | 97% | AP017922.1 |
| Select seq AP014921.1 | Staphylococcus aureus DNA, complete genome, strain: JH4899 | 97.6 | 585 | 97% | **2.00E-17** | 97% | AP014921.1 |
| Select seq MF421788.1 | Staphylococcus aureus subsp. aureus strain DBT36 16S ribosomal RNA gene, partial sequence | 97.6 | 97.6 | 97% | **2.00E-17** | 97% | MF421788.1 |
| Select seq CP016398.1 | Staphylococcus aureus strain FORC 040, complete genome | 97.6 | 577 | 97% | **2.00E-17** | 97% | CP016398.1 |
| Select seq CP017115.1 | Staphylococcus aureus strain FORC 045, complete genome | 97.6 | 480 | 97% | **2.00E-17** | 97% | CP017115.1 |
| Select seq MF372564.1 | Listeria monocytogenes strain 11125 16S ribosomal RNA gene, partial sequence | 97.6 | 97.6 | 97% | **2.00E-17** | 97% | MF372564.1 |
| Select seq CP017091.1 | Staphylococcus aureus subsp. aureus strain ISU926, complete genome | 97.6 | 585 | 97% | **2.00E-17** | 97% | CP017091.1 |
| Select seq CP017090.1 | Staphylococcus aureus strain ISU935, complete genome | 97.6 | 577 | 97% | **2.00E-17** | 97% | CP017090.1 |
| Select seq CP021907.1 | Staphylococcus aureus strain Seattle 1945 isolate G478, complete genome | 97.6 | 585 | 97% | **2.00E-17** | 97% | CP021907.1 |
| Select seq CP021905.1 | Staphylococcus aureus strain Seattle 1945 isolate G477, complete genome | 97.6 | 585 | 97% | **2.00E-17** | 97% | CP021905.1 |

FIG. 4b-6

Staaur probe 5'-1; Staaur probe with stem; Staaur probe 3'+1

Concattinated probe gctcgacttgcatgtattaggccagaagcaagcttctcgtccgtccggtccgccgctaacatcagag Concattinated target tggcctaatacatgcaagtcgagccgaacggacgagaagcttgcttcctctgatgttagcggcggac

| Select for downloading or viewing reports | Description | Max score | Total score | Query cover | E value | Ident | Accession |
|---|---|---|---|---|---|---|---|
| Select seq CP015447.1 | Staphylococcus aureus strain M92, complete genome | 97.6 | 585 | 97% | **2.00E-17** | 97% | CP015447.1 |
| Select seq KY770779.1 | Staphylococcus aureus strain DSTNMRM2 16S ribosomal RNA gene, partial sequence | 97.6 | 97.6 | 97% | **2.00E-17** | 97% | KY770779.1 |
| Select seq CP019595.1 | Staphylococcus aureus strain GD1677, complete genome | 97.6 | 585 | 97% | **2.00E-17** | 97% | CP019595.1 |
| Select seq CP019594.1 | Staphylococcus aureus strain GD1539, complete genome | 97.6 | 585 | 97% | **2.00E-17** | 97% | CP019594.1 |
| Select seq CP019593.1 | Staphylococcus aureus strain GD705, complete genome | 97.6 | 585 | 97% | **2.00E-17** | 97% | CP019593.1 |
| Select seq CP019592.1 | Staphylococcus aureus strain GD5, complete genome | 97.6 | 585 | 97% | **2.00E-17** | 97% | CP019592.1 |
| Select seq CP019591.1 | Staphylococcus aureus strain 293G, complete genome | 97.6 | 585 | 97% | **2.00E-17** | 97% | CP019591.1 |
| Select seq CP019590.1 | Staphylococcus aureus strain C2406, complete genome | 97.6 | 577 | 97% | **2.00E-17** | 97% | CP019590.1 |
| Select seq CP020619.1 | Staphylococcus aureus strain JE2 chromosome, complete genome | 97.6 | 577 | 97% | **2.00E-17** | 97% | CP020619.1 |
| Select seq CP019945.1 | Staphylococcus aureus strain BA01611, complete genome | 97.6 | 488 | 97% | **2.00E-17** | 97% | CP019945.1 |

A

FIG. 4b-7

(A)

| | | | | | | | |
|---|---|---|---|---|---|---|---|
| Select seq CP020020.1 | Staphylococcus aureus subsp. aureus strain ATCC 6538, complete genome | 97.6 | 585 | 97% | **2.00E-17** | 97% | CP020020.1 |
| Select seq CP020019.1 | Staphylococcus aureus strain 08S00974, complete genome | 97.6 | 585 | 97% | **2.00E-17** | 97% | CP020019.1 |
| Select seq KY630525.1 | Staphylococcus aureus strain KSAT2 16S ribosomal RNA gene, partial sequence | 97.6 | 97.6 | 97% | **2.00E-17** | 97% | KY630525.1 |
| Select seq CP014444.1 | Staphylococcus aureus strain USA300-SUR24, complete genome | 97.6 | 488 | 97% | **2.00E-17** | 97% | CP014444.1 |
| Select seq CP014441.1 | Staphylococcus aureus strain USA300-SUR23, complete genome | 97.6 | 488 | 97% | **2.00E-17** | 97% | CP014441.1 |
| Select seq CP014438.1 | Staphylococcus aureus strain USA300-SUR22, complete genome | 97.6 | 488 | 97% | **2.00E-17** | 97% | CP014438.1 |
| Select seq CP014435.1 | Staphylococcus aureus strain USA300-SUR21, complete genome | 97.6 | 488 | 97% | **2.00E-17** | 97% | CP014435.1 |

FIG. 4b-7 continued

Staaur probe 5'-1; Staaur probe with stem; Staaur probe 3'+1

Concattinated probe gctcgacttgcatgtattaggccagaagcaagcttctcgtccgtccggtccgccgctaacatcagag Concattinated target tggcctaatacatgcaagtcgagccgaacggacgagaagcttgcttcctctgatgttagcggcggac

| Select for downloading or viewing reports | Description | Max score | Total score | Query cover | E value | Ident | Accession |
|---|---|---|---|---|---|---|---|
| Select seq CP014432.1 | Staphylococcus aureus strain USA300-SUR20, complete genome | 97.6 | 488 | 97% | **2.00E-17** | 97% | CP014432.1 |
| Select seq CP014429.1 | Staphylococcus aureus strain USA300-SUR19, complete genome | 97.6 | 488 | 97% | **2.00E-17** | 97% | CP014429.1 |
| Select seq CP014426.1 | Staphylococcus aureus strain USA300-SUR18 | 97.6 | 488 | 97% | **2.00E-17** | 97% | CP014426.1 |

FIG. 4b-8

TEM! #1

QC of respective probe integrity with respect to hybridisation to respective target sequencse: http://unafold.rna.albany.edu/?q=DINAMelt/Two-state-melting Pass: if alignment is without error, no gaps, no mismatches

| | |
|---|---|
| Target | UGCUGCAACUUUAUCCGCCUCC |
| Probe with stem | Atgctgcat ggaggcggataaagttgcagca atgcagcat |
| Two state melting | ΔG = -24.9 ΔH = -216.8 ΔS = -571.7 Tm = 75.7°C |

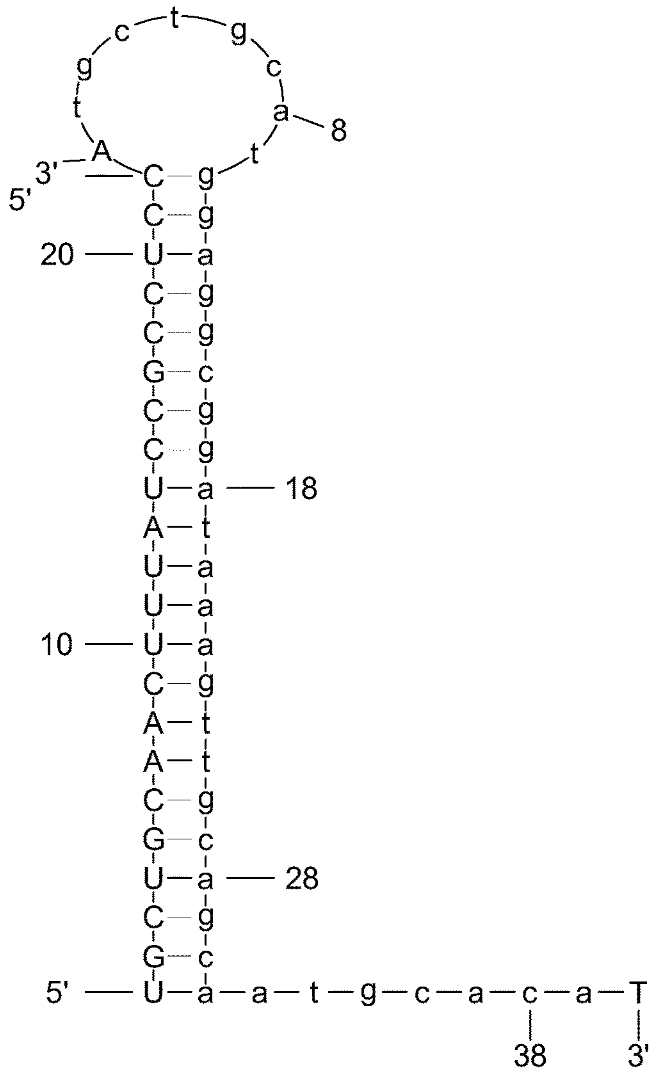

*dG = -24.922 dH = -216.8 A-B*

RNAfold data ΔG = -1.74 ΔH = -56.50 ΔS = -163.15 Tm = 73.2°C

FIG. 5a-1

QC of probe integrity with respect to hairpin loop formation with Quickfold: http://unafold.rna.albany.edu/?q =DINAMelt/Quickfold Pass: Free energy of hairpin loop formation must be negative under hybridisation conditions and <20% of the free energy generated under hybridisation conditions

*dG = -1.736 A*

RNAfold data $\Delta G$ = -1.72 $\Delta H$ = -67.00 $\Delta S$ = -194.49 Tm = 71.3°C

TEM! #2

QC of respective probe integrity with respect to hybridisation to respective target sequencse: http://unafold.rna.albany.edu/?q=DINA Melt/Two-state-melting Pass: if alignment is without error, no gaps, no mismatches

| | |
|---|---|
| Target | AUCCAGUCUAUUAAUUGUUGCCGGG |
| Probe with stem | Atgctgcat cccggcaacaattaatagactggat atgcagcaT |
| Two state melting | ΔG = -24.0 ΔH = -230.1 ΔS = -613.9 Tm = 73.5°C |

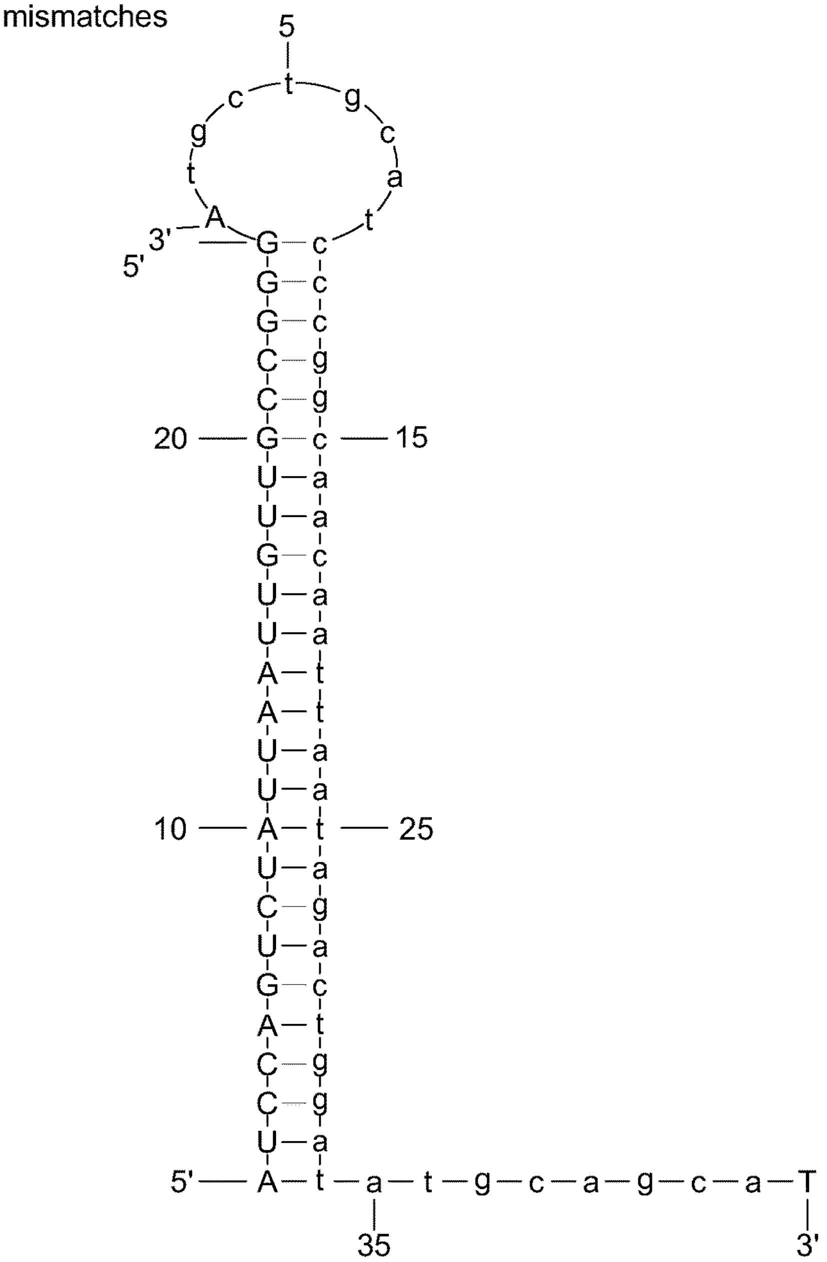

*dG = -24.043 dH = -230.1 A-B*

RNAfold data ΔG = -1.59 ΔH = -88.80 ΔS = -259.82 Tm = 68.6°C

FIG. 5b-1

QC of probe integrity with respect to hairpin loop formation with Quickfold: http://unafold.rna.albany.edu/?q =DINAMelt/Quickfold Pass: Free energy of hairpin loop formation must be negative under hybridisation conditions and <20% of the free energy generated under hybridisation conditions RNAfold data ΔG = -0.79 ΔH = -72.10 ΔS = -212.45 Tm = 66.2°C

TEM! #3

QC of respective probe integrity with respect to hybridisation to respective target sequencse: http://unafold.rna.albany.edu/?q=DINAMelt/Two-state-melting Pass: if alignment is without error, no gaps, no mismatches

| | |
|---|---|
| Target | AAGCUAGAGUAAGUAGUUCGCCAG |
| Probe with stem | Atgctgcat ctggcgaactacttactctagctt atgcagcaT |
| Two state melting | ΔG = -24.1 ΔH = -219.3 ΔS = -581.7 Tm = 74.1°C |

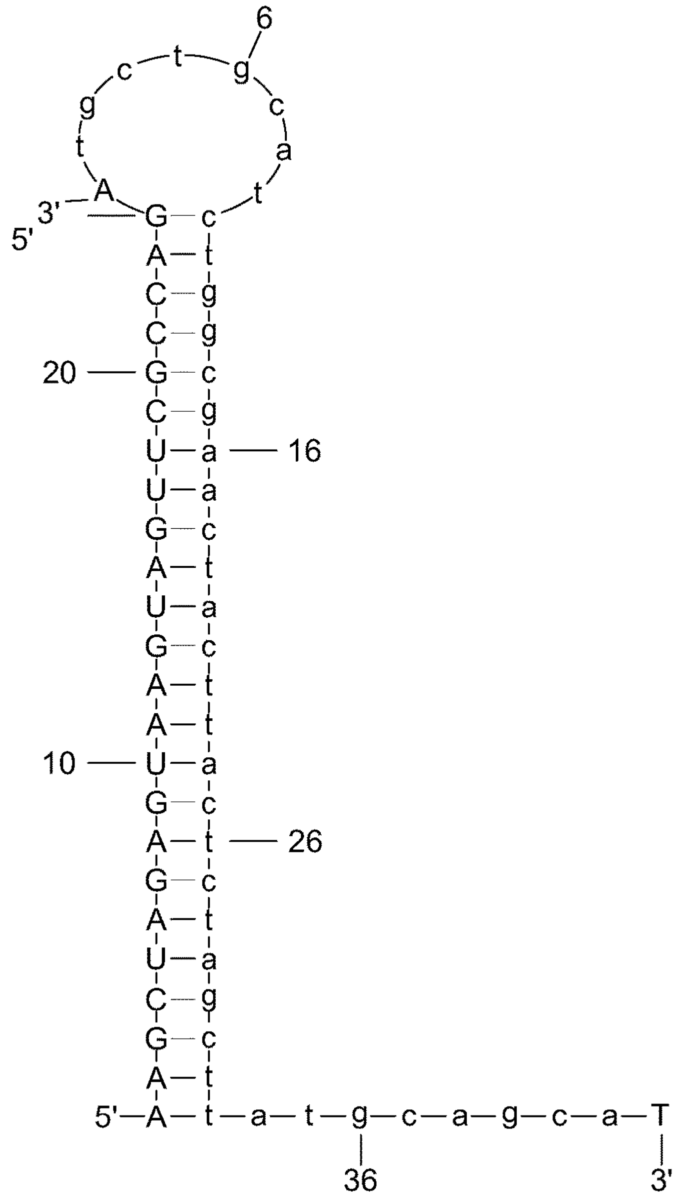

*dG = -24.067 dH = - 219.3 A-B*

RNAfold data ΔG = -1.22 ΔH = -67.80 ΔS = -198.36 Tm = 68.7°C

FIG. 5c-1

QC of probe integrity with respect to hairpin loop formation with Quickfold: http://unafold.rna.albany.edu/?q=DINAMelt/Quickfold Pass: Free energy of hairpin loop formation must be negative under hybridisation conditions and <20% of the free energy generated under hybridisation conditions

*dG = -1.224 A*

RNAfold data ΔG = -1.14 ΔH = -84.80 ΔS = -249.25 Tm = 67.1°C

TEM! #4

QC of respective probe integrity with respect to hybridisation to respective target sequencse: http://unafold.rna.albany.edu/?q=DINAMelt/Two-state-melting Pass: if alignment is without error, no gaps, no mismatches

| | |
|---|---|
| Target | UUAAUAGUUUGCGCAACGUUGUUGCC |
| Probe with stem | Atgctgcat ggcaacaacgttgcgcaaactattaa atgcagcaT |
| Two state melting | ΔG = -24.6 ΔH = -234.2 ΔS = -624.5 Tm = 74.1°C |

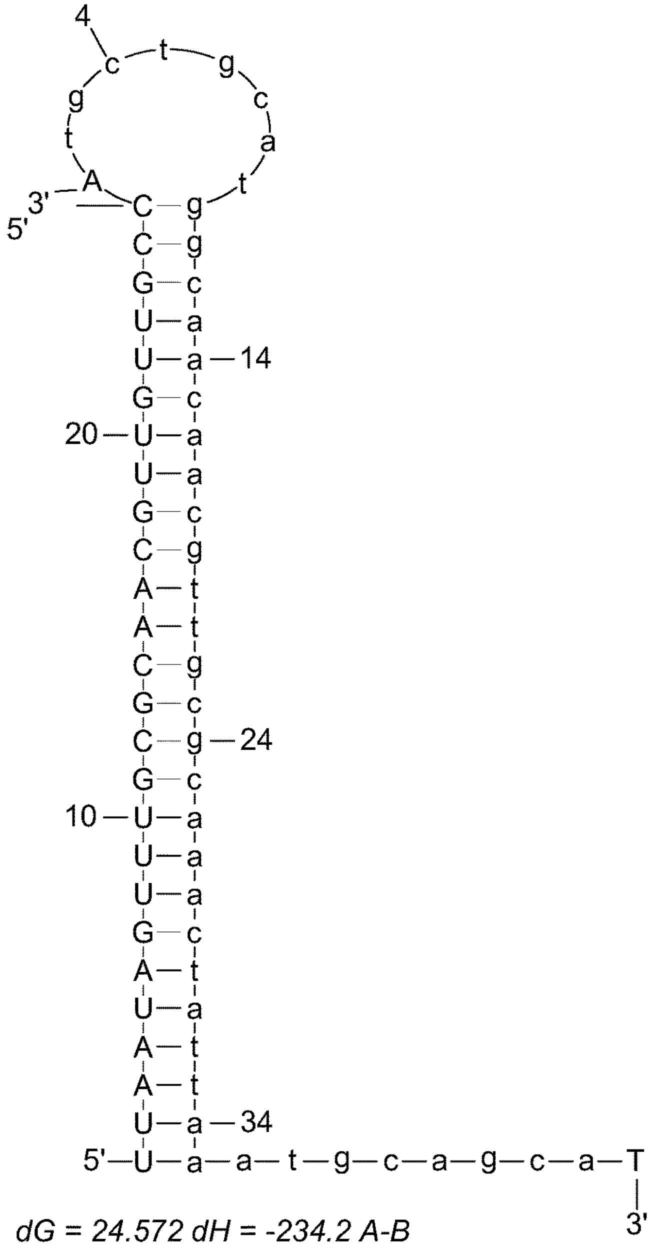

*dG = 24.572 dH = -234.2 A-B*

RNAfold data ΔG = -1.18 ΔH = -67.00 ΔS = -196.10 Tm = 68.5°C

FIG. 5d-1

QC of probe integrity with respect to hairpin loop formation with Quickfold: http://unafold.rna.albany.edu/?q =DINAMelt/Quickfold Pass: Free energy of hairpin loop formation must be negative under hybridisation conditions and <20% of the free energy generated under hybridisation conditions

*dG = -1.181 A*

RNAfold data ΔG = -0.96 ΔH = -67.60 ΔS = -198.54 Tm = 67.3°C

TEM! #5

QC of respective probe integrity with respect to hybridisation to respective target sequencse: http://unafold.rna.albany.edu/?q=DINAMelt/Two-state-melting Pass: if alignment is without error, no gaps, no mismatches

| | |
|---|---|
| Target | AUUGCUGCAGGCAUCGUGGUG |
| Probe with stem | Atgctgcat caccacgatgcctgcagcaat atgcagcaT |
| Two state melting | ΔG = -23.8 ΔH = -210.6 ΔS = -556.5 Tm = 74.2°C |

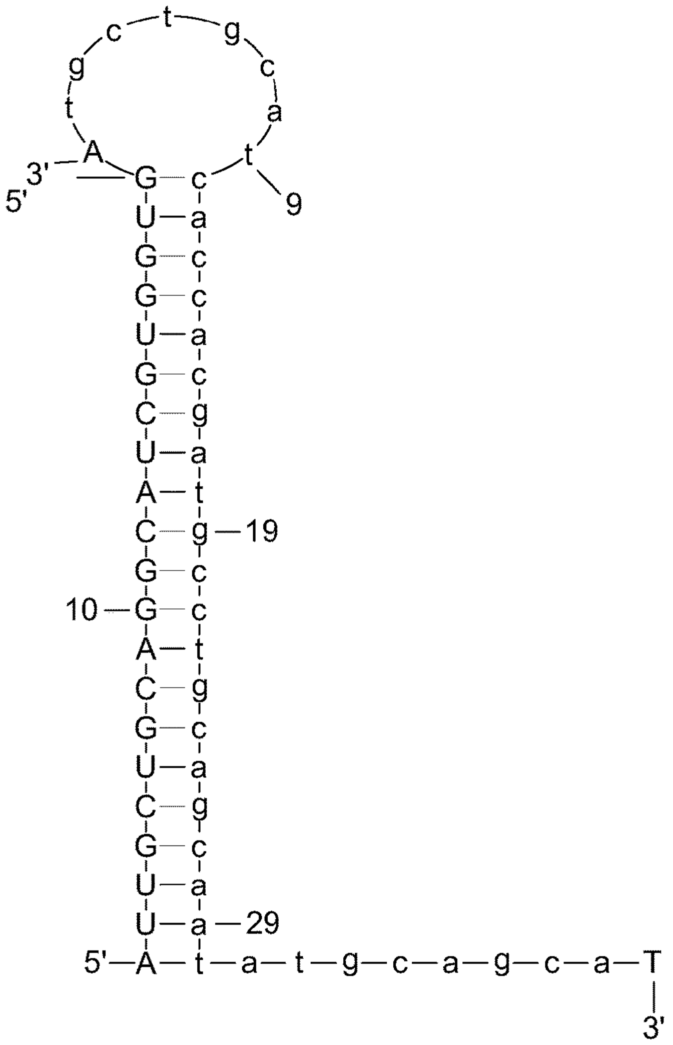

*dG = 23.81 dH = -210.6 A-B*

RNAfold data ΔG = -1.81 ΔH = -56.90 ΔS = -164.13 Tm = 73.5°C

FIG. 5e-1

QC of probe integrity with respect to hairpin loop formation with Quickfold: http://unafold.rna.albany.edu/?q =DINAMelt/Quickfold Pass: Free energy of hairpin loop formation must be negative under hybridisation conditions and <20% of the free energy generated under hybridisation conditions

*dG = -1.811 A*

RNAfold data ΔG = -1.66 ΔH = -67.80 ΔS = -197.05 Tm = 70.9°C

TEM! #6

QC of respective probe integrity with respect to hybridisation to respective target sequencse: http://unafold.rna.albany.edu/?q=DINAMelt/Two-state-melting Pass: if alignment is without error, no gaps, no mismatches

| | |
|---|---|
| Target | UCACGCUCGUCGUUUGGUAUGG |
| Probe with stem | Atgctgcat ccataccaaacgacgagcgtga atgcagcaT |
| Two state melting | ΔG = -23.6 ΔH = -214.3 ΔS = -568.1 Tm = 73.6°C |

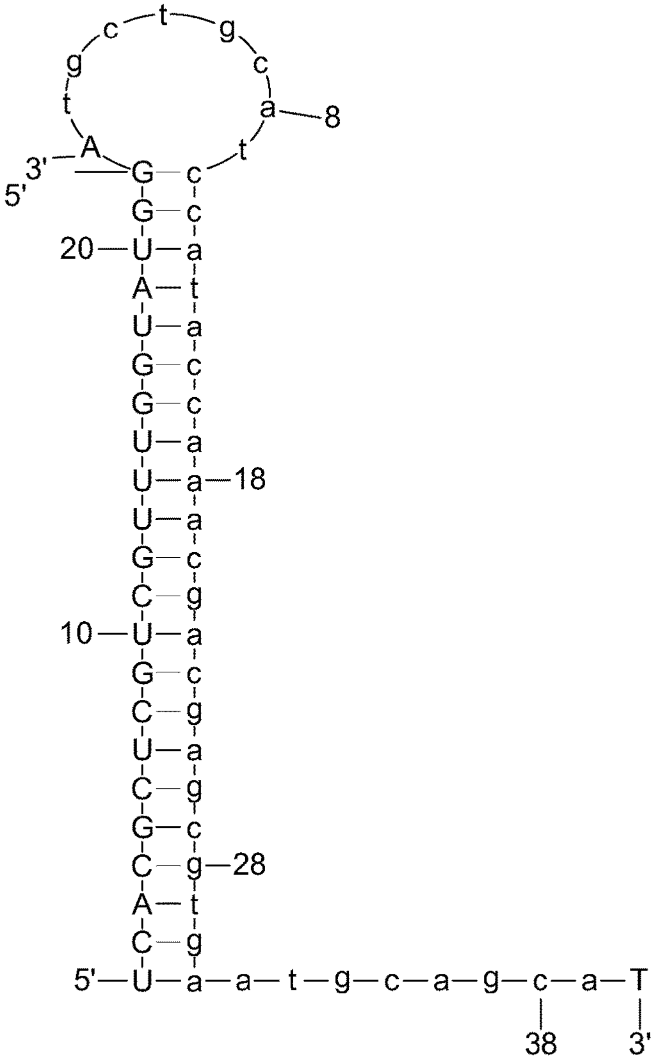

*dG = -23.614 dH = -214.3 A-B*

RNAfold data ΔG = -1.56 ΔH = -67.70 ΔS = -197.05 Tm = 70.4°C

FIG. 5f-1

QC of probe integrity with respect to hairpin loop formation with Quickfold: http://unafold.rna.albany.edu/?q =DINAMelt/Quickfold Pass: Free energy of hairpin loop formation must be negative under hybridisation conditions and <20% of the free energy generated under hybridisation conditions

*dG = -1.556 A*

RNAfold data ΔG = -1.45 ΔH = -64.30 ΔS = -187.25 Tm = 70.2°C

TEM! #7

QC of respective probe integrity with respect to hybridisation to respective target sequencse: http://unafold.rna.albany.edu/?q=DINAMelt/Two-state-melting Pass: if alignment is without error, no gaps, no mismatches

| | |
|---|---|
| Target | CUUCAUUCAGCUCCGGUUCCCA |
| Probe with stem | Atgctgcat tgggaaccggagctgaatgaaga atgcagcaT |
| Two state melting | ΔG = -25.1 ΔH = -227.1 ΔS = -602.0 Tm = 75.2°C |

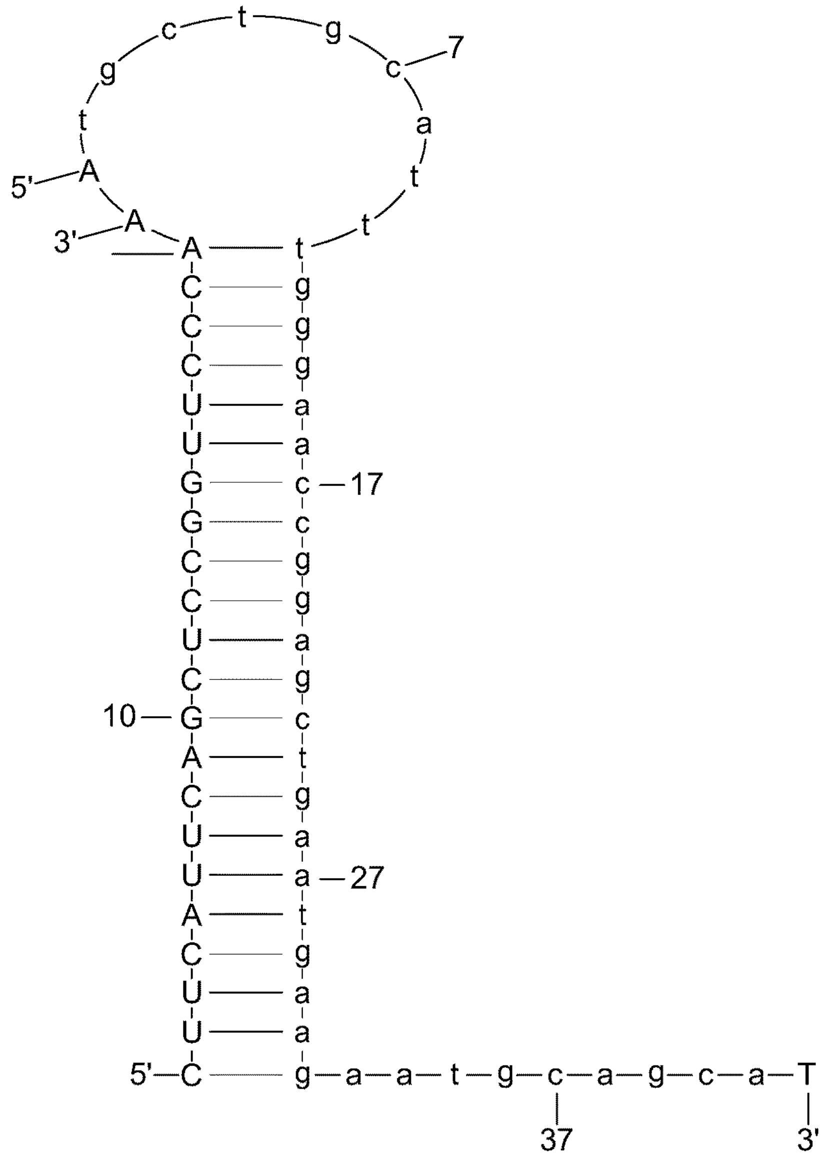

*dG = -25.05 dH = -227.1 A-B*

RNAfold data ΔG = -2.02 ΔH = -74.50 ΔS = -215.94 Tm = 71.9°C

FIG. 5g-1

QC of probe integrity with respect to hairpin loop formation with Quickfold: http://unafold.rna.albany.edu/?q =DINAMelt/Quickfold Pass: Free energy of hairpin loop formation must be negative under hybridisation conditions and <20% of the free energy generated under hybridisation conditions

*dG = -4.238 A*

TEM! #8

QC of respective probe integrity with respect to hybridisation to respective target sequencse: http://unafold.rna.albany.edu/?q=DINAMelt/Two-state-melting Pass: if alignment is without error, no gaps, no mismatches

| | |
|---|---|
| Target | ACGAUCAAGGCGAGUUACAUGAUC |
| Probe with stem | Atgctgcat gatcatgtaactcgccttgatcgt atgcagcaT |
| Two state melting | ΔG = -23.4 ΔH = -230.3 ΔS = -616.5 Tm = 72.5°C |

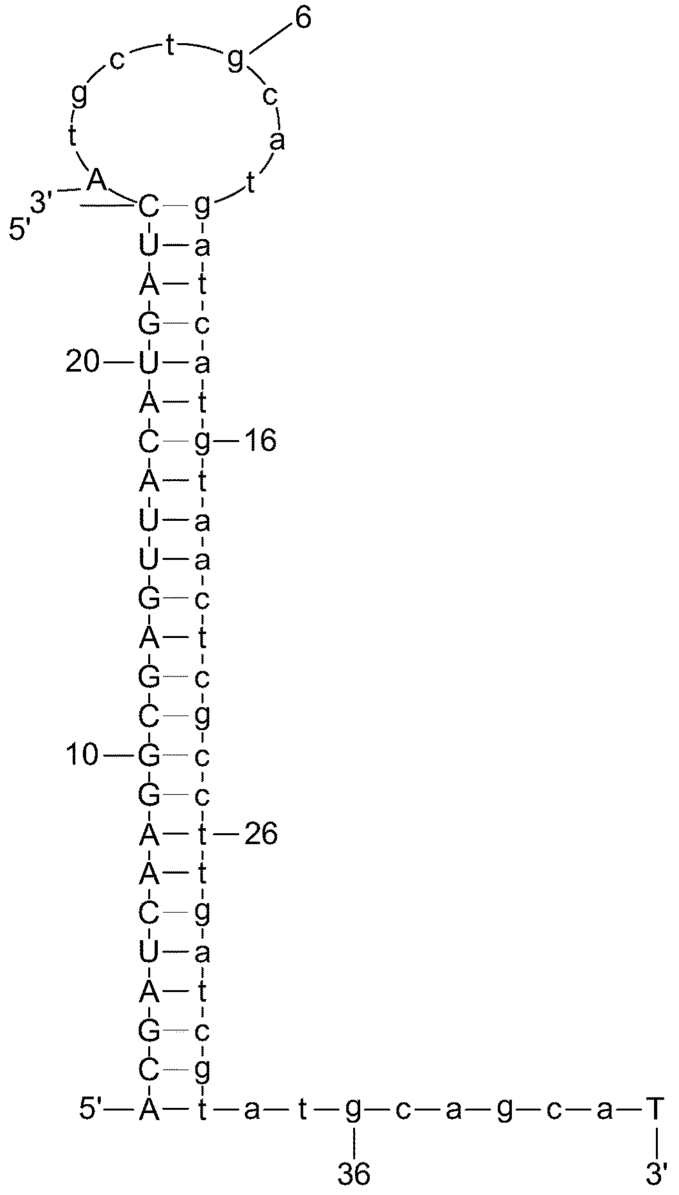

*dG = -23.381 dH = -230.3 A-B*

RNAfold data ΔG = -1.69 ΔH = -97.40 ΔS = -285.12 Tm = 68.4°C

FIG. 5g-3

QC of probe integrity with respect to hairpin loop formation with Quickfold: http://unafold.rna.albany.edu/?q=DINAMelt/Quickfold Pass: Free energy of hairpin loop formation must be negative under hybridisation conditions and <20% of the free energy generated under hybridisation conditions

*dG = -1.691 A*

RNAfold data ΔG = -1.94 ΔH = -80.80 ΔS = -234.95 Tm = 70.8°C

TEM! #9

QC of respective probe integrity with respect to hybridisation to respective target sequencse: http://unafold.rna.albany.edu/?q=DINAMelt/Two-state-melting Pass: if alignment is without error, no gaps, no mismatches

| | |
|---|---|
| Target | CCCCAUGUUGUGCAAAAAAGCGG |
| Probe with stem | Atgctgcat ccgcttttttgcacaacatgggg atgcagcaT |
| Two state melting | ΔG = -23.8 ΔH = -218.4 ΔS = -579.7 Tm = 73.7°C |

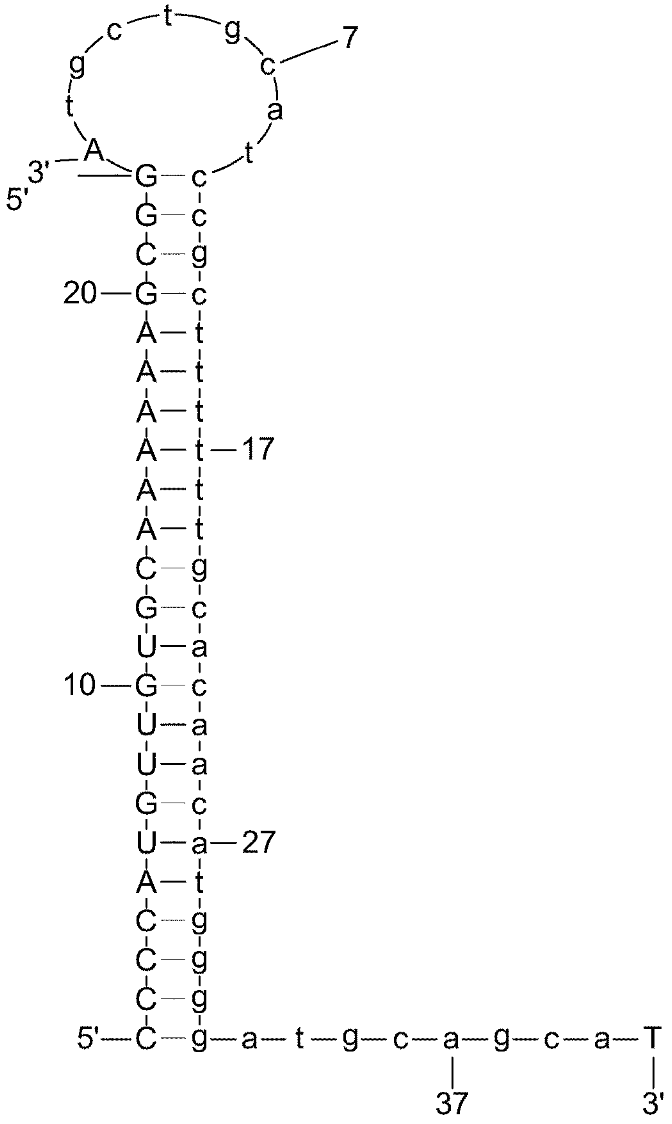

*dG = -23.815 dH = -218.4 A-B*

RNAfold data ΔG = -4.24 ΔH = -84.20 ΔS = -238.22 Tm = 80.3°C

FIG. 5h-1

QC of probe integrity with respect to hairpin loop formation with Quickfold: http://unafold.rna.albany.edu/?q =DINAMelt/Quickfold Pass: Free energy of hairpin loop formation must be negative under hybridisation conditions and <20% of the free energy generated under hybridisation conditions

*dG = -4.238 A*

TEM! #10

QC of respective probe integrity with respect to hybridisation to respective target sequencse: http://unafold.rna.albany.edu/?q=DINAMelt/Two-state-melting Pass: if alignment is without error, no gaps, no mismatches

| | |
|---|---|
| Target | UUAGCUCCUUCGGUCCUCCG |
| Probe with stem | atgctgcat cggaggaccgaaggagctaa atgcagcaT |
| Two state melting | ΔG = -23.4 ΔH = -198.9 ΔS = -523.0 Tm = 74.1°C |

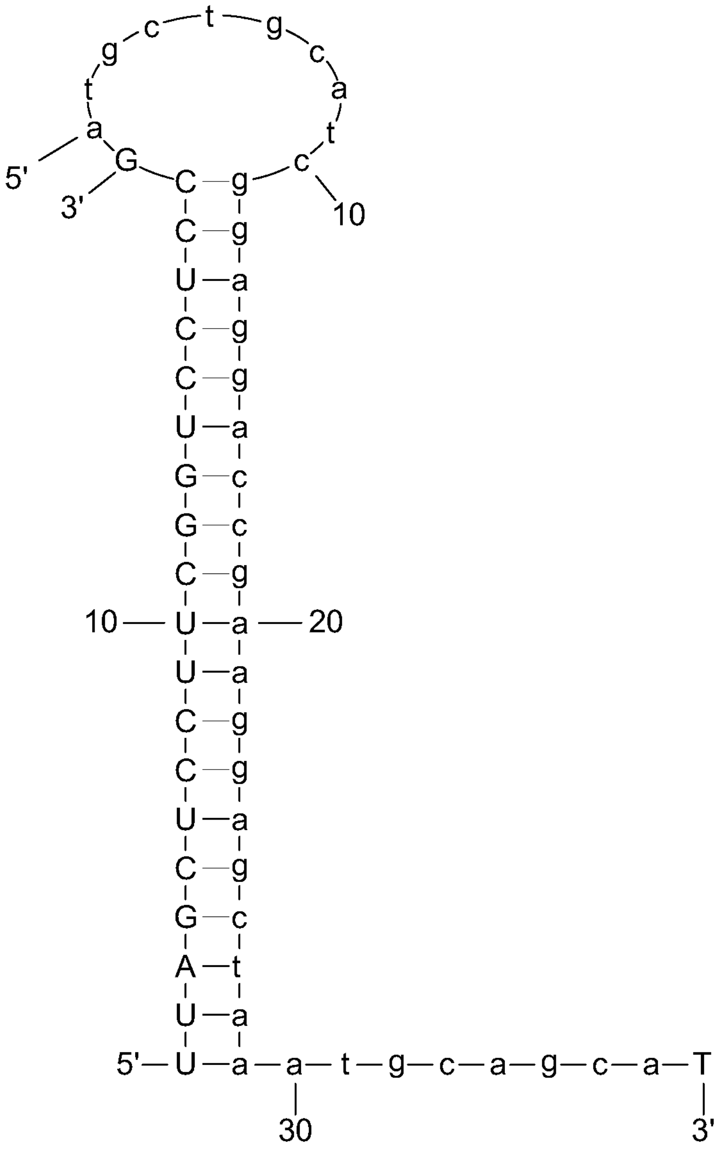

*dG = -23.364 dH = -198.9 A-B*

RNAfold data ΔG = -2.43 ΔH = -86.30 ΔS = -249.87 Tm = 72.2°C

FIG. 5h-3

QC of probe integrity with respect to hairpin loop formation with Quickfold: http://unafold.rna.albany.edu/?q=DINAMelt/Quickfold Pass: Free energy of hairpin loop formation must be negative under hybridisation conditions and <20% of the free energy generated under hybridisation conditions

*dG = -2.431 A*

SEQUENCE LISTING

<160> NUMBER OF SEQ ID NOS: 120

<210> SEQ ID NO 1
<211> LENGTH: 42
<212> TYPE: DNA
<213> ORGANISM: Artificial Sequence
<220> FEATURE:
<223> OTHER INFORMATION: Probe Sequence 3h

<400> SEQUENCE: 1
cgtgaagtct tttggtgcat aaaatgtctg cttttatact aa 42

<210> SEQ ID NO 2
<211> LENGTH: 34
<212> TYPE: DNA
<213> ORGANISM: Artificial Sequence
<220> FEATURE:
<223> OTHER INFORMATION: DNA Target Sequence 3

<400> SEQUENCE: 2
tagtataaaa gcagacattt tatgcaccaa aaga 34

<210> SEQ ID NO 3
<211> LENGTH: 41
<212> TYPE: DNA
<213> ORGANISM: Artificial Sequence
<220> FEATURE:
<223> OTHER INFORMATION: Probe Sequence 4e

<400> SEQUENCE: 3
ccgcatgtcc tgtgggtcct gaaacattgc agttccttca c 41

<210> SEQ ID NO 4
<211> LENGTH: 28
<212> TYPE: DNA
<213> ORGANISM: Artificial Sequence
<220> FEATURE:
<223> OTHER INFORMATION: DNA Target Sequence 4

<400> SEQUENCE: 4
gaactgcaat gtttcaggac ccacagga 28

<210> SEQ ID NO 5
<211> LENGTH: 42
<212> TYPE: DNA
<213> ORGANISM: Artificial Sequence
<220> FEATURE:
<223> OTHER INFORMATION: Probe Sequence 5f

<400> SEQUENCE: 5
ggcgcctgca taactgtggt aactttctgg gtcgccatgc gg 42

<210> SEQ ID NO 6
<211> LENGTH: 28
<212> TYPE: DNA
<213> ORGANISM: Artificial Sequence
<220> FEATURE:
<223> OTHER INFORMATION: DNA Target Sequence 5

<400> SEQUENCE: 6
gcgacccaga aagttaccac agttatgc 28

<210> SEQ ID NO 7
<211> LENGTH: 47
<212> TYPE: DNA
<213> ORGANISM: Artificial Sequence
<220> FEATURE:
<223> OTHER INFORMATION: Probe Sequence 6k

<400> SEQUENCE: 7
accgtcaaat attatatcat gtatagttgt ttgcagctct gggcgcc 47

<210> SEQ ID NO 8
<211> LENGTH: 35
<212> TYPE: DNA
<213> ORGANISM: Artificial Sequence
<220> FEATURE:
<223> OTHER INFORMATION: DNA Target Sequence 6

<400> SEQUENCE: 8
acagagctgc aaacaactat acatgatata atatt 35

<210> SEQ ID NO 9
<211> LENGTH: 45
<212> TYPE: DNA
<213> ORGANISM: Artificial Sequence
<220> FEATURE:
<223> OTHER INFORMATION: Probe Sequence 7h

<400> SEQUENCE: 9
tcccctacag taactgttgc ttgcagtaca cacattcttg acggt 45

<210> SEQ ID NO 10
<211> LENGTH: 31
<212> TYPE: DNA
<213> ORGANISM: Artificial Sequence
<220> FEATURE:
<223> OTHER INFORMATION: DNA Target Sequence 7

<400> SEQUENCE: 10
agaatgtgtg tactgcaagc aacagttact g 31

<210> SEQ ID NO 11
<211> LENGTH: 43
<212> TYPE: DNA
<213> ORGANISM: Artificial Sequence
<220> FEATURE:
<223> OTHER INFORMATION: Probe Sequence 8d

<400> SEQUENCE: 11
ggcttgccga aaagcaaagt catatacctc acgtcgtagg gga 43

<210> SEQ ID NO 12
<211> LENGTH: 29
<212> TYPE: DNA
<213> ORGANISM: Artificial Sequence
<220> FEATURE:
<223> OTHER INFORMATION: DNA Target Sequence 8

<400> SEQUENCE: 12
cgacgtgagg tatatgactt tgcttttcg 29

<210> SEQ ID NO 13
<211> LENGTH: 42
<212> TYPE: DNA
<213> ORGANISM: Artificial Sequence
<220> FEATURE:
<223> OTHER INFORMATION: Probe Sequence 9e

<400> SEQUENCE: 13
atggattccc atctctatat actatgcata aatccgcaag cc 42

<210> SEQ ID NO 14
<211> LENGTH: 35
<212> TYPE: DNA
<213> ORGANISM: Artificial Sequence
<220> FEATURE:
<223> OTHER INFORMATION: DNA Target Sequence 9

<400> SEQUENCE: 14
ggatttatgc atagtatata gagatgggaa tccat 35

<210> SEQ ID NO 15
<211> LENGTH: 43
<212> TYPE: DNA
<213> ORGANISM: Artificial Sequence
<220> FEATURE:
<223> OTHER INFORMATION: Probe 3g

<400> SEQUENCE: 15
tcttttggtg cataaaatgt ctgcttttat actaaaggtc atg 43

<210> SEQ ID NO 16
<211> LENGTH: 43
<212> TYPE: DNA
<213> ORGANISM: Artificial Sequence
<220> FEATURE:
<223> OTHER INFORMATION: Probe 4d

<400> SEQUENCE: 16
tgaccttcct gtgggtcctg aaacattgca gttcaatcaa act 43

<210> SEQ ID NO 17
<211> LENGTH: 46
<212> TYPE: DNA
<213> ORGANISM: Artificial Sequence
<220> FEATURE:
<223> OTHER INFORMATION: Probe 5e

<400> SEQUENCE: 17
agtttgattt gcataactgt ggtaactttc tgggtcgcac tctagt 46

<210> SEQ ID NO 18
<211> LENGTH: 46
<212> TYPE: DNA
<213> ORGANISM: Artificial Sequence
<220> FEATURE:
<223> OTHER INFORMATION: Probe 6j

<400> SEQUENCE: 18
tctagagtaa tattatatca tgtatagttg tttgcagctc tgcatg 46

<210> SEQ ID NO 19
<211> LENGTH: 39
<212> TYPE: DNA
<213> ORGANISM: Artificial Sequence
<220> FEATURE:
<223> OTHER INFORMATION: Probe 7f

<400> SEQUENCE: 19
catgcagtaa ctgttgcttg cagtacacac attcccgcg 39

<210> SEQ ID NO 20
<211> LENGTH: 40
<212> TYPE: DNA
<213> ORGANISM: Artificial Sequence
<220> FEATURE:
<223> OTHER INFORMATION: Probe 8c

<400> SEQUENCE: 20
cgcggcgaaa agcaaagtca tatacctcac gtcgagacgg 40

<210> SEQ ID NO 21
<211> LENGTH: 47
<212> TYPE: DNA
<213> ORGANISM: Artificial Sequence
<220> FEATURE:
<223> OTHER INFORMATION: Probe 9d

<400> SEQUENCE: 21
ccgtctatgg attcccatct ctatatacta tgcataaatc caagggg 47

<210> SEQ ID NO 22
<211> LENGTH: 19
<212> TYPE: DNA
<213> ORGANISM: Artificial Sequence
<220> FEATURE:
<223> OTHER INFORMATION: Probe Sequence 10

<400> SEQUENCE: 22
catttatcac atacagcat 19

<210> SEQ ID NO 23
<211> LENGTH: 19
<212> TYPE: DNA
<213> ORGANISM: Artificial Sequence
<220> FEATURE:
<223> OTHER INFORMATION: DNA Target Sequence 10

<400> SEQUENCE: 23
atgctgtatg tgataaatg 19

<210> SEQ ID NO 24
<211> LENGTH: 41
<212> TYPE: DNA
<213> ORGANISM: Artificial Sequence
<220> FEATURE:
<223> OTHER INFORMATION: Probe Sequence c1b

<400> SEQUENCE: 24
acgcgcataa agtgtatgtc gtatacctaa gggtagagat a 41

<210> SEQ ID NO 25
<211> LENGTH: 34
<212> TYPE: DNA
<213> ORGANISM: Artificial Sequence
<220> FEATURE:
<223> OTHER INFORMATION: DNA Target Sequence c1b

<400> SEQUENCE: 25
tatctctacc cttaggtata cgacatacac tatt 34

<210> SEQ ID NO 26
<211> LENGTH: 52
<212> TYPE: DNA
<213> ORGANISM: Artificial Sequence
<220> FEATURE:
<223> OTHER INFORMATION: Probe Sequence c2b

<400> SEQUENCE: 26
ggtactgcat attgatacgt atttagggct tttcgtttca gtatatgcgc gt 52

<210> SEQ ID NO 27

<211> LENGTH: 37
<212> TYPE: DNA
<213> ORGANISM: Artificial Sequence
<220> FEATURE:
<223> OTHER INFORMATION: DNA Target Sequence c2b

<400> SEQUENCE: 27
catatactga aacgaaaagc cctaaatacg tatcata 37

<210> SEQ ID NO 28
<211> LENGTH: 47
<212> TYPE: DNA
<213> ORGANISM: Artificial Sequence
<220> FEATURE:
<223> OTHER INFORMATION: Probe Sequence c3b

<400> SEQUENCE: 28
gtgggtacag tgcagcgtca ttgacaacga acgtcatgtg cagtacc 47

<210> SEQ ID NO 29
<211> LENGTH: 31
<212> TYPE: DNA
<213> ORGANISM: Artificial Sequence
<220> FEATURE:
<223> OTHER INFORMATION: DNA Target Sequence c3b

<400> SEQUENCE: 29
catgacgttc gttgtcaatg acgctgcact c 31

<210> SEQ ID NO 30
<211> LENGTH: 53
<212> TYPE: DNA
<213> ORGANISM: Artificial Sequence
<220> FEATURE:
<223> OTHER INFORMATION: Probe Sequence c4b

<400> SEQUENCE: 30
ccagggagtg tgtaagatta taatatagta catatcaaca aacgtgtacc cac 53

<210> SEQ ID NO 31
<211> LENGTH: 37
<212> TYPE: DNA
<213> ORGANISM: Artificial Sequence
<220> FEATURE:
<223> OTHER INFORMATION: DNA Target Sequence c4b

<400> SEQUENCE: 31
acgtttgttg atatgtacta tattataatc ttacaca 37

<210> SEQ ID NO 32
<211> LENGTH: 45
<212> TYPE: DNA
<213> ORGANISM: Artificial Sequence
<220> FEATURE:
<223> OTHER INFORMATION: Probe Sequence c5b

<400> SEQUENCE: 32
ccacggtacc gagacacgta ttgacaccat tgaaagactc cctgg 45

<210> SEQ ID NO 33
<211> LENGTH: 28
<212> TYPE: DNA
<213> ORGANISM: Artificial Sequence
<220> FEATURE:
<223> OTHER INFORMATION: DNA Target Sequence c5b

<400> SEQUENCE: 33
tctttcaatg gtgtcaatac gtgtctcg 28

<210> SEQ ID NO 34
<211> LENGTH: 47
<212> TYPE: DNA
<213> ORGANISM: Artificial Sequence
<220> FEATURE:
<223> OTHER INFORMATION: Probe Sequence c6b

<400> SEQUENCE: 34
ggtagggccc agcgaggaca cccaggactt tgtaagctgt accgtgg 47

<210> SEQ ID NO 35
<211> LENGTH: 31
<212> TYPE: DNA
<213> ORGANISM: Artificial Sequence
<220> FEATURE:
<223> OTHER INFORMATION: DNA Target Sequence c6b

<400> SEQUENCE: 35
acgttacaaa gtcctgggtg tcctcgctgg g 31

<210> SEQ ID NO 36
<211> LENGTH: 39
<212> TYPE: DNA
<213> ORGANISM: Artificial Sequence
<220> FEATURE:
<223> OTHER INFORMATION: Probe Sequence c7b

<400> SEQUENCE: 36
caagagaaaa ccacgtattt tacagacgaa aaccctacc 39

<210> SEQ ID NO 37
<211> LENGTH: 32
<212> TYPE: DNA
<213> ORGANISM: Artificial Sequence
<220> FEATURE:
<223> OTHER INFORMATION: DNA Target Sequence c7b

<400> SEQUENCE: 37
ttttcgtctg taaaatacgt ggttttctct tg 32

<210> SEQ ID NO 38
<211> LENGTH: 17
<212> TYPE: DNA
<213> ORGANISM: Artificial Sequence
<220> FEATURE:
<223> OTHER INFORMATION: Half Target 3a

<400> SEQUENCE: 38
tagtataaaa gcagaca 17

<210> SEQ ID NO 39
<211> LENGTH: 17
<212> TYPE: DNA
<213> ORGANISM: Artificial Sequence
<220> FEATURE:
<223> OTHER INFORMATION: Half Probe 3a'

<400> SEQUENCE: 39
tgtctgcttt tatacta 17

<210> SEQ ID NO 40
<211> LENGTH: 17
<212> TYPE: DNA

<213> ORGANISM: Artificial Sequence
<220> FEATURE:
<223> OTHER INFORMATION: Half Target 3b

<400> SEQUENCE: 40
ttttatgcac caaaaga 17

<210> SEQ ID NO 41
<211> LENGTH: 17
<212> TYPE: DNA
<213> ORGANISM: Artificial Sequence
<220> FEATURE:
<223> OTHER INFORMATION: Half Probe 3b'

<400> SEQUENCE: 41
tcttttggtg cataaaa 17

<210> SEQ ID NO 42
<211> LENGTH: 16
<212> TYPE: DNA
<213> ORGANISM: Artificial Sequence
<220> FEATURE:
<223> OTHER INFORMATION: Half Target 4a

<400> SEQUENCE: 42
gaactgcaat gtttca 16

<210> SEQ ID NO 43
<211> LENGTH: 16
<212> TYPE: DNA
<213> ORGANISM: Artificial Sequence
<220> FEATURE:
<223> OTHER INFORMATION: Half Probe 4a'

<400> SEQUENCE: 43
tgaaacattg cagttc 16

<210> SEQ ID NO 44
<211> LENGTH: 12
<212> TYPE: DNA
<213> ORGANISM: Artificial Sequence
<220> FEATURE:
<223> OTHER INFORMATION: Half Target 4b

<400> SEQUENCE: 44
ggacccacag ga 12

<210> SEQ ID NO 45
<211> LENGTH: 12
<212> TYPE: DNA
<213> ORGANISM: Artificial Sequence
<220> FEATURE:
<223> OTHER INFORMATION: Half Probe 4b'

<400> SEQUENCE: 45
tcctgtgggt cc 12

<210> SEQ ID NO 46
<211> LENGTH: 12
<212> TYPE: DNA
<213> ORGANISM: Artificial Sequence
<220> FEATURE:
<223> OTHER INFORMATION: Half Target 5a

<400> SEQUENCE: 46
gcgacccaga aa 12

<210> SEQ ID NO 47
<211> LENGTH: 12
<212> TYPE: DNA
<213> ORGANISM: Artificial Sequence
<220> FEATURE:
<223> OTHER INFORMATION: Half Probe 5a'

<400> SEQUENCE: 47
tttctgggtc gc 12

<210> SEQ ID NO 48
<211> LENGTH: 16
<212> TYPE: DNA
<213> ORGANISM: Artificial Sequence
<220> FEATURE:
<223> OTHER INFORMATION: Half Target 5b

<400> SEQUENCE: 48
gttaccacag ttatgc 16

<210> SEQ ID NO 49
<211> LENGTH: 16
<212> TYPE: DNA
<213> ORGANISM: Artificial Sequence
<220> FEATURE:
<223> OTHER INFORMATION: Half Probe 5b'

<400> SEQUENCE: 49
gcataactgt ggtaac 16

<210> SEQ ID NO 50
<211> LENGTH: 14
<212> TYPE: DNA
<213> ORGANISM: Artificial Sequence
<220> FEATURE:
<223> OTHER INFORMATION: Half Target 6a

<400> SEQUENCE: 50
acagagctgc aaac 14

<210> SEQ ID NO 51
<211> LENGTH: 14
<212> TYPE: DNA
<213> ORGANISM: Artificial Sequence
<220> FEATURE:
<223> OTHER INFORMATION: Half Probe 6a'

<400> SEQUENCE: 51
gtttgcagct ctgt 14

<210> SEQ ID NO 52
<211> LENGTH: 21
<212> TYPE: DNA
<213> ORGANISM: Artificial Sequence
<220> FEATURE:
<223> OTHER INFORMATION: Half Target 6b

<400> SEQUENCE: 52
aactatacat gatataatat t 21

<210> SEQ ID NO 53
<211> LENGTH: 21
<212> TYPE: DNA
<213> ORGANISM: Artificial Sequence
<220> FEATURE:

<223> OTHER INFORMATION: Half Probe 6b'

<400> SEQUENCE: 53
aatattatat catgtatagt t 21

<210> SEQ ID NO 54
<211> LENGTH: 15
<212> TYPE: DNA
<213> ORGANISM: Artificial Sequence
<220> FEATURE:
<223> OTHER INFORMATION: Half Target 7a

<400> SEQUENCE: 54
agaatgtgtg tactg 15

<210> SEQ ID NO 55
<211> LENGTH: 14
<212> TYPE: DNA
<213> ORGANISM: Artificial Sequence
<220> FEATURE:
<223> OTHER INFORMATION: Half Probe 7a'

<400> SEQUENCE: 55
cagtacacac attc 14

<210> SEQ ID NO 56
<211> LENGTH: 16
<212> TYPE: DNA
<213> ORGANISM: Artificial Sequence
<220> FEATURE:
<223> OTHER INFORMATION: Half Target 7b

<400> SEQUENCE: 56
caagcaacag ttactg 16

<210> SEQ ID NO 57
<211> LENGTH: 16
<212> TYPE: DNA
<213> ORGANISM: Artificial Sequence
<220> FEATURE:
<223> OTHER INFORMATION: Half Probe 7b'

<400> SEQUENCE: 57
cagtaactgt tgcttg 16

<210> SEQ ID NO 58
<211> LENGTH: 14
<212> TYPE: DNA
<213> ORGANISM: Artificial Sequence
<220> FEATURE:
<223> OTHER INFORMATION: Half Target 8a

<400> SEQUENCE: 58
cgacgtgagg tata 14

<210> SEQ ID NO 59
<211> LENGTH: 14
<212> TYPE: DNA
<213> ORGANISM: Artificial Sequence
<220> FEATURE:
<223> OTHER INFORMATION: Half Probe 8a'

<400> SEQUENCE: 59
tatacctcac gtcg 14

<210> SEQ ID NO 60
<211> LENGTH: 15
<212> TYPE: DNA
<213> ORGANISM: Artificial Sequence
<220> FEATURE:
<223> OTHER INFORMATION: Half Target 8b

<400> SEQUENCE: 60
tgactttgct tttcg 15

<210> SEQ ID NO 61
<211> LENGTH: 15
<212> TYPE: DNA
<213> ORGANISM: Artificial Sequence
<220> FEATURE:
<223> OTHER INFORMATION: Half Probe 8b'

<400> SEQUENCE: 61
cgaaaagcaa agtca 15

<210> SEQ ID NO 62
<211> LENGTH: 18
<212> TYPE: DNA
<213> ORGANISM: Artificial Sequence
<220> FEATURE:
<223> OTHER INFORMATION: Half Target 9a

<400> SEQUENCE: 62
ggatttatgc atagtata 18

<210> SEQ ID NO 63
<211> LENGTH: 18
<212> TYPE: DNA
<213> ORGANISM: Artificial Sequence
<220> FEATURE:
<223> OTHER INFORMATION: Half Probe 9a'

<400> SEQUENCE: 63
tatactatgc ataaatcc 18

<210> SEQ ID NO 64
<211> LENGTH: 17
<212> TYPE: DNA
<213> ORGANISM: Artificial Sequence
<220> FEATURE:
<223> OTHER INFORMATION: Half Target 9b

<400> SEQUENCE: 64
tagagatggg aatccat 17

<210> SEQ ID NO 65
<211> LENGTH: 17
<212> TYPE: DNA
<213> ORGANISM: Artificial Sequence
<220> FEATURE:
<223> OTHER INFORMATION: Half Probe 9b'

<400> SEQUENCE: 65
atggattccc atctcta 17

<210> SEQ ID NO 66
<211> LENGTH: 18
<212> TYPE: DNA
<213> ORGANISM: Artificial Sequence
<220> FEATURE:
<223> OTHER INFORMATION: Half Target 10a

<400> SEQUENCE: 66
atgctgtatg tgataaat 18

<210> SEQ ID NO 67
<211> LENGTH: 33
<212> TYPE: DNA
<213> ORGANISM: Artificial Sequence
<220> FEATURE:
<223> OTHER INFORMATION: Resulting cDNA Target (3b+4a)

<400> SEQUENCE: 67
ttttatgcac caaaagagaa ctgcaatgtt tca 33

<210> SEQ ID NO 68
<211> LENGTH: 33
<212> TYPE: DNA
<213> ORGANISM: Artificial Sequence
<220> FEATURE:
<223> OTHER INFORMATION: Resulting cDNA Probe 7'

<400> SEQUENCE: 68
tgaaacattg cagttctctt ttggtgcata aaa 33

<210> SEQ ID NO 69
<211> LENGTH: 24
<212> TYPE: DNA
<213> ORGANISM: Artificial Sequence
<220> FEATURE:
<223> OTHER INFORMATION: Resulting cDNA Target (4b+5a)

<400> SEQUENCE: 69
ggacccacag gagcgaccca gaaa 24

<210> SEQ ID NO 70
<211> LENGTH: 24
<212> TYPE: DNA
<213> ORGANISM: Artificial Sequence
<220> FEATURE:
<223> OTHER INFORMATION: Resulting cDNA Probe 6'

<400> SEQUENCE: 70
tttctgggtc gctcctgtgg gtcc 24

<210> SEQ ID NO 71
<211> LENGTH: 30
<212> TYPE: DNA
<213> ORGANISM: Artificial Sequence
<220> FEATURE:
<223> OTHER INFORMATION: Resulting cDNA Target (5b+6a)

<400> SEQUENCE: 71
gttaccacag ttatgcacag agctgcaaac 30

<210> SEQ ID NO 72
<211> LENGTH: 30
<212> TYPE: DNA
<213> ORGANISM: Artificial Sequence
<220> FEATURE:
<223> OTHER INFORMATION: Resulting cDNA Probe 5'

<400> SEQUENCE: 72
gtttgcagct ctgtgcataa ctgtggtaac 30

<210> SEQ ID NO 73
<211> LENGTH: 36

<212> TYPE: DNA
<213> ORGANISM: Artificial Sequence
<220> FEATURE:
<223> OTHER INFORMATION: Resulting cDNA Target (6b+7a)

<400> SEQUENCE: 73
aactatacat gatataatat tagaatgtgt gtactg 36

<210> SEQ ID NO 74
<211> LENGTH: 36
<212> TYPE: DNA
<213> ORGANISM: Artificial Sequence
<220> FEATURE:
<223> OTHER INFORMATION: Resulting cDNA Probe 4'

<400> SEQUENCE: 74
cagtacacac attctaatat tatatcatgt atagtt 36

<210> SEQ ID NO 75
<211> LENGTH: 30
<212> TYPE: DNA
<213> ORGANISM: Artificial Sequence
<220> FEATURE:
<223> OTHER INFORMATION: Resulting cDNA Target (7b+8a)

<400> SEQUENCE: 75
caagcaacag ttactgcgac gtgaggtata 30

<210> SEQ ID NO 76
<211> LENGTH: 30
<212> TYPE: DNA
<213> ORGANISM: Artificial Sequence
<220> FEATURE:
<223> OTHER INFORMATION: Resulting cDNA Probe 3'

<400> SEQUENCE: 76
tatacctcac gtcgcagtaa ctgttgcttg 30

<210> SEQ ID NO 77
<211> LENGTH: 33
<212> TYPE: DNA
<213> ORGANISM: Artificial Sequence
<220> FEATURE:
<223> OTHER INFORMATION: Resulting cDNA Target (8b+9a)

<400> SEQUENCE: 77
tgactttgct tttcgggatt tatgcatagt ata 33

<210> SEQ ID NO 78
<211> LENGTH: 33
<212> TYPE: DNA
<213> ORGANISM: Artificial Sequence
<220> FEATURE:
<223> OTHER INFORMATION: Resulting cDNA Probe 2'

<400> SEQUENCE: 78
tatactatgc ataaatcccg aaaagcaaag tca 33

<210> SEQ ID NO 79
<211> LENGTH: 35
<212> TYPE: DNA
<213> ORGANISM: Artificial Sequence
<220> FEATURE:
<223> OTHER INFORMATION: Resulting cDNA Target (9b+10a)

<400> SEQUENCE: 79
tagagatggg aatccatatg ctgtatgtga taaat 35

<210> SEQ ID NO 80
<211> LENGTH: 35
<212> TYPE: DNA
<213> ORGANISM: Artificial Sequence
<220> FEATURE:
<223> OTHER INFORMATION: Resulting cDNA Probe 1'

<400> SEQUENCE: 80
atttatcaca tacagcatat ggattcccat ctcta 35

<210> SEQ ID NO 81
<211> LENGTH: 39
<212> TYPE: DNA
<213> ORGANISM: Artificial Sequence
<220> FEATURE:
<223> OTHER INFORMATION: Resulting cDNA Probes 7' with helping stems

<400> SEQUENCE: 81
accctgtgaa acattgcagt tctcttttgg tgcataaaa 39

<210> SEQ ID NO 82
<211> LENGTH: 38
<212> TYPE: DNA
<213> ORGANISM: Artificial Sequence
<220> FEATURE:
<223> OTHER INFORMATION: resulting cDNA Probes 6' with helping stems

<400> SEQUENCE: 82
tttgagggtt tctgggtcgc tcctgtgggt cccagggt 38

<210> SEQ ID NO 83
<211> LENGTH: 44
<212> TYPE: DNA
<213> ORGANISM: Artificial Sequence
<220> FEATURE:
<223> OTHER INFORMATION: Resulting cDNA Probes 5' with helping stems

<400> SEQUENCE: 83
ggatgtgttt gcagctctgt gcataactgt ggtaacccct caaa 44

<210> SEQ ID NO 84
<211> LENGTH: 47
<212> TYPE: DNA
<213> ORGANISM: Artificial Sequence
<220> FEATURE:
<223> OTHER INFORMATION: Resulting cDNA Probes 4' with helping stems

<400> SEQUENCE: 84
cgtcacagta cacacattct aatattatat catgtatagt tacccat 47

<210> SEQ ID NO 85
<211> LENGTH: 39
<212> TYPE: DNA
<213> ORGANISM: Artificial Sequence
<220> FEATURE:
<223> OTHER INFORMATION: Resulting cDNA Probes 3' with helping stems

<400> SEQUENCE: 85
cgcgtatacc tcacgtcgca gtaactgttg cttgtgacg 39

<210> SEQ ID NO 86
<211> LENGTH: 47
<212> TYPE: DNA
<213> ORGANISM: Artificial Sequence
<220> FEATURE:
<223> OTHER INFORMATION: Resulting cDNA Probes 2' with helping stems

<400> SEQUENCE: 86
acgcgtatac tatgcataaa tcccgaaaag caaagtcacg cgggttc 47

<210> SEQ ID NO 87
<211> LENGTH: 40
<212> TYPE: DNA
<213> ORGANISM: Artificial Sequence
<220> FEATURE:
<223> OTHER INFORMATION: Resulting cDNA Probes 1' with helping stems

<400> SEQUENCE: 87
atttatcaca tacagcatat ggattcccat ctctacgcgt 40

<210> SEQ ID NO 88
<211> LENGTH: 21
<212> TYPE: DNA
<213> ORGANISM: Artificial Sequence
<220> FEATURE:
<223> OTHER INFORMATION: Staaur Probe Sequence

<400> SEQUENCE: 88
gcaagcttct cgtccgttcg c 21

<210> SEQ ID NO 89
<211> LENGTH: 21
<212> TYPE: DNA
<213> ORGANISM: Artificial Sequence
<220> FEATURE:
<223> OTHER INFORMATION: Staaur Target Sequence

<400> SEQUENCE: 89
gcgaacggac gagaagcttg c 21

<210> SEQ ID NO 90
<211> LENGTH: 22
<212> TYPE: RNA
<213> ORGANISM: Artificial Sequence
<220> FEATURE:
<223> OTHER INFORMATION: ?-lactamase gene TEM-1 #1 target

<400> SEQUENCE: 90
ugcugcaacu uuauccgccu cc 22

<210> SEQ ID NO 91
<211> LENGTH: 40
<212> TYPE: DNA
<213> ORGANISM: Artificial Sequence
<220> FEATURE:
<223> OTHER INFORMATION: ?-lactamase gene TEM-1 #1 probe with stem

<400> SEQUENCE: 91
atgctgcatg gaggcggata aagttgcagc aatgcagcat 40

<210> SEQ ID NO 92
<211> LENGTH: 25
<212> TYPE: RNA
<213> ORGANISM: Artificial Sequence
<220> FEATURE:
<223> OTHER INFORMATION: ?-lactamase gene TEM-1 #2 target

<400> SEQUENCE: 92
auccagucua uuaauuguug ccggg 25

<210> SEQ ID NO 93
<211> LENGTH: 43
<212> TYPE: DNA
<213> ORGANISM: Artificial Sequence
<220> FEATURE:
<223> OTHER INFORMATION: ?-lactamase gene TEM-1 #2 probe with stem

<400> SEQUENCE: 93
atgctgcatc ccggcaacaa ttaatagact ggatatgcag cat 43

<210> SEQ ID NO 94
<211> LENGTH: 24
<212> TYPE: RNA
<213> ORGANISM: Artificial Sequence
<220> FEATURE:
<223> OTHER INFORMATION: ?-lactamase gene TEM-1 #3 target

<400> SEQUENCE: 94
aagcuagagu aaguaguucg ccag 24

<210> SEQ ID NO 95
<211> LENGTH: 42
<212> TYPE: DNA
<213> ORGANISM: Artificial Sequence
<220> FEATURE:
<223> OTHER INFORMATION: ?-lactamase gene TEM-1 #3 probe with stem

<400> SEQUENCE: 95
atgctgcatc tggcgaacta cttactctag cttatgcagc at 42

<210> SEQ ID NO 96
<211> LENGTH: 26
<212> TYPE: RNA
<213> ORGANISM: Artificial Sequence
<220> FEATURE:
<223> OTHER INFORMATION: ?-lactamase gene TEM-1 #4 target

<400> SEQUENCE: 96
uuaauaguuu gcgcaacguu guugcc 26

<210> SEQ ID NO 97
<211> LENGTH: 44
<212> TYPE: DNA
<213> ORGANISM: Artificial Sequence
<220> FEATURE:
<223> OTHER INFORMATION: ?-lactamase gene TEM-1 #4 probe with stem

<400> SEQUENCE: 97
atgctgcatg gcaacaacgt tgcgcaaact attaaatgca gcat 44

<210> SEQ ID NO 98
<211> LENGTH: 21
<212> TYPE: RNA
<213> ORGANISM: Artificial Sequence
<220> FEATURE:
<223> OTHER INFORMATION: ?-lactamase gene TEM-1 #5 target

<400> SEQUENCE: 98
auugcugcag gcaucguggu g 21

<210> SEQ ID NO 99
<211> LENGTH: 39
<212> TYPE: DNA
<213> ORGANISM: Artificial Sequence
<220> FEATURE:
<223> OTHER INFORMATION: ?-lactamase gene TEM-1 #5 probe with stem

<400> SEQUENCE: 99
atgctgcatc accacgatgc ctgcagcaat atgcagcat 39

<210> SEQ ID NO 100
<211> LENGTH: 22
<212> TYPE: RNA
<213> ORGANISM: Artificial Sequence
<220> FEATURE:
<223> OTHER INFORMATION: ?-lactamase gene TEM-1 #6 target

<400> SEQUENCE: 100
ucacgcucgu cguuugguau gg 22

<210> SEQ ID NO 101
<211> LENGTH: 40
<212> TYPE: DNA
<213> ORGANISM: Artificial Sequence
<220> FEATURE:
<223> OTHER INFORMATION: ?-lactamase gene TEM-1 #6 probe with stem

<400> SEQUENCE: 101
atgctgcatc cataccaaac gacgagcgtg aatgcagcat 40

<210> SEQ ID NO 102
<211> LENGTH: 22
<212> TYPE: RNA
<213> ORGANISM: Artificial Sequence
<220> FEATURE:
<223> OTHER INFORMATION: ?-lactamase gene TEM-1 #7 target

<400> SEQUENCE: 102
cuucauucag cuccgguucc ca 22

<210> SEQ ID NO 103
<211> LENGTH: 41
<212> TYPE: DNA
<213> ORGANISM: Artificial Sequence
<220> FEATURE:
<223> OTHER INFORMATION: ?-lactamase gene TEM-1 #7 probe with stem

<400> SEQUENCE: 103
atgctgcatt gggaaccgga gctgaatgaa gaatgcagca t 41

<210> SEQ ID NO 104
<211> LENGTH: 24
<212> TYPE: RNA
<213> ORGANISM: Artificial Sequence
<220> FEATURE:
<223> OTHER INFORMATION: ?-lactamase gene TEM-1 #8 target

<400> SEQUENCE: 104
acgaucaagg cgaguuacau gauc 24

<210> SEQ ID NO 105
<211> LENGTH: 42
<212> TYPE: DNA
<213> ORGANISM: Artificial Sequence
<220> FEATURE:
<223> OTHER INFORMATION: ?-lactamase gene TEM-1 #8 probe with stem

<400> SEQUENCE: 105
atgctgcatg atcatgtaac tcgccttgat cgtatgcagc at 42

<210> SEQ ID NO 106

<211> LENGTH: 23
<212> TYPE: RNA
<213> ORGANISM: Artificial Sequence
<220> FEATURE:
<223> OTHER INFORMATION: ?-lactamase gene TEM-1 #9 target

<400> SEQUENCE: 106
ccccauguug ugcaaaaaag cgg 23

<210> SEQ ID NO 107
<211> LENGTH: 41
<212> TYPE: DNA
<213> ORGANISM: Artificial Sequence
<220> FEATURE:
<223> OTHER INFORMATION: ?-lactamase gene TEM-1 #9 probe with stem

<400> SEQUENCE: 107
atgctgcatc cgcttttttg cacaacatgg ggatgcagca t 41

<210> SEQ ID NO 108
<211> LENGTH: 20
<212> TYPE: RNA
<213> ORGANISM: Artificial Sequence
<220> FEATURE:
<223> OTHER INFORMATION: ?-lactamase gene TEM-1 #10 target

<400> SEQUENCE: 108
uuagcuccuu cgguccuccg 20

<210> SEQ ID NO 109
<211> LENGTH: 38
<212> TYPE: DNA
<213> ORGANISM: Artificial Sequence
<220> FEATURE:
<223> OTHER INFORMATION: ?-lactamase gene TEM-1 #10 probe with stem

<400> SEQUENCE: 109
atgctgcatc ggaggaccga aggagctaaa tgcagcat 38

<210> SEQ ID NO 110
<211> LENGTH: 34
<212> TYPE: DNA
<213> ORGANISM: Artificial Sequence
<220> FEATURE:
<223> OTHER INFORMATION: Probe c1

<400> SEQUENCE: 110
taaagtgtat gtcgtatacc taagggtaga gata 34

<210> SEQ ID NO 111
<211> LENGTH: 32
<212> TYPE: DNA
<213> ORGANISM: Artificial Sequence
<220> FEATURE:
<223> OTHER INFORMATION: Probe c2

<400> SEQUENCE: 111
acgtatttag ggcttttcgt ttcagtatat gg 32

<210> SEQ ID NO 112
<211> LENGTH: 28
<212> TYPE: DNA
<213> ORGANISM: Artificial Sequence
<220> FEATURE:
<223> OTHER INFORMATION: Probe c3

<400> SEQUENCE: 112
gtcattgaca acgaacgtca tgtgtgta 28

<210> SEQ ID NO 113
<211> LENGTH: 41
<212> TYPE: DNA
<213> ORGANISM: Artificial Sequence
<220> FEATURE:
<223> OTHER INFORMATION: Probe c4

<400> SEQUENCE: 113
tgtgtgtaag attataatat agtacatatc aacaaacgtc g 41

<210> SEQ ID NO 114
<211> LENGTH: 29
<212> TYPE: DNA
<213> ORGANISM: Artificial Sequence
<220> FEATURE:
<223> OTHER INFORMATION: Probe c5

<400> SEQUENCE: 114
agacacgtat tgacaccatt gaaagaccc 29

<210> SEQ ID NO 115
<211> LENGTH: 31
<212> TYPE: DNA
<213> ORGANISM: Artificial Sequence
<220> FEATURE:
<223> OTHER INFORMATION: Probe c6

<400> SEQUENCE: 115
agcgaggaca cccaggactt tgtaacaaga g 31

<210> SEQ ID NO 116
<211> LENGTH: 33
<212> TYPE: DNA
<213> ORGANISM: Artificial Sequence
<220> FEATURE:
<223> OTHER INFORMATION: Probe c7

<400> SEQUENCE: 116
aaaaccacgt attttacaga cgaaaatatg att 33

<210> SEQ ID NO 117
<211> LENGTH: 37
<212> TYPE: DNA
<213> ORGANISM: Artificial Sequence
<220> FEATURE:
<223> OTHER INFORMATION: E. coli probe 5'-1 with stem: Atto-465

<400> SEQUENCE: 117
actcagtatc tcgggagaag gcacgctgat actgagt 37

<210> SEQ ID NO 118
<211> LENGTH: 41
<212> TYPE: DNA
<213> ORGANISM: Artificial Sequence
<220> FEATURE:
<223> OTHER INFORMATION: E. coli probe with stem: Atto-514

<400> SEQUENCE: 118
actcagtacg caagtcgctt cacctacata tcgtactgag t 41

<210> SEQ ID NO 119
<211> LENGTH: 41
<212> TYPE: DNA

-continued

```
<213> ORGANISM: Artificial Sequence
<220> FEATURE:
<223> OTHER INFORMATION: E. coli probe 3'+1 with stem: Atto-465

<400> SEQUENCE: 119

actcagtact ggagctgaaa tcagtcgaag gagtactgag t                  41


<210> SEQ ID NO 120
<211> LENGTH: 64
<212> TYPE: DNA
<213> ORGANISM: Escherichia coli

<400> SEQUENCE: 120

agcgtgcctt ctcccgagat atgtaggtga agcgacttgc tccttcgact gatttcagct     60

ccac                                                                  64
```

IN-SITU CONCATENATION OF OLIGO-NUCLEOTIDE PROBES FOR TARGET DETECTION

CROSS-REFERENCE TO RELATED APPLICATIONS

This application is a national stage application, filed under 35 U.S.C. § 371, of international application No. PCT/GB2020/051444, filed Jun. 15, 2020 and published on Dec. 17, 2020 as WO 2020/249982, which claims the benefit of GB Application No. 1908481.3, filed Jun. 13, 2019, entitled "In-situ concatenation of oligo-nucleotide probes for target detection."

FIELD OF THE INVENTION

This invention relates to the in-situ concatenation of oligo-nucleotide probes for the detection of target sequences

SEQUENCE LISTING

The instant application contains a Sequence Listing which has been filed electronically in ASCII format and is hereby incorporated by reference in its entirety. Said ASCII copy, created on Nov. 30, 2021, is named BN00023_0030_SL.txt and is 24 KB in size.

BACKGROUND OF THE INVENTION

Personalised medicine, cancer diagnostics, rapid microbiological resistance testing, and microbial identification require a plurality of DNA/RNA-based information, which are derived from body fluids, tissue samples and swabs. The information, present in very low concentrations or single copies, is required in a timely manner directly from specimens. Equally, microbial infections require immediate identification of the culprit, including vital information for the targeted treatment of individuals, where current state of the art methodology fails to give clinicians immediate information in time to start therapeutic regimens. Even in non-clinical environments, food safety testing struggles to provide data for the release of production batches.

Two techniques are available to provide such information, each having its specific limitations. Amplification assays, such as PCR, are rapid well established and robust in trained hands. However, they require cell disruption, removing valuable histological, morphological and quantitative data at the cellular level. The alternative in-situ hybridisation is well known in the art but has not found its way into routine high volume testing. of genetic information. of genetic information.

Although ISH/FISH-based RNA and DNA detection techniques have been around for decades, they have been largely ineffective. They lack robustness and sensitivity to reliably detect the expression of genetic information. While Microarray and PCR provide useful molecular profiles of diseases, the clinically relevant histological information regarding cellular and tissue context, as well as spatial variation of the expression patterns in tissues or mixed cell populations are lost in the process. Currently available in-situ applications call lengthy hybridization and amplification procedures taking five hours for the total procedure. Effectively, they can only be accomplished in one day, if started at the beginning of a shift. Any sample arriving later needs to be either performed by two shifts, or call for an over-night procedure.

PCR procedures have been established to provide rapid results within 1-2 hours, including sample preparation. In these rapid applications the sample preparation encompasses total extraction of RNA/DNA disrupting any morphological correlations. Non-disruptive, In-situ PCR applications are also well known in the art. However, they call for very meticulous and lengthy procedures, sensitive to performance skills.

Other fluorescence in-situ hybridisation procedures (FISH) were devised to detect DNA and mRNA. These assays call for lengthy hybridisations and thus produce results in the best case at the end of a shift, usually however in two days upwards.

DNA-beacon technologies were developed to detect targets with ample numbers in-situ. This encompasses utilising the preference of DNA to form hair-pin loops wherever possible. This was used to develop oligo-nucleotides, which would form hair-pin loops with a targeting sequence in the loop and quencher-fluorophore pairs on the respective 3' and 5' prime ends. In the absence of a target the oligo-nucleotide will prefer the hair-pin loop conformation, bringing fluorophore and quencher into very close proximity. Upon excitation the quencher will capture the emitted photons and no signal is visible. In the presence of a target the loop will unfold and the two are separated. Upon excitation the oligo-nucleotide will emit a bright signal. This technology was developed further to identify ribosomal RNA within 30 minutes, allowing immediate identification of bacteria directly in clinical samples.

Other in-situ procedures were devised to shorten the assay time. Notably the branched DNA (bDNA) managed to bring the assay time down to one shift. Practically this means that only samples drawn at the very beginning of a shift may be analysed the same day. In a routine clinical environment this approach is effectively a two-day procedure.

All these assays produce qualitative data, where presence/absence is determined. The interpretation of the assays becomes ambiguous at the borderline of detection limits. This is especially the case with biological samples, which, frustratingly frequent, harbour auto-fluorescent particles. The issues concerning background fluorescence are enhanced when moving to higher magnifications. Skill and care in the preparation of samples becomes an issue, especially when dealing with glass slides of variable quality and age.

Only assays with total turn-around times of one to two hours are able to have an early impact on clinical decision finding and reduce treatment cost and potentially increase survival rates.

Moreover, the quantification of results is reduced to relative fluorescence with respect to background noise. Quantification in molar terms still remains a challenge.

It would therefore be desirable to have an assay that will provide both qualitative and quantitative molecular data within a histological context and the same time frame as other rapid histological techniques.

SUMMARY OF THE INVENTION

The present invention provides a multiplicity of nucleic acid probes or a composition comprising such probes to allow a robust and rapid in-situ hybridisation assay for the detection of DNA and RNA molecules. Methods, assays and kits are also provided.

In one aspect, there is provided an in-situ concatenated DNA-probe multimer, formed from at least two to a plurality of oligo-nucleotides, or nucleic acid probes, under stringently identical conditions, following 5' to 3' or 3' to 5' downstream target sequences essentially seamlessly, designed to work synergistically, all capable of hybridising simultaneously to the coding and complementary DNA-sequences of interest, where each oligo-nucleotide's 5' and 3' ends hold sequences designed to form helical stems in-situ with the neighbouring oligo-nucleotide in the presence of target sequences to polymerise in-situ, resulting in an elongated sequence with enhanced binding characteristics. Suitably, an essentially seamless array of individual, DNA oligonucleotide sequences hybridising to both the coding and complementary target sequences of genes is formed indicating the presence of a cell's malignant or otherwise pathogenic status. In other words, an assay to simultaneously detect DNA and cDNA in-situ. In one embodiment, an essentially seamless array of individual, DNA oligonucleotide sequences hybridising to both the coding and complementary target sequences of genes is formed indicating presence of antibiotic resistance or toxin gene expression in micro-organisms.

In another aspect or embodiment, there is provided an array of oligo-nucleotides, or nucleic acid probes, as defined herein, hybridising to any transcription product sequences of any length, from small non-coding RNA to messenger RNA. In one aspect or embodiment, there is provided an array of oligo-nucleotides or nucleic acid probes as described herein with non-target directed 3' and 5' ends designed to form short helixes interlinking only in-situ with the up- and downstream neighbouring oligo-nucleotides to effectively form one large stable hybridizing sequence of any length in either 5' to 3' or 3' to 5' directions. Suitably, the 5' end nucleotides are designed to mismatch the respective 3' up-stream target's sequence by having the alternative purine, where the up-stream target has the first purine, and, conversely, having an alternative pyrimidine-, where the target has the first pyrimidine-nucleotide. Suitably, the downstream, neighbouring oligo-nucleotides 3' mismatching sequence is designed to hybridise to the 5' nucleotides flanking the neighbouring upstream oligo-nucleotide following classical hybridisation rules. Suitably, the application of a set of rules defining the choice a flanking sequence prevents the hybridisation of flanking regions with target DNA or RNA. Suitably, all sequences towards targets are designed to hybridise with only one common ΔG (+/−2 kcal/mol) under hybridisation conditions.

In one embodiment, each stem formation provides an additional negative ΔG to the combined oligo-nucleotide array hybridisation process allowing the sum of target-hybrid and stem free energy to be fine-tuned to be within approximately 1 kcal/mol. Suitably, each stem formation provides an additional negative ΔG to the combined oligo-nucleotide array hybridisation process for the sum of target-hybrid and stem free energy to be restricted to be within approximately 1 kcal/mol under hybridisation conditions. Suitably, each stem formation provides an additional negative ΔG to the combined oligo-nucleotide array hybridisation process for the sum to be below the ΔG of the respective ΔG for the re-formation of the DNA double helix. Suitably, the ΔG of the stem formation are designed to be unfavourable in solution to disable self-elongation and the $T_m$ is designed to be below ambient temperatures to melt any forming self-hybridisation. Suitably, the oligo-nucleotides do not form self-quenching hairpin loops.

In one embodiment, there is provided an array of oligo-nucleotides or nucleic acid probes in accordance with the invention where the ΔG and $T_m$ of the target sequences to the coding DNA and cDNA overlap only to 50% the ΔG of the full target sequence.

In a further embodiment, the invention provides nucleic acid probe sequences where probes towards DNA and complementary DNA are prevented from self-hybridising in-situ giving false positive signals. Suitably, the oligo-nucleotide towards the complementary DNA covers the respective target's complementary sequence with essentially half of each of the complementary up- and downstream ΔG values of respective sequences. Suitably, the choice of targets on both coding and complementary DNA simultaneously shift the equilibrium from homologous DNA-helix re-formation towards heterologous hybrid formation. Suitably, the equilibrium of the hybridisation process is pulled away from self-hybridisation by the combined ΔG towards the full target plus stem sequences.

In another embodiment, there is provided an array of oligo-nucleotides or nucleic acid probes in accordance with the invention where the sequences hybridising to targets are DNA and the nucleotides forming the stem are DNA-analogues. In one embodiment, oligo-nucleotides or nucleic acid probes according to the invention are provided in which each alternating flanking sequence caries either an energizer (type-a probe) or a molecule capable of energy resonance transfer. Suitably the primary exciting energy is generated by light wave or low energy nuclide decay. In one embodiment, efficient energy (resonance) transfer is only possible in presence of the target providing ultimate proximity to each other and effectively emitting detectable photons. Suitably, the type-a probe carries at least one fluorescent moiety with a large Stokes shift. In one embodiment, the type-a probe carries at least one fluorescent moiety with a large Stokes shift with a fluorescence emission lasting up to milliseconds. Suitably the type-b probe carries at least one fluorophore with an excitation maximum coinciding with the emission maximum of type a probe. In one embodiment, the amount of photons emitted allows direct quantification via standards constructed under any of the previous claims, enabling automated reading and molar quantification. In one embodiment, the quantification provides means to determine a viral load both in a sample and at the cellular level.

In another embodiment, the invention provides an array of oligo-nucleotides or nucleic acid probes in accordance with the invention where the flanking regions are shortened by the use of non-nucleic acid spacer arms to form covalent crosslinks to achieve FRET enabling conditions. Other suitable systems used in nucleic acid hybridization assays are enzyme labelled systems including biotin-avidin system.

Suitably, the nucleic acid sequence in accordance with the invention may be constructed from ribonucleotides, ribonucleotide analogues, deoxyribonucleotides and/or deoxyribonucleotide analogues or combinations thereof.

In one embodiment, a nucleic acid probe, array of oligo-nucleotides or composition in accordance with the invention is directed towards transcription products of genes of diagnostic relevance.

In one embodiment, nucleic probe sequences may be chosen to provide at least one pair of probe types limited only by total target length or economic reasonableness.

Suitably, probe sequences may be applied in a non-disruptive assay, not compromising standard histological staining and reading procedures.

The invention further provides any diagnostic kit for the detection of DNA and RNA comprising probe sequences in accordance with the invention.

Suitable samples for using in the context of the present invention include biopsy samples, sections, and other biological material such as sputum, blood, urine, or other body fluids.

Suitably, the present invention may be used for the detection of any nucleic acids in cells from any kingdom.

In another embodiment, the present invention may be used to detect presence or absence of spoilants or contaminants in processed food and beverages In another embodiment, the present invention may be used to detect presence or absence of nucleic acids in environmental samples including but not limited to soil, dirt, dust and water.

Other embodiments provide methods for determining the biological status in bacteria, yeasts & moulds, parasites, human and animal tissue with respect to the production of toxins or antibiotic resistance.

Suitably, nucleic acid probe sequences in accordance with the invention may be labelled to allow automated quantification. In one embodiment, labelling is via a type-b oligonucleotide carrying a lanthanide complex. Suitably, bringing the said two types to close proximity generates a concentration dependent signal in presence of a target in an aqueous, i.e. quenching, environment.

Nucleic acid probe sequences as described herein may be designed at any starting point of any sequence giving an array of predictable sequences as exemplified in the sequences presented in Example 1.

In another embodiment, the invention provides probe sequences to determine a status quo of any cell of any kingdom.

Suitably probe sequences are capable of functioning both in native and fixed preparations.

In one embodiment, probe sequences for the detection of nucleic acids coding the HPV E6 protein are provided.

Further examples are given using the invention to further differentiate closely related organisms with identical ribosomal RNA sequences by detecting the presence/absence of marker mRNA sequences for microbial resistance or toxin production. Surprisingly it was found that, when applying the ZIP principles to the specific identification of bacteria, it was found that the specificity determined in a BLAST analysis increased by a factor of 10e14. FIG. 4*a* shows the specificity of a singular probe with an E-value of 0.049 and 4*b*, using the same specific sequence in combination with two flanking probes designed according to this invention, shows that the E-value increases to 2×10e-17 to 9×10e-20.

BRIEF DESCRIPTION OF THE DRAWINGS

FIG. 4 shows an example of a ZIP-probe design to identify a microorganism via a specific target in the ribosomal RNA. FIG. 4*a* shows NCBI BLAST for single target, and FIG. 4*b* shows NCBI BLAST for in-situ concatenation probes with respective E-values. The probe and target sequences shown in FIGS. 4*a*-1 to 4*a*-8 are SEQ ID NOs: 88 and 89.

FIG. 5 shows probes for the identification of rRNA together with mRNA coding for an expression product of diagnostic value. The target and probe sequences shown are SEQ ID NOs: 90 to 109.

DETAILED DESCRIPTION OF INVENTION

Figure 1:
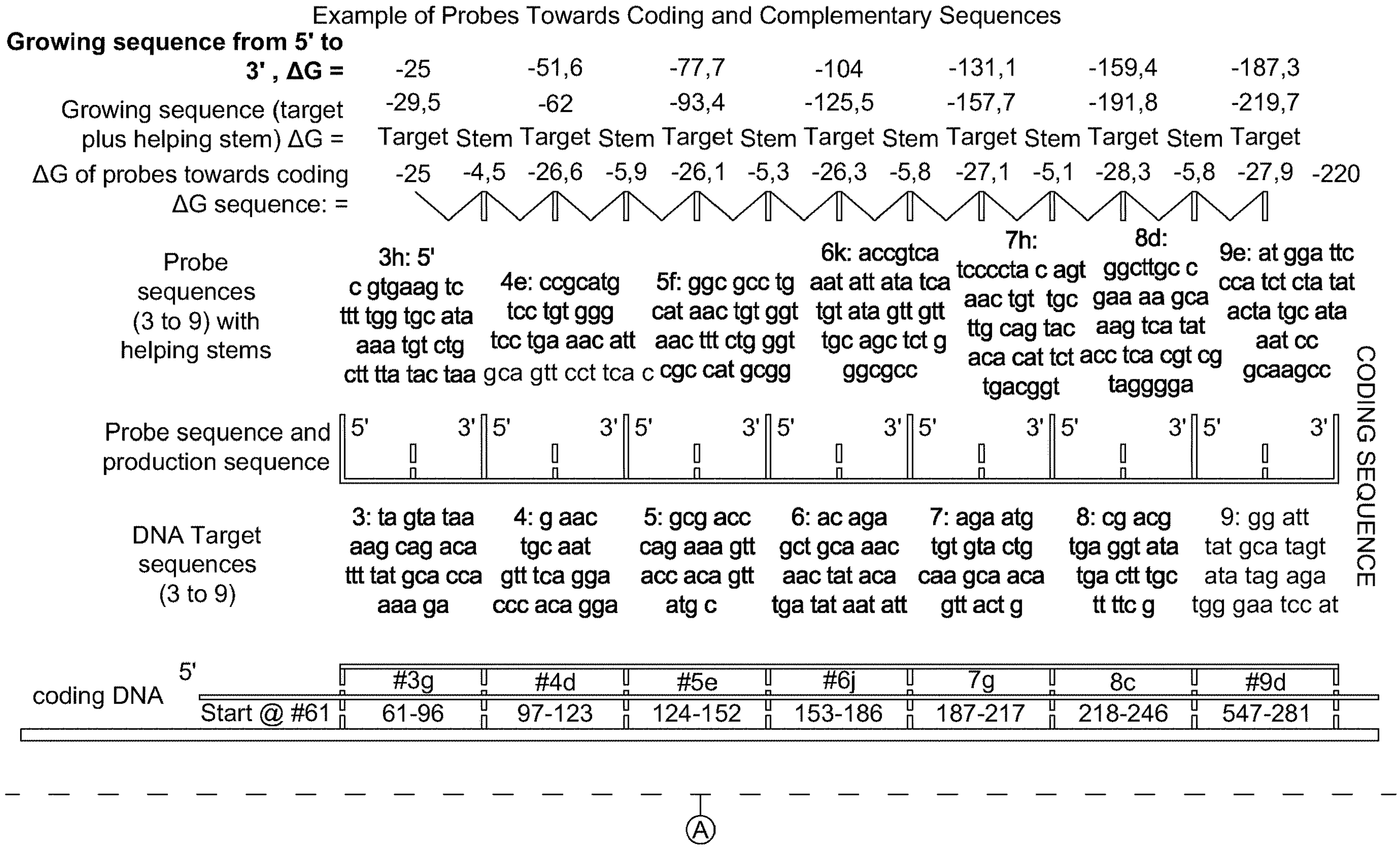
FIG. 1 shows an example of probes toward coding and complementary sequences. The probe and target sequences shown are SEQ ID NOs: 1 to 14 and 24 to 37.
Figure 1:
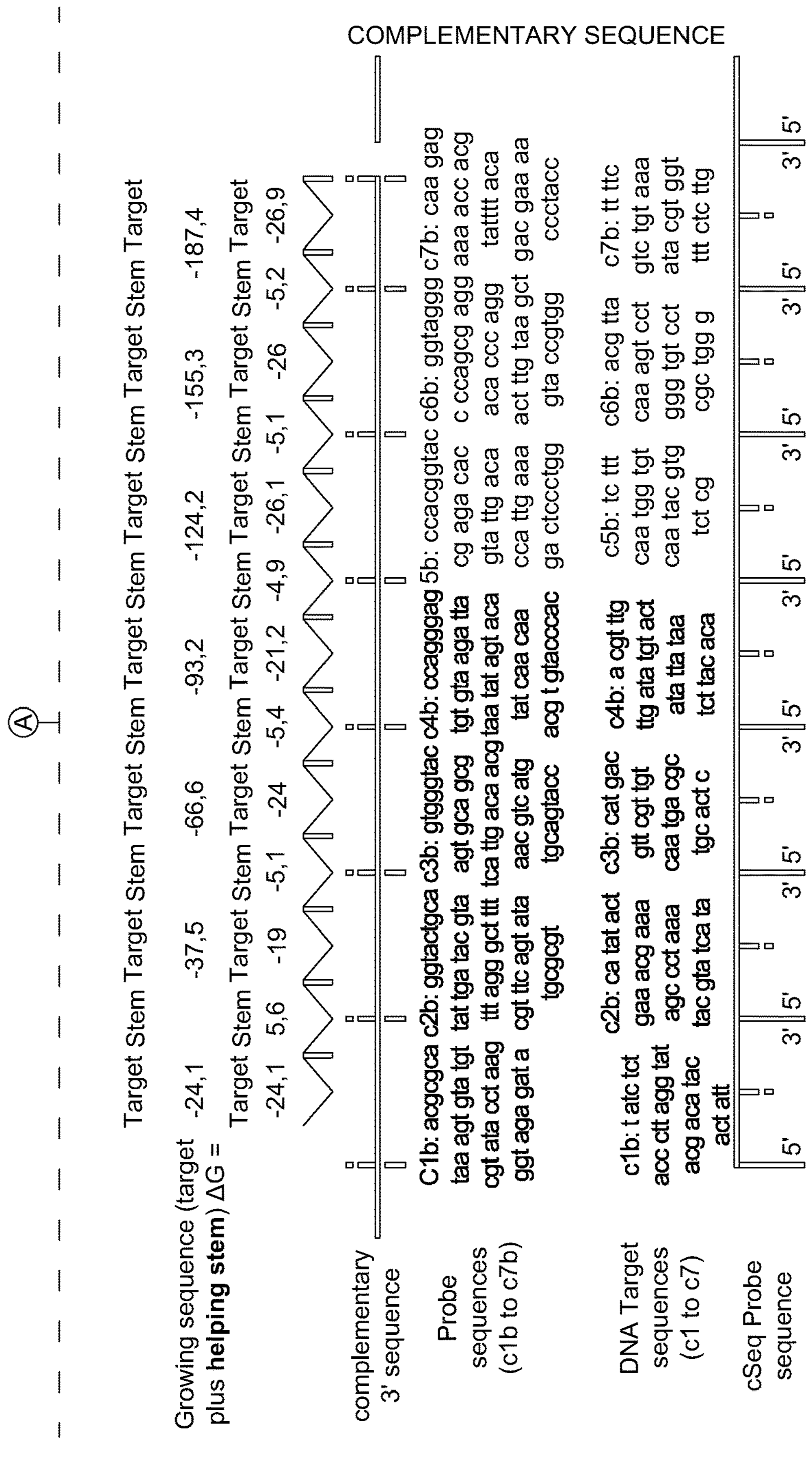

The objective of this invention is to enable a robust and rapid in-situ hybridisation assay for the detection DNA and RNA molecules with a target turnaround time of 1 hour. The robustness must enable high inter- and intra-lab reproducibility. Three aspects need to be addressed to shorten the turnaround time and enhance the reproducibility of an assay. The first critical point is the time required to complete the hybridisation. This must be reduced from several hours to several minutes without compromising specificity. The second point is the total number of steps required to produce a result, and thirdly the standardisation in the design of probes. Current assays require time, numerous steps and skilled hands in performing and reading the assays.

The issues may be addressed by finding ways to move towards a homogeneous assay. The most critical step lies in the differentiation between bound and unbound probes and the generation of a high signal to noise ratio. One obvious way would be to use molecular beacon technology. The major feature in beacon technology lies in the construction of the stem, where the stem opens only in the presence of a cognate target sequence. Un-hybridised sequences return to the thermodynamically favoured hairpin-loop formation in which a potential signal is quenched. Only bound, unfolded beacons will give a signal. The energy liberated in the hybridisation must be larger than the free energy of the hairpin-loop formation. Thus a large amount of free energy is consumed in opening the hairpin-loop structure. A target nucleic acid in-situ is seldom freely available for two dimensional hybridisation with straight forward two step kinetics. DNA and RNA are folded three dimensional molecules, they are not stand alone molecules, but well entwined 3-dimensional (3-D) protein nucleic acid complexes. In order to hybridise these complexes need to be unraveled and ionic conditions must be installed to favour the probe-target complex rather than the indigenous one. The process remains dynamic and competitive in the presence of all reaction partners, as is the case in homogeneous assays.

$$\Delta G_{3\text{-}Dtarget\ complex}+\Delta G_{Hairpin\ loop} <===> -\Delta G_{hairpin\ loop}+\Delta G_{probe/target}-\Delta G_{3\text{-}Dtarget\ complex}$$

Therefore, in a successful hybridisation, the energy favouring the return to the start configurations must be overcome by choosing appropriate probe sequences and assay conditions.

Existing assays shift the equilibrium by changing the ionic environment or washing unbound probes. The current invention is related to designing probes and conditions that will enable, favour, and stabilise the probe/target hybrid. The underlying concept is to use sequences that will hybridise and in-situ to form polymerised probes that can only generate a signal, when successfully in place, i.e. in the hybrid complex. The binding kinetics, i.e. high $K_{on}$ and $K_{off}$, in this configuration will shift from the fast binding of a plurality of small probes to the slow binding, i.e. slow $K_{on}$, $K_{off}$ of a very large nucleic acid sequence.

$$\sum_{1}^{n} \text{high } k_{on}; k_{off} \text{ for small probes} ==> \text{in-situ,}$$

$$\text{one large probe with low } k_{on}; k_{off} \text{ kinetics}$$

It requires time to shift the equilibrium towards the desired hybrid, where the hairpin loop is open and hybridised to the target, open to excitation/emission. Unbound hairpin loops are closed and no signal can be generated.

The subject matter of this invention is to utilise the free energy otherwise generated in the hairpin loop stem formation, and using this free energy to stabilise the binding of a plurality of probes to the target DNA or RNA. In this invention sequences are chosen, which cause a stem to be formed only in the presence of a target and only when hybridised. The total free energy generated in this configuration is the combined free energy of the hybrid and the stem forming in-situ. The differentiation between bound and unbound probes is achieved by applying FRET technology well described in the art.

This involves selecting a pair of fluorophores that have the emission wavelength of first fluorophore overlapping with the excitation wavelength of the second and a combined stokes shift as high as possible. A multitude of fluorophores are commercially available fulfilling this criterion. The preferred combinations are lanthanide chelates combined with fluorophores with a sharp emission maximum at 620 nm. The most preferred combination is a Europium chelate with an emission maximum at 620 nm, combined with a fluorophore being excited at 620 nm (+/−10 nm), e.g. Atto 620. The combination requires close proximity, to enable energy resonance transfer. Conditions and sequences need to be chosen and maintained under which the stem-sequences of unbound probes do not anneal to generate background noise and thus reduce the sensitivity of the assay.

Formation of Zip-Probes

In analogy to click chemistry, where reactions are in "one pot", and are characterised by a high thermodynamic driving force that drives it quickly and irreversibly to high yield of a single reaction product, according to this invention nucleic acid probes are sent inside a cell to hybridise towards respective target sequences. The targets are chosen to be as juxtaposition to each other as possible. The preferred position of neighbouring probes is without an intermediate sequence and most preferred without a spacer nucleotide. It is essential that the thermodynamic characteristics (ΔG) of all probes are designed to be as identical as possible. The standardisation is made according to the overall thermodynamic characteristics. Traditionally in the art the $T_m$-value is used to determine the length of a desired NA-sequence. However, here the free energy developed upon hybridisation has proven to be the most helpful parameter, as a sequence with a positive ΔG will not hybridise. The design is made by carefully choosing and adding bases to achieve the desired negative ΔG. For practical reasons one standard temperature must be chosen for all hybridisations. The ΔG of the sequence hybridising to the target should be chosen to be negative at the chosen hybridisation temperature. The preferred ΔG is between −15 and −35±5 kcal/mol. The most preferred ΔG was found to be at −26 kcal/mol. Furthermore, increasing the stringency of the bandwidth of ΔG allowed, increased the robustness of the overall assay. The most stringent values were designed to be, when the ΔG value is held within ±1.5 kcal/mol.

The most important aspect of this invention is to add a 5'flanking sequence, strictly not-hybridising to any target sequence in the vicinity, especially not to the directly neighbouring 5'-upstream sequences. This is achieved by rigorously swapping the coding sequences in the 5' flanking sequence. All changes will disturb hybridisation. The preferred swap is: A for G; G for T; C for A; T for C. The 3'flanking sequence of the neighbouring probe is made by complementing G with C; T with A; A with T, and C with G with respect to said 5'flanking sequence. This swap to force a mismatch of the 5'flank will also ensure that any sequence used to flank the neighbouring 3' end will also mismatch the target's coding sequence.

The length of the flanking sequence may be chosen from between one and a plurality of nucleotides. The preferred length is between 5 and 15 nucleotides. The most preferred number of nucleotides is defined by the amount needed to form one helical twist, when brought together with the 3'flanking sequence .of the neighbouring 5'-upstream oligonucleotide. Moreover, the sequences must be chosen in such a way that mixture of oligonucleotides present in one assay do not hybridise freely with each other under either hybridisation or reading temperatures and their required buffer and salt configurations. Very surprisingly it was found that it is possible to choose sequence that form a helix, having a negative ΔG and a $T_m$-value close to 0 °C. The most desirable length is when the ΔG is negative at −4.5 (+/−1.5 kcal/mol) and allows one full helical twist. This finding is of importance, because, while the flanking regions enable the forming of one long oligonucleotide multimer, it ensures that reading at room temperature will not allow these flanking sequences to anneal in solution, thus enabling a homogeneous assay. Choosing this design allows the application of FRET technology to generate the signal in a homogeneous assay.

In such a configuration the ΔG of this helix adds a positive stabilising effect, i.e. it increases the total amount of energy liberated, when one probe thus "zips" in one next to the other. The probe design starts at the 3' end towards the 5' end, i.e. following the coding sequence upstream. The individual probes are constructed 5' to 3'. This process may be elongated along the complete target sequence without limitation in length.

The teachings of WO 03/076655A2 describe the usage of at least two imminently neighbouring probes with stems carrying a fluorophore to the 5'flank of the first probe with a sequence complementary to the 3' stem of the second probe carrying a second fluorophore. In combination, the two fluorophores allow energy transfer. In the described preferred application, molecular beacons are applied; where non-bound hairpin loops emit a signal two to five times lower than the signal of a probe bound to a target due to the quenching fluorophore in the beacon. Using beacons results in the binding of a hairpin loop with a quencher at either the 3' or 5' end of the probe binding to the target. In reality this means that the preferred use of beacons only allows the usage of two beacons to bind to a target in such a way that FRET may be achieved. Furthermore, this is only possible if the quencher on probe #1 carries the quencher on the 5' end and probe #2 carries the quencher on the 3' prime end, as shown in FIG. 1 of WO 03/076655 A2. The overall signal generated therefore cannot be stronger than that of a single beacon. The combined pair of probes carry quencher both on the 3' and 5' end precluding an addition of a further probe as the signal of a third neighbouring beacon would be quenched. Therefore, the usage of beacons rules out the formation of unlimited multimers as described in the present invention. WO 03/076655A2 is therefore not suitable for the generation of multimers and therefore for any practical application in a homogeneous assay.

Figure 3:
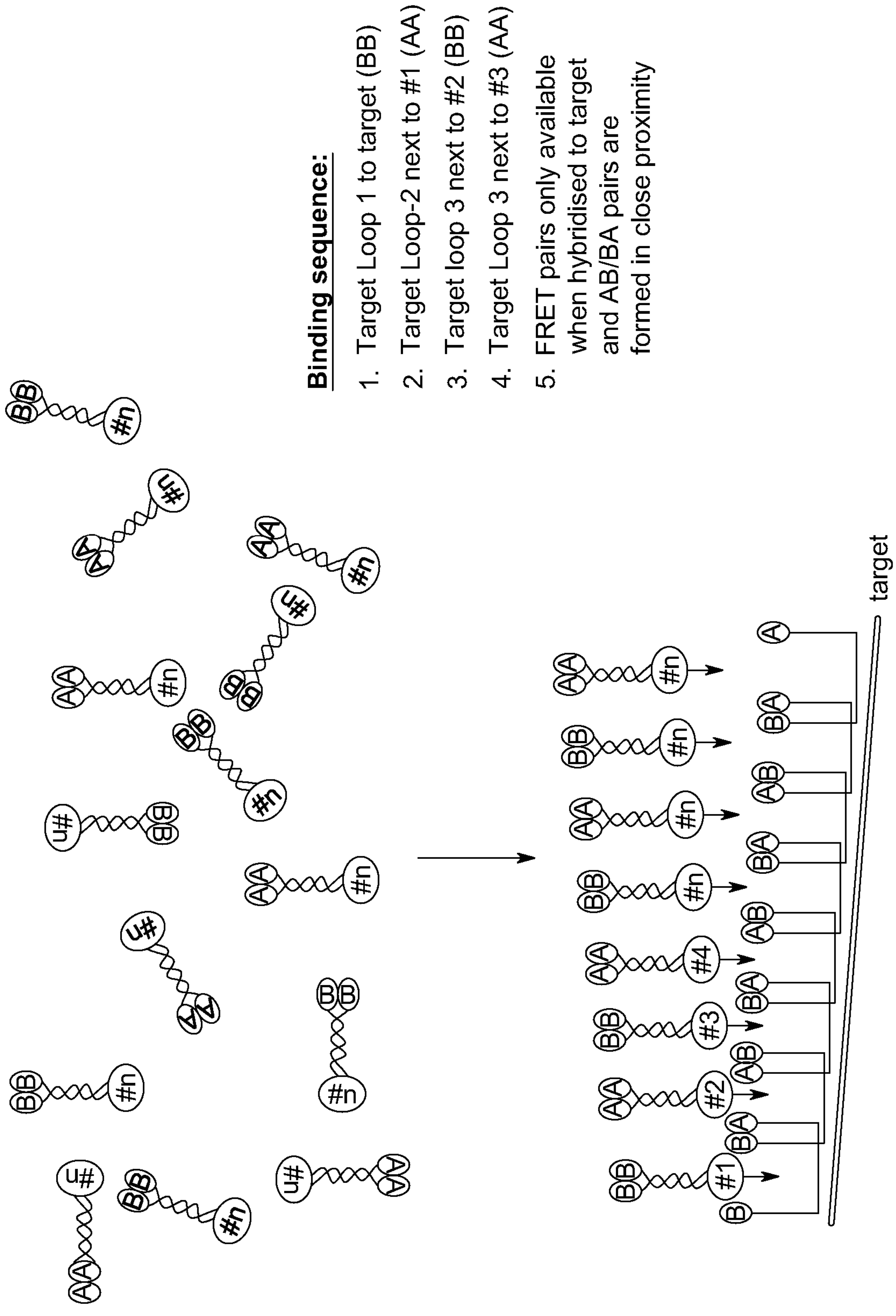
FIG. 3 shows an example of an in-situ concatenated probe assay.

Disadvantages in the prior art are resolved in the present invention by using hairpin loops strictly using the same fluorophores on both 3' and 5' end of the hairpin loop enabling a homogeneous assay with no washing step required. FRET is achieved by alternating the fluorophores up and down-stream with hairpin loops carrying either fluorophores “A” or “B” on each respective hairpin loop to form FRET-pairs “AB” only when bound to a target (FIG. 3). FRET pairs, well known in the art may be chosen for this application. This represents an in-situ concatenation driven by the design of stem sequences.

Only in this formation, strictly omitting the usage of quenchers is it possible to form a plurality of hairpin loops bound to a target excerpting the fast kinetics of small hairpin loops and unfolding the full combined thermodynamic advantage of a large sequence binding to a target in-situ. Moreover, only in this formation is it possible to achieve the enhanced sensitivity of having multiple probes binding to one target.

Furthermore, WO 03/076655A2 does not teach how to design stems without cross reactivity. The careful design of stems as described above to avoid malalignments and background noise is an essential part of the present invention and the usage of beacons is precluded. The teachings of US 2005/0287548 A1 describes the usage of beacons with shared stems to form FRET-pairs and do not lead to the formation of multimers, because of said preclusion. U.S. Pat. No. 6,472,156 B1 uses allelic configuration to bring fluorophores into physical vicinity to allow FRET to occur. It does not teach the formation of multimers.

Surprisingly, when a NCBI BLAST is made for in-situ concatenated probes, constructed according to the present invention, with a specific probe for the identification of a microorganism such as *Staphylococcus aureus* and neighbouring nonspecific probes in comparison to the respective single specific probe, the E-value drops from <0.05 to <10-15 (FIGS. 4*a* and 4*b*). This indicates a significant enhancement of the specificity of an in-situ concatenated probe versus a single linear or beacon probe.

A further aspect of this invention is to add a fluorophore to the 5'flank of the first probe starting at the target's said 3' end and a corresponding fluorophore on the 3'-flank of the second. 5' upstream neighbour. A thermodynamically favoured helix is formed as an uninterrupted stem and will bring both fluorophores into very close proximity to enable FRET to occur. The very close proximity is advantageous, because resonance coupling carries an exponential decay with the distance. Combined with the virtues of time resolved fluorescence, this in-situ pairing enables a homogeneous assay, eliminating auto- and background fluorescence. The fluorophores are attached to the oligonucleotides via a spacer. It is especially advantageous, if a long spacer arm is included, distancing the fluorophores as well as being a dielectric preventing quenching from electron rich, stacking nucleotides.

In theory these spacer arms could also carry chemically active groups that would allow the application of technologies well known in the art of protein affinity labelling to form crosslinks in situ. This would give a covalent link between the oligonucleotides to form one long covalently liked molecule in-situ. The preferred choice of affinity label would encompass the design of an Azido group on one flank and lysine with a free epsilon amino-group positioned such that a covalent link may be formed by the same wavelength required for the excitation of lanthanide based fluorophore within the assay.

Any pair of fluorophores described in the art may be chosen. The preferred choice of fluorophore is where energy resonance may be achieved and energy be transferred from one fluorophore to the other. The objective in the choice is to generate the highest possible combined stokes shift and optimised energy transfer. This is only possible where close proximity is achieved to allow (fluorescence) resonance energy transfer (F)RET as described by Förster (Forster Theodor (1948): Intermolecular Energy Migration and Fluorescence. Ann Phys 437: 55-75). Other non-bound fluorophores will be in solution surrounded by water, which will quench the signal from unbound probes. This is a critical component for a timesaving homogeneous assay. The most preferred choice is to use a chelated lanthanide as energy/electron donor and a fluorophore with an excitation wavelength equivalent to the lanthanide's emission wave-length. This combination, with a combined stokes shift of 250 to 300 nm, gives a very high signal to noise ratio which can be further enhanced by utilising time-resolved fluorescence technology well known in the art and readily commercially available.

In the choice of partners in FRET, three conditions need to be fulfilled. First, donor and acceptor should present energy compatibility, i.e., donor emission spectrum and acceptor excitation spectrum should overlap completely. Second, the donor and the acceptor should present compatible orientation. The transfer is maximal when the donor and acceptor transition dipole moments are parallel, and are minimum (equal to 0) when they are perpendicular. The most important factor is that energy transfer can take place only if the two partners are in very close proximity. The efficiency of the transfer is inversely proportional to the sixth power of the distance.

$$E=R^6/R^6+r^6$$

Where $R_0$ is the distance corresponding to 50% energy transfer efficiency. For FRET to occur the two partners should be in the range of within 30-60 Å. The objective of constructing this configuration is to utilise the helix formation to provide the close proximity and maximise FRET efficiency with highest possible signal to noise ratio.

Many fluorophore combinations are described in the art, which may enable FRET. Because of the emission peak around 490 nm, Terbium-cryptate is an option and is compatible with fluorescein-like fluorophores as an acceptor. The especially preferred lanthanide is Europium, which is excited at 335 nm. It exhibits a large Stoke shift with major a emission peak at 615-620 nm. Europium also has a time of photon emission particularly suitable for time resolved fluorescence. This makes europium chelates compatible with deep red fluorophores the most preferred choice of fluorophores to perform FRET.

In using the said fluorophore partners in said assay formation the formed helix will bring the two partners within the required range for FRET. Other non-bound probes will be too far apart and be quenched by the aqueous environment of a homogeneous assay.

A further aspect in the design of such electron and energy rich fluorophores. The excited energy may be dissipated to other energy rich components such as nucleotides, especially Guanidine. They need to be separated by a dielectric. This is achieved by choosing a spacer arm for the chelate, sufficient to suppress the dissipation of energy, i.e. quench. The spacer design may also be made to incorporate a cross-link between the two partnering spacer arm using said affinity label techniques. Proximity might be achieved in many ways with the help of DNA probes. A long spacer arms may be added with said cross linking reagents, without help of the stem. However, the stem was chosen to enhance the kinetic performance under hybridisation conditions and simplify the probe construction.

The crosslinking in turn polymerises the short probes in-situ to rapidly form one large hybridising molecule with now changed kinetic properties.

$$\sum_{1}^{n} \text{high } k_{on}; k_{off} \text{ small probes} ==> \text{in-situ},$$

$$\text{one large probe with low } k_{on}; k_{off} \text{ kinetics}$$

Effectively, one large NA-multimer is formed by concatenation in-situ, and only in the presence of a cognate sequence, which now binds to the target with increasing intensity. As the strand grows in length, the free energy generated by the multimer will be increasingly more negative ΔG and have higher $T_m$ than the individual small oligonucleotides. The hybrid will stabilize and not dissociate, providing the robustness required for a routine assay. In summary the kinetics may be described as $$\sum_{1}^{n} \text{high } k_{on}; \text{ of small probes} ==> \text{in-situ},$$

$$\text{one large probe with low } k_{off} \text{ kinetics}$$

Such an assay design combines the speed of small oligonucleotide hybridisation with sensitivity and specificity of large nucleotide probes or cosmids.

The same principles may be used to develop probes towards messenger RNA of sequences of interest. As the thermodynamic characteristics in the binding between RNA and DNA differ from DNA/DNA hybrids, the sequences for the mRNA detection will be shorter in order to work under identical assay conditions. This will allow the efficient development of commercial assays, all working under identical conditions. Moreover it will allow the simultaneous detection of a given DNA sequence with its expression product in the same cell.

A further aspect in reducing hybridisation time and simultaneously doubling the signal strength is to present probes towards the DNA sequence complementary to the target, i.e. to the cDNA. This would normally be a self-defeating approach as probes to the cDNA would hybridise with probes to the original target sequence, annihilating the initial objective. However, this may be avoided by introducing a “phase shift”. The over-lap between two probes addressing complementary DNA and cDNA targets are only allowed to have 50% over-lap with respect to their ΔG values. When stringently applied, this will render the binding between said probes thermodynamically far inferior to any full sequential match, thus making this approach viable.

Therefore, when trying to detect DNA and cDNA together to enhance sensitivity the following needs to be considered. In order to prevent probes targeted to primary DNA target and those targeted towards the complementary sequence self-hybridising fortuitously the target and complementary targets must overlap to a maximum with the next downstream sequence. This requirement determines the sequences of the complementary sequence. Furthermore the overlap needs to be measured in ΔG as sheer numbers generates a shift and cause biases which could lead to self-hybridisation. Effectively this would take probes out of the equilibrium and reduce the hybridisation efficiency and thus slow down the whole assay.

Removing the cDNA out of the equilibrium will additionally favour the hybrid formation over the re-formation of the original helical DNA, speed and stabilise the system.

A further aspect of the design is to combine the virtues of DNA and DNA analogues. Lacking the charged phosphate backbone, DNA-analogues are poorly soluble in an aqueous environment. Effectively their length is limited to 12-15-mers. Using DNA for the target sequences, combined with DNA-analogues for the stem forming sequence will maintain the solubility, while easing the passage across membranes. This may not only speed the membrane passage and thus the assay but also reduce unspecific binding to membranes. Moreover, the DNA-analogues have a more negative ΔG and will increase the free energy liberated upon binding.

In view of the above, it will be appreciated that the present invention also relates to the following items:

Item 1: A multiplicity of non-beacon, hairpin loop forming nucleic acid probes capable of forming a concatenated hybrid in-situ with a target nucleic acid sequence, said nucleic acid probe comprising:

a nucleic acid sequence complementary to the target nucleic acid sequence;

a 5' flanking sequence comprising a first detection moiety, and a 3' flanking sequence comprising a second detection moiety;

wherein said nucleic acid probes are capable of forming a multimer in-situ with at least another neighbouring nucleic acid probe such that, when the nucleic acid sequence is bound to the target sequence, the 5' flanking sequence of the nucleic probe interlinks with at least part of the 3' flanking sequence of a neighbouring probe to form a stem such that the first and second detection moieties of a stem interact to generate a signal.

Item 2: A multiplicity of nucleic acid probes according to item 1, wherein the 5' and/or 3' flanking sequence do not hybridise with the target nucleic acid sequence.

Item 3: A multiplicity of nucleic acid probes according to item 1 or item 2 wherein the stem formed by the 5' and 3' flanking sequences is a helix having a negative ΔG and a Tm-value close to 0 °C.

Item 4: A multiplicity of nucleic acid probes according to any of the preceding items, wherein said nucleic acid sequence complementary to the target nucleic acid sequence comprises ribonucleotides, ribonucleotide analogues, deoxyribonucleotides and/or deoxyribonucleotide analogues or combinations thereof.

Item 5: A multiplicity of nucleic acid probes according to any of the preceding items wherein the nucleic acid sequence complementary to the target nucleic acid sequence is DNA and the 5' and 3' flanking sequences comprise DNA-analogues.

Item 6: A multiplicity of nucleic acid probes according to any of the preceding items, wherein the target nucleic acid sequence is DNA or RNA.

Item 7: A multiplicity of nucleic acid probes according to any of the preceding items, wherein said first detection moiety is an energizer (type-a probe) and said second detection moiety is a molecule capable of energy resonance transfer (type-b probe); or wherein said first detection moiety is a molecule capable of energy resonance transfer (type-b probe) and said second detection moiety is an energizer (type-a probe).

Item 8: A composition comprising a multiplicity of nucleic acid probes as claimed in any of the preceding items.

Item 9: A composition according to item 8, wherein the nucleic acid sequences complementary to the target nucleic acid sequences on neighbouring probes are designed to hybridise to the target nucleic acid sequence with only one common ΔG (+/−2 kcal/mol) under defined hybridisation conditions.

Item 10: A composition according to item 9, wherein ΔG is <0 kcal/mol at the chosen hybridisation temperature, in particular wherein ΔG is between-15 and −35±5 kcal/mol, more particularly ΔG is between −24 and −30.

Item 11: A composition according to any of items 8-10, wherein said first detection moiety is an energizer (type-a probe) and said second detection moiety is a molecule capable of energy resonance transfer (type-b probe); or wherein said first detection moiety is a molecule capable of energy resonance transfer (type-b probe) and said second detection moiety is an energizer (type-a probe) such that the combination brings together a type-a probe and a type-b probe such that FRET technology is used to generate the signal.

Item 12: A composition according to item 11, wherein efficient energy resonance transfer is only possible in presence of the target nucleic acid sequence where said first and second detection moieties are in proximity to each other and effectively emit detectable photons.

Item 13: A composition according to item 12, wherein the amount of photons emitted allows direct quantification enabling automated reading and molar quantification.

Item 14: A composition according to items 8-11, comprising an essentially seamless array of probes carrying identical fluorophores on both 5' and 3' end, where neighbouring probes alternate to carry fluorophore A on one, fluorophore B on the second, fluorophore A on the third, fluorophore B on the forth and multiples thereof, where a FRET dependent signal is only generated when AB pairs form.

Item 15: A composition according to item 13, wherein the quantification provides means to determine a viral load both in a sample and at the cellular level.

Item 16: A composition according to items 8-15, wherein the multiplicity of probes comprises probes to DNA and mRNA.

Item 17: A composition according to any of items 8-16, wherein the multiplicity of probes comprises probes to DNA and cDNA, in particular where the probes are capable of hybridising simultaneously to the coding and complementary DNA-sequences of interest.

Item 18: A composition according to item 17, wherein nucleic acid probes towards DNA and complementary DNA are prevented from self-hybridising in-situ, in particular wherein the over-lap between two probes addressing complementary DNA and cDNA targets are only allowed to have 50% over-lap with respect to their ΔG values.

Item 19: An in-situ hybridisation method comprising (a) contacting a multiplicity of probes according to any of items 1-7 or a composition or multiplicity of nucleic acid probes of any of items 8-18 with a biological sample;

(b) hybridising the nucleic acid probes of (a) with the sample;

(c) inducing conditions which allow for stem formation between neighbouring probes and favour stabilisation of the probe/target hybrid complex, wherein the stem allows interaction of the detection moieties.

Item 20: A method according to items 19, wherein the probe sequences are applied in a non-disruptive assay.

Item 21: A method according to items 19 or 20, wherein the method is a homogeneous assay.

Item 22: Use of a multiplicity of nucleic acid probes according to any of items 1-7 or a composition of any of items 8-18 in the method according to any of items 19-21 to identify the presence or absence of one or a plurality of organisms within a biological sample.

Item 23: Use according to items 21, wherein the use is diagnostic use.

Item 24: Use according to items 21 or 22, wherein the organism is a virus, e.g. HPV, in particular where nucleic acids coding the HPV E6 protein or the HPV E4 protein are detected.

Item 25: Use according to any of items 21-23, wherein the biological sample is any sample of biological origin, such as a clinical sample or a food sample.

Item 26: A kit for the detection of a target nucleic acid, said kit comprising a multiplicity of nucleic acid probes according to any of items 1-7 or a composition or multiplicity of nucleic acid probes according to any of items 8-17.

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

By concatenating, it is meant that DNA fragments are joined at the end of another DNA fragment. "Concatenating" as used in the present invention describes nucleic acid probes that can concatenate with at least another neighbouring probe to form a multimer. Advantageously, as the strand grows in length, the free energy generated by the multimer will be increasingly more negative (ΔG) and the strand will have higher $T_m$ than the individual small oligonucleotides.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Figures 2, 5A:
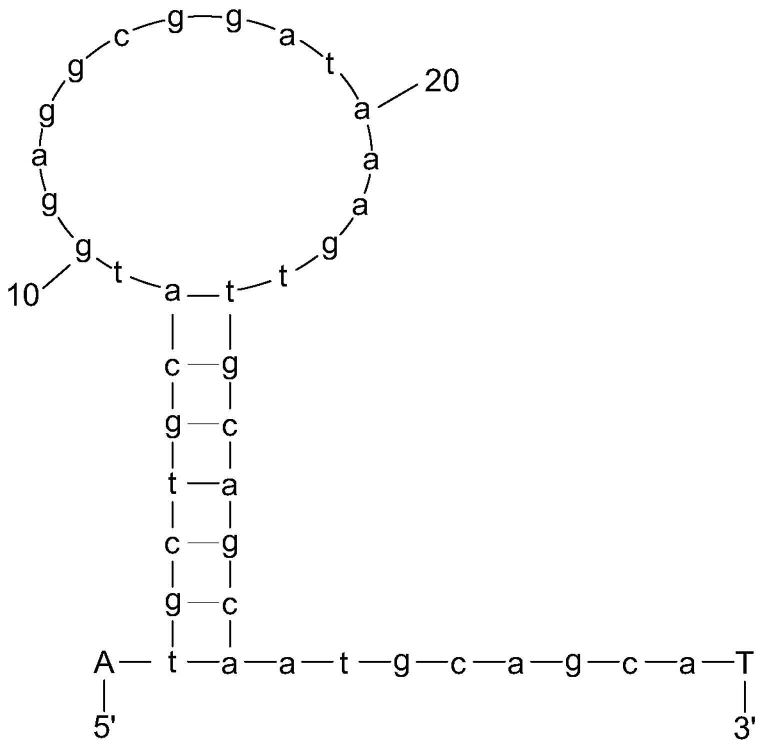
FIG. 2 shows an example of probes against HPV protein E6 within pos 1. The target, half target, half probe and resulting cDNA sequences shown are SEQ ID NOs: 2, 4, 6, 8, 10, 12, 14, 23 and 38 to 87.
Figures 2, 5B:
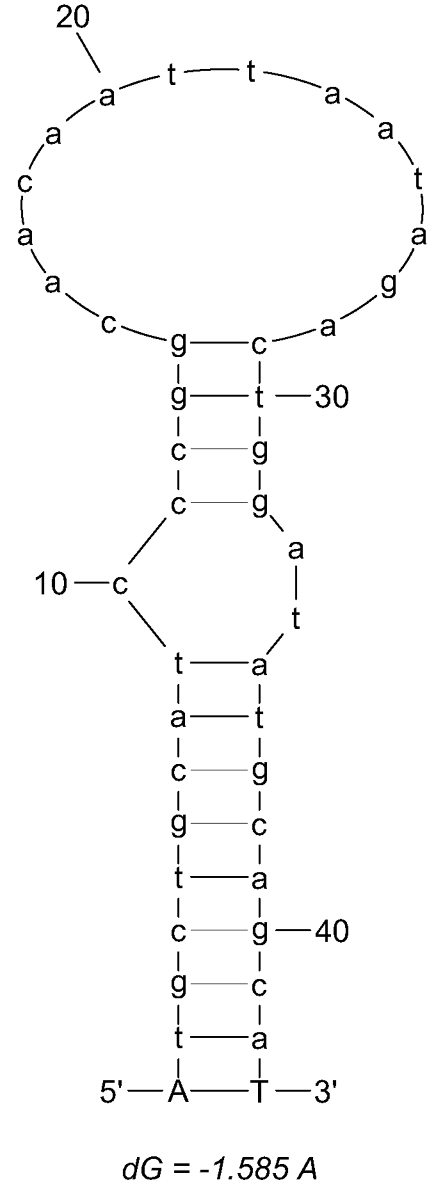
Figures 2, 5C:
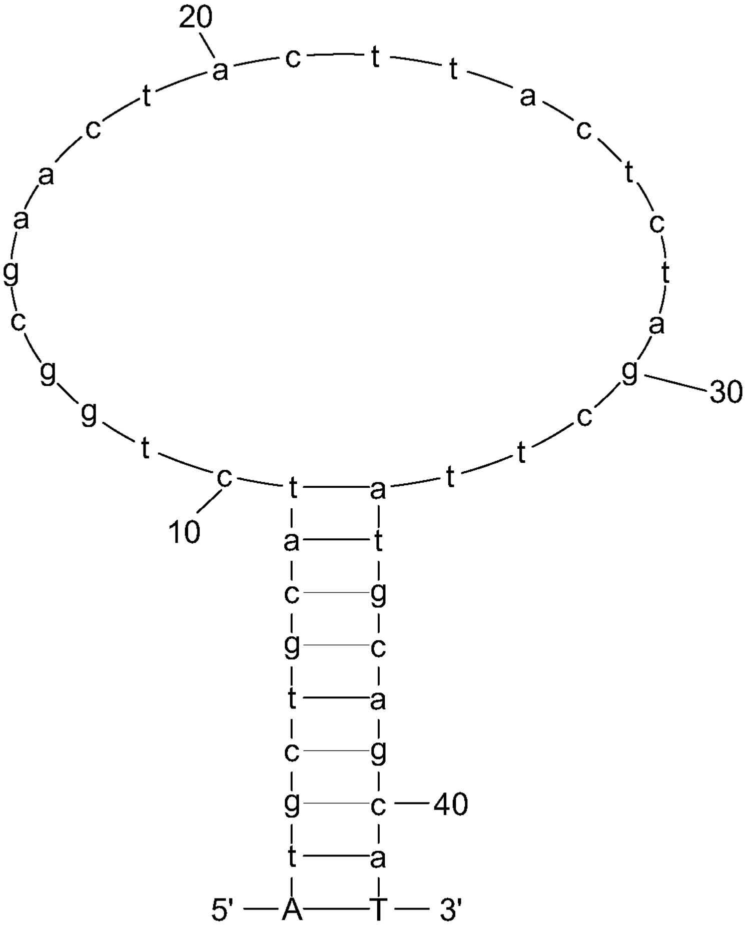
Figures 2, 5D:
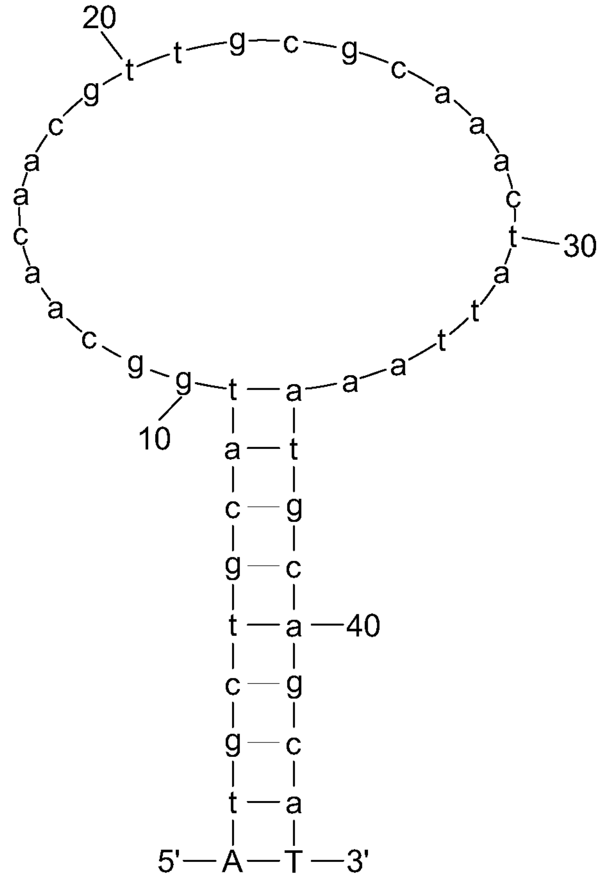
Figures 2, 5E:
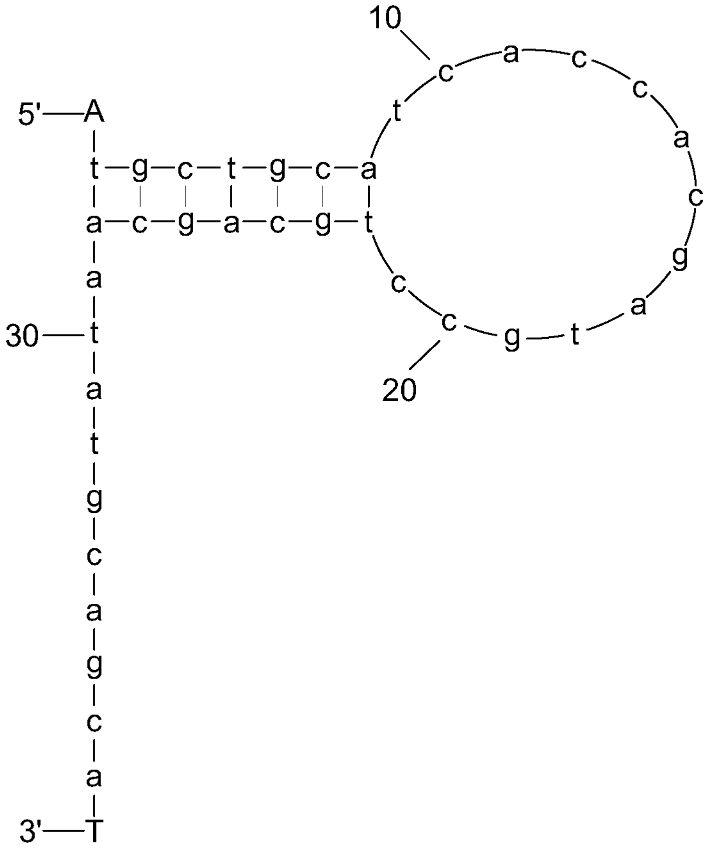
Figures 2, 5F:
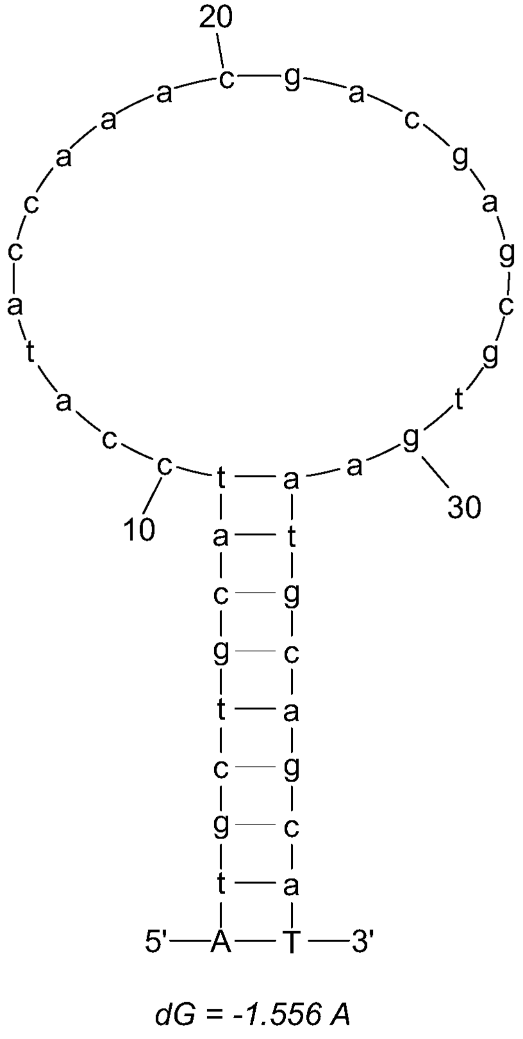
Figures 2, 5G:
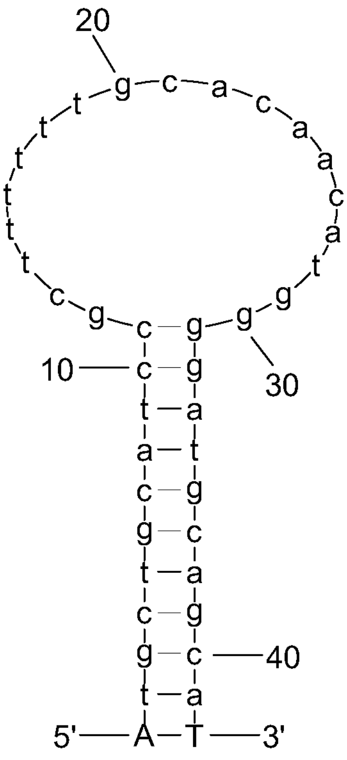
Figures 3, 5G:
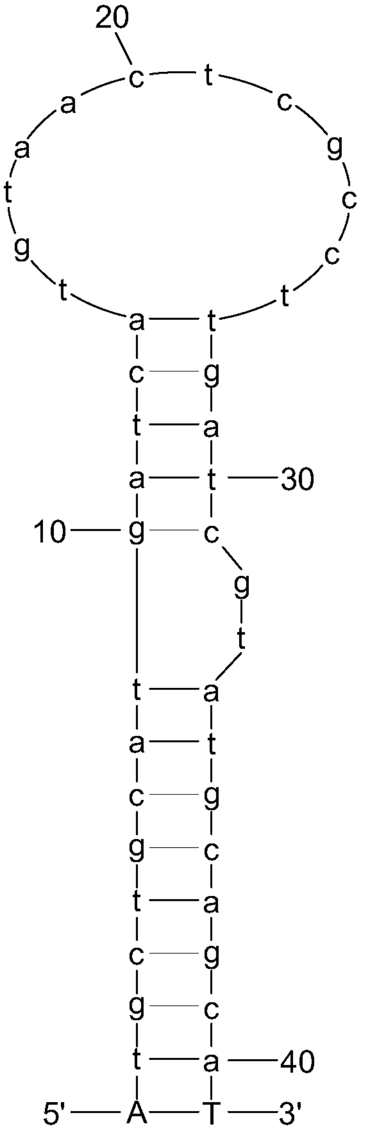
Figures 2, 5H:
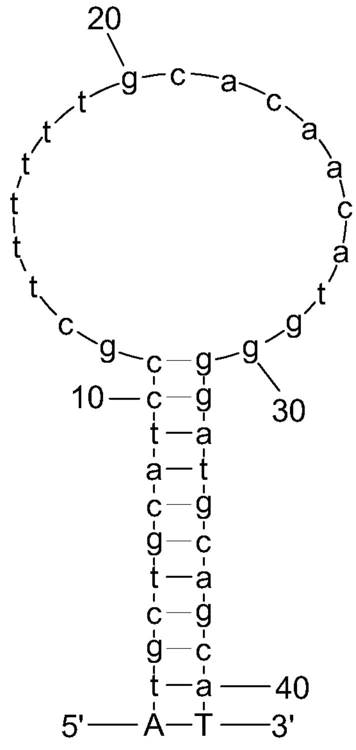
Figures 3, 5H:
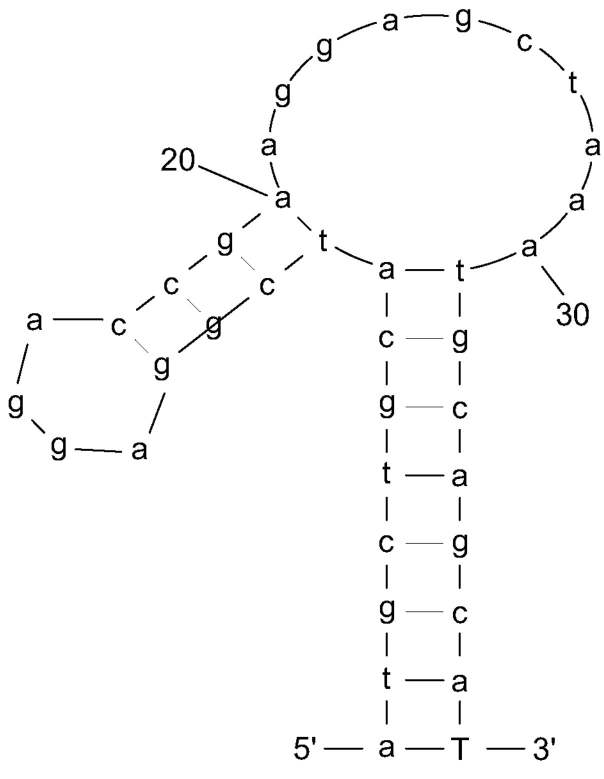

EXAMPLES a. Probe design: The thermodynamic values are calculate using the tool provided by The DINAMelt Web Server: http://unafold.rna.albany.edu/?q=DINAMelt/Two-state-melting, entering standard hybridisation conditions and the temperature of choice. The hybridisation temperature chosen was 50 °C and corrected for any urea entered to the assay. Salt and Mg concentrations were standardised to be 25 mM NaCl and 10 mM divalent metal salts.

b. The example chosen here is to demonstrate an assay to detect DNA from HPV E6 protein. The following probe sequences is an example, starting arbitrarily at position 61 of the published sequence. Designing a set of probes, starting at any other position follow the teachings presented here will result in a highly predictable sequences, Sequence samples and their respective thermodynamic values are in the attached file, FIG. 5. FIG. 2 shows an example of probes against HPV protein E6 within positions 1-600.

Also, FIG. 1 shows an example of probes towards coding and complementary sequences.

c. A further example chosen is to demonstrate the usefulness of this invention is in the design of a ZIP-probe to identify a microorganism via a specific target in the ribosomal RNA with enhanced specificity, (FIG. 4*a,b*).

d. Assay procedure i. Sample Preparation:

The sample preparation follows all well established procedures known in art described for ISH procedures, and calls for no deviation from the procedure, be it smears, swabs, sputum, section, and paraffin embedded sections with one exception. As well known in the art, when probes towards Gram positive cells are applied, the cell wall needs to be digested with a lysis mixture comprising proteolytic enzymes such as but not limited to Lysozyme and/or Lysostaphin to enable said probes to enter the cytoplasm.

ii. Full Assay (a)

1. Dip in EtOH bath for 5 min
2. Place on hot (50 °C) plate until dry
3. Add hybridisation mix, sufficient to cover tissue
4. Close lid and hybridise for 10 min
5. Briefly dip in stop solution (hybridisation buffer without probes at RT for 1 min
6. Dip in EtOH
7. Dry on hot plate (50 °C)
8. Read under fluorescent microscope, time resolved fluorescence devices iii. Full Assay (b)

Figure 6:
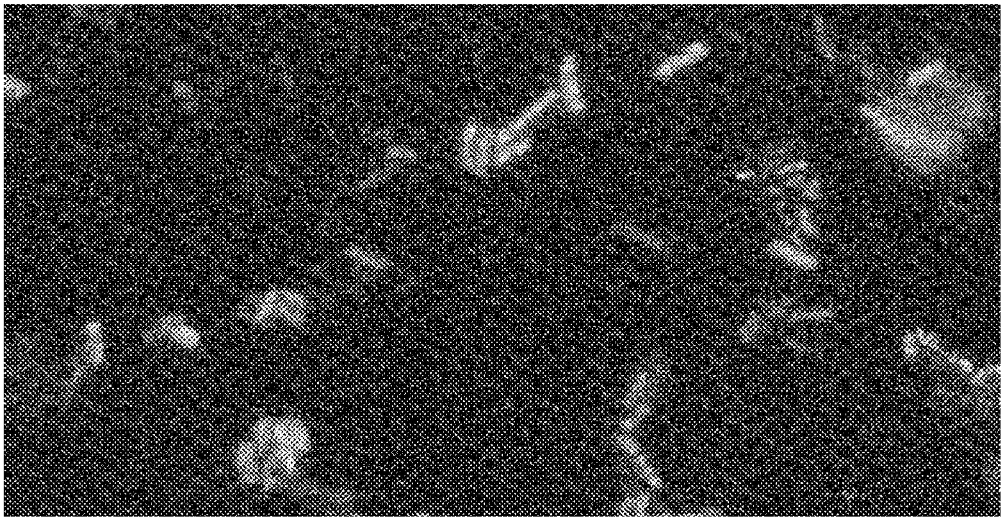
FIG. 6 and FIG. 7 shows three probes towards ribosomal RNA of *E. coli* working together under stringent ZIP requirement. The probes shown are SEQ ID NOs: 117 to 119, and the target sequence is SEQ ID NO: 120.
Figure 7:
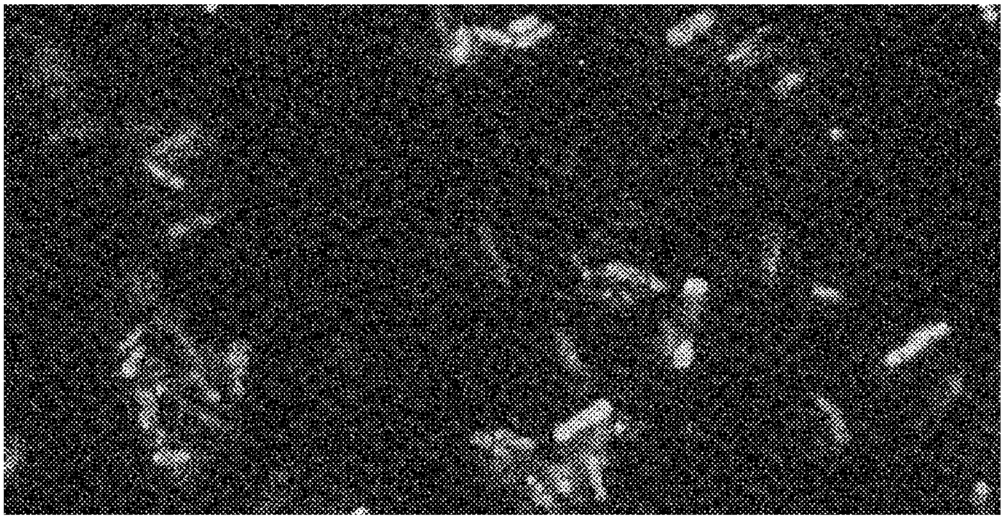

1. Apply 10 µl sample to each field on a microscopic slide and dry on a hot (50 °C) plate
2. For probes towards Grain negative organisms place 10 µl lysis mix and dry on the hot plate
3. Dip in EtOH bath for 5 min
4. Place on hot (50 °C) plate until dry
5. Add 10 µl hybridisation mix, or for sections sufficient to cover tissue
6. Close lid and hybridise for 10 min
7. Briefly dip in stop solution (hybridisation buffer without probes and formamide with 50% ethanol) at ambient temperature for 1 min.
8. Dip briefly in Ethanol (EtOH)
9. Dry on hot plate (50 °C)
10. Read under fluorescent microscope e) Results Three Zip probes (SEQ ID NO: 117, 118 and 119) identified to hybridise the DNA sequence: AGCGTGCCTTCTCCCGAGAT ATG TAG GTG AAG CGA CTTGCTCCTTCGACTGATTT CAGCTCCAC (SEQ ID NO: 120) specific for the *E. coli* ribosomal RNA were constructed according to the present invention. Samples were analysed according to the full assay (step diii(b)). Ribosomal rich regions within the cell show a bright green fluorescence under fluorescent microscope. FIG. 6 and FIG. 7 illustrate the ribosomal rich regions identified by the bright grey fluorescence, showing the three probes (SEQ ID NO: 117, 118 and 119) towards ribosomal RNA of *E. coli* working together under the stringent ZIP requirements.

TABLE 1

Sequences illustrated in FIGS. 1-5

| Sequence ID | Sequence name | Sequence |
|---|---|---|
| SEQ ID NO 1 | Probe Sequence 3 | cgtgaagtct tttggtgcat aaaatgtctg cttttatact aa |
| SEQ ID NO 2 | DNA Target Sequence 3 | tagtataaaa gcagacattt tatgcaccaa aaga |
| SEQ ID NO 3 | Probe Sequence 4 | ccgcatgtcc tgtgggtcct gaaacattgc agttccttca c |
| SEQ ID NO 4 | DNA Target Sequence 4 | gaactgcaat gtttcaggac ccacagga |
| SEQ ID NO 5 | Probe Sequence 5 | ggcgcctgca taactgtggt aactttctgg gtcgccatgc gg |
| SEQ ID NO 6 | DNA Target Sequence 5 | gcgacccaga aagttaccac agttatgca |
| SEQ ID NO 7 | Probe Sequence 6 | accgtcaaat attatatcat gtatagttgt ttgcagctct gggcgcc |
| SEQ ID NO 8 | DNA Target Sequence 6 | acagagctgca aacaactata catgatataa tatt |
| SEQ ID NO 9 | Probe Sequence 7 | tcccctacag taactgttgc ttgcagtaca cacattcttg acggt |
| SEQ ID NO 10 | DNA Target Sequence 7 | agaatgtgtg tactgcaagc aacagttact g |
| SEQ ID NO 11 | Probe Sequence 8 | ggcttgccga aaagcaaagt catatacctc acgtcgtagg gga |

TABLE 1-continued

Sequences illustrated in FIGS. 1-5

| Sequence ID | Sequence name | Sequence |
|---|---|---|
| SEQ ID NO 12 | DNA Target Sequence 8 | cgacgtgagg tatatgactt tgcttttcg |
| SEQ ID NO 13 | Probe Sequence 9 | atggattccc atctctatat actatgcata aatccgcaag cc |
| SEQ ID NO 14 | DNA Target Sequence 9 | ggatttatgc atagtatata gagatgggaa tccat |
| SEQ ID NO 15 | Probe 3g | tcttttggtg cataaaatgt ctgcttttat actaaaggtc atg |
| SEQ ID NO 16 | Probe 4d | tgaccttcct gtgggtcctg aaacattgca gttcaatcaa act |
| SEQ ID NO 17 | Probe 5e | agtttgattt gcataactgt ggtaactttc tgggtcgcac tctagt |
| SEQ ID NO 18 | Probe 6j | tctagagtaa tattatatca tgtatagttg tttgcagctc tgcatg |
| SEQ ID NO 19 | Probe 7f | catgcagtaa ctgttgcttg cagtacacac attcccgcg |
| SEQ ID NO 20 | Probe 8c | cgcggcgaaa agcaaagtca tatacctcac gtcgagacgg |
| SEQ ID NO 21 | Probe 9d | ccgtctatgg attcccatct ctatatacta tgcataaatc caagggg |
| SEQ ID NO 22 | Probe Sequence 10 | catttatcac atacagcat |
| SEQ ID NO 23 | DNA Target Sequence 10 | atgctgtatg tgataaatg |
| SEQ ID NO 24 | Probe Sequence c1b | acgcgcataa agtgtatgtc gtatacctaa gggtagagat a |
| SEQ ID NO 25 | DNA Target Sequence c1b | tatctctacc cttaggtata cgacatacac tatt |
| SEQ ID NO 26 | Probe Sequence c2b | ggtactgcat attgatacgt atttagggct tttcgtttca gtatatgcgc gt |
| SEQ ID NO 27 | DNA Target Sequence c2b | catatactga aacgaaaagc cctaaatacg tatcata |
| SEQ ID NO 28 | Probe Sequence c3b | gtgggtacag tgcagcgtca ttgacaacga acgtcatgtg cagtacc |
| SEQ ID NO 29 | DNA Target Sequence c3b | catgacgttc gttgtcaatg acgctgcact c |
| SEQ ID NO 30 | Probe Sequence c4b | ccagggagtg tgtaagatta taatatagta catatcaaca aacgtgtacc cac |
| SEQ ID NO 31 | DNA Target Sequence c4b | acgtttgttg atatgtacta tattataatc ttacaca |
| SEQ ID NO 32 | Probe Sequence c5b | ccacggtacc gagacacgta ttgacaccat tgaaagactc cctgg |
| SEQ ID NO 33 | DNA Target Sequence c5b | tctttcaatg gtgtcaatac gtgtctcg |
| SEQ ID NO 34 | Probe Sequence c6b | ggtagggccc agcgaggaca cccaggactt tgtaagctgt accgtgg |
| SEQ ID NO 35 | DNA Target Sequence c6b | acgttacaaa gtcctgggtg tcctcgctgg g |

TABLE 1-continued

| Sequences illustrated in FIGS. 1-5 | | |
|---|---|---|
| Sequence ID | Sequence name | Sequence |
| SEQ ID NO 36 | Probe Sequence c7b | caagagaaaa ccacgtattt tacagacgaa aaccctacc |
| SEQ ID NO 37 | DNA Target Sequence c7b | ttttcgtctg taaaatacgt ggttttctct tg |
| SEQ ID NO 38 | Half Target 3a | tagtataaaa gcag aca |
| SEQ ID NO 39 | Half Probe 3a' | tgtctgcttt ta tacta |
| SEQ ID NO 40 | Half Target 3b | ttttatgcac caaaaga |
| SEQ ID NO 41 | Half Probe 3b' | tcttttggtg cataaaa |
| SEQ ID NO 42 | Half Target 4a | gaactgcaat gtttca |
| SEQ ID NO 43 | Half Probe 4a' | tgaaacattg cagttc |
| SEQ ID NO 44 | Half Target 4b | ggacccacag ga |
| SEQ ID NO 45 | Half Probe 4b' | tcctgtgggt cc |
| SEQ ID NO 46 | Half Target 5a | gcgacccaga aa |
| SEQ ID NO 47 | Half Probe 5a' | tttctgggtc gc |
| SEQ ID NO 48 | Half Target 5b | gttaccacag ttatgc |
| SEQ ID NO 49 | Half Probe 5b' | gcataactgt ggtaac |
| SEQ ID NO 50 | Half Target 6a | acagagctgc aaac |
| SEQ ID NO 51 | Half Probe 6a' | gtttgcagct ctgt |
| SEQ ID NO 52 | Half Target 6b | aactatacat gatataatat t |
| SEQ ID NO 53 | Half Probe 6b' | aatattatat catgtatagtt |
| SEQ ID NO 54 | Half Target 7a | agaatgtgtg tactg |
| SEQ ID NO 55 | Half Probe 7a' | cagtacacac attc |
| SEQ ID NO 56 | Half Target 7b | caagcaacag ttactg |
| SEQ ID NO 57 | Half Probe 7b' | cagtaactgt tgcttg |
| SEQ ID NO 58 | Half Target 8a | cgacgtgagg tata |
| SEQ ID NO 59 | Half Probe 8a' | tatacctcac gtcg |
| SEQ ID NO 60 | Half Target 8b | tgactttgct tttcg |
| SEQ ID NO 61 | Half Probe 8b' | cgaaaagcaa agtca |
| SEQ ID NO 62 | Half Target 9a | ggatttatgc atagtata |
| SEQ ID NO 63 | Half Probe 9a' | tatactatgc ataaatcc |
| SEQ ID NO 64 | Half Target 9b | tagagatggg aatccat |
| SEQ ID NO 65 | Half Probe 9b' | atggattccc atctcta |
| SEQ ID NO 66 | Half Target 10a | atgctgtatg tgataaat |
| SEQ ID NO 67 | Resulting cDNA Target (3b + 4a) | ttttatgcac caaaagagaa ctgcaatgtt tca |
| SEQ ID NO 68 | Resulting cDNA Probe 7' | tgaaacattg cagttctctt ttggtgcata aaa |
| SEQ ID NO 69 | Resulting cDNA Target (4b + 5a) | ggacccacag gagcgaccca gaaa |
| SEQ ID NO 70 | Resulting cDNA Probe 6' | tttctgggtc gctcctgtgg gtcc |
| SEQ ID NO 71 | Resulting cDNA Target (5b + 6a) | gttaccacag ttatgcacag agctgcaaac |

TABLE 1-continued

Sequences illustrated in FIGS. 1-5

| Sequence ID | Sequence name | Sequence |
|---|---|---|
| SEQ ID NO 72 | Resulting cDNA Probe 5' | gtttgcagct ctgtgcataa ctgtggtaac |
| SEQ ID NO 73 | Resulting cDNA Target (6b + 7a) | aactatacat gatataatat tagaatgtgt gtactg |
| SEQ ID NO 74 | Resulting cDNA Probe 4' | cagtacacac attctaatat tatatcatgt atagtt |
| SEQ ID NO 75 | Resulting cDNA Target (7b + 8a) | caagcaacag ttactgcgac gtgaggtata |
| SEQ ID NO 76 | Resulting cDNA Probe 3' | tatacctcac gtcgcagtaa ctgttgcttg |
| SEQ ID NO 77 | Resulting cDNA Target (8b + 9a) | tgactttgct tttcgggatt tatgcatagt ata |
| SEQ ID NO 78 | Resulting cDNA Probe 2' | tatactatgc ataaatcccg aaaagcaaag tca |
| SEQ ID NO 79 | Resulting cDNA Target (9b + 10a) | tagagatggg aatccatatg ctgtatgtga taaat |
| SEQ ID NO 80 | Resulting cDNA Probe 1' | atttatcaca tacagcatat ggattcccat ctcta |
| SEQ ID NO 81 | Resulting cDNA Probes 7' with helping stems | accctgtgaa acattgcagt tctcttttgg tgcataaaa |
| SEQ ID NO 82 | Resulting cDNA Probes 6' with helping stems | tttgagggtt tctgggtcgc tcctgtgggt cccagggt |
| SEQ ID NO 83 | Resulting cDNA Probes 5' with helping stems | ggatgtgttt gcagctctgt gcataactgt ggtaacccctcaaa |
| SEQ ID NO 84 | Resulting cDNA Probes 4' with helping stems | cgtcacagta cacacattct aatattatat catgtatagt tacccat |
| SEQ ID NO 85 | Resulting cDNA Probes 3' with helping stems | cgcgtatacc tcacgtcgca gtaactgttg cttgtgacg |
| SEQ ID NO 86 | Resulting cDNA Probes 2' with helping stems | acgcgtatac tatgcataaa tcccgaaaag caaagtcacgcgggttc |
| SEQ ID NO 87 | Resulting cDNA Probes 1' with helping stems | atttatcaca tacagcatat ggattcccat ctctacgcgt |
| SEQ ID NO 88 | Staaur Probe Sequence | gcaagcttct cgtccgttcg c |
| SEQ ID NO 89 | Staaur Target Sequence | gcgaacggac gagaagcttg c |
| SEQ ID NO 90 | β-lactamase gene TEM-1 #1 target | ugcugcaacu uuauccgccu cc |
| SEQ ID NO 91 | β-lactamase gene TEM-1 #1 probe with stem | atgctgcatg gaggcggata aagttgcagc aatgcagcat |
| SEQ ID NO 92 | β-lactamase gene TEM-1 #2 target | auccagucua uuaauuguug ccggg |
| SEQ ID NO 93 | β-lactamase gene TEM-1 #2 probe with stem | atgctgcatc ccggcaacaa ttaatagact ggatatgcag cat |
| SEQ ID NO 94 | β-lactamase gene TEM-1 #3 target | aagcuagagu aaguaguucg ccag |
| SEQ ID NO 95 | β-lactamase gene TEM-1 #3 probe with stem | atgctgcatc tggcgaacta cttactctag cttatgcagc at |
| SEQ ID NO 96 | β-lactamase gene TEM-1 #4 target | uuaauaguuu gcgcaacguu guugcc |

TABLE 1-continued

Sequences illustrated in FIGS. 1-5

| Sequence ID | Sequence name | Sequence |
|---|---|---|
| SEQ ID NO 97 | β-lactamase gene TEM-1 #4 probe with stem | atgctgcatg gcaacaacgt tgcgcaaact attaaatgca gcat |
| SEQ ID NO 98 | β-lactamase gene TEM-1 #5 target | auugcugcag gcaucguggu g |
| SEQ ID NO 99 | β-lactamase gene TEM-1 #5 probe with stem | atgctgcatc accacgatgc ctgcagcaat atgcagcat |
| SEQ ID NO 100 | β-lactamase gene TEM-1 #6 target | ucacgcucgu cguuugguau gg |
| SEQ ID NO 101 | β-lactamase gene TEM-1 #6 probe with stem | atgctgcatc cataccaaac gacgagcgtg aatgcagcat |
| SEQ ID NO 102 | β-lactamase gene TEM-1 #7 target | cuucauucag cuccgguucc ca |
| SEQ ID NO 103 | β-lactamase gene TEM-1 #7 probe with stem | atgctgcatt gggaaccgga gctgaatgaa gaatgcagca t |
| SEQ ID NO 104 | β-lactamase gene TEM-1 #8 target | acgaucaagg cgaguuacau gauc |
| SEQ ID NO 105 | β-lactamase gene TEM-1 #8 probe with stem | atgctgcatg atcatgtaac tcgccttgat cgtatgcagc at |
| SEQ ID NO 106 | β-lactamase gene TEM-1 #9 target | ccccauguug ugcaaaaaag cgg |
| SEQ ID NO 107 | β-lactamase gene TEM-1 #9 probe with stem | atgctgcatc cgcttttttg cacaacatgg ggatgcagca t |
| SEQ ID NO 108 | β-lactamase gene TEM-1 #10 target | uuagcuccuu cgguccuccg |
| SEQ ID NO 109 | β-lactamase gene TEM-1 #10 probe with stem | atgctgcatc ggaggaccga aggagctaaa tgcagcat |
| SEQ ID NO 110 | Probe c1 | taaagtgtat gtcgtatacc taagggtaga gata |
| SEQ ID NO 111 | Probe c2 | acgtatttag ggcttttcgt ttcagtatat gg |
| SEQ ID NO 112 | Probe c3 | gtcattgaca acgaacgtca tgtgtgta |
| SEQ ID NO 113 | Probe c4 | tgtgtgtaag attataatat agtacatatc aacaaacgtc g |
| SEQ ID NO 114 | Probe c5 | agacacgtat tgacaccatt gaaagaccc |
| SEQ ID NO 115 | Probe c6 | agcgaggaca cccaggactt tgtaacaaga g |
| SEQ ID NO 116 | Probe c7 | aaaaccacgt attttacaga cgaaaatatg att |
| SEQ ID NO 117 | *E. coli* probe 5'-1 with stem: Atto-465 | actcagtatc tcgggagaag gcacgctgat actgagt |
| SEQ ID NO 118 | *E. coli* probe with stem: Atto-514 | actcagtacg caagtcgctt cacctacata tcgtactgag t |
| SEQ ID NO 119 | *E. coli* probe 3' + 1 with stem: Atto-465 | actcagtact ggagctgaaa tcagtcgaag gagtactgag t |
| SEQ ID NO 120 | Sequence specific for *E. coli* ribosomal RNA | AGCGTGCCTTCTCCCGAGAT ATG TAG GTG AAG CGA CTTGCTCCTTCGACTGATTT CAGCTCCAC |

The invention claimed is:

1. A multiplicity of hairpin loop forming nucleic acid probes capable of concatenating in situ to form a concatenated probe complementary to a target nucleic acid sequence, each nucleic acid probe of the multiplicity comprising:

a nucleic acid sequence complementary to the target nucleic acid sequence;

a 5' flanking sequence comprising a first detection moiety; and a 3' flanking sequence comprising a second detection moiety, wherein the 5' flanking sequence and the 3' flanking sequence of a single nucleic acid probe are at least partially complementary to each other;

wherein the multiplicity of nucleic acid probes comprises at least two populations of probe; a first population characterized in that the first detection moiety and the second detection moiety on a single nucleic acid probe are the same and are each of type A; and second population characterized in that the first detection moiety and the second detection moiety on a single nucleic acid probe are the same and are each of type B;

wherein said multiplicity of nucleic acid probes are capable of concatenating in situ to form a concatenated probe complementary to the target sequence, in which probes of the first population alternate with probes of the second population, such that the 5' flanking sequence of a first nucleic acid probe of a first population interlinks with at least part of the 3' flanking sequence of a neighboring nucleic acid probe of the second population to form a stem structure such that the first detection moiety of the first nucleic acid probe and the second detection moiety of the neighboring nucleic acid probe of the stem structure interact to generate a signal.

2. The multiplicity of nucleic acid probes of claim 1, wherein the 5' and/or 3' flanking-sequences do not hybridise with the target nucleic acid sequence.

3. The multiplicity of nucleic acid probes of claim 1, wherein the stem structure has a significantly less negative ΔG and a $T_m$-value below the hybridization temperature with respect to the hybridization target.

4. The multiplicity of nucleic acid probes of claim 1, wherein the probe nucleic acid sequence complementary to the target nucleic acid sequence comprises ribonucleotides, ribonucleotide analogues, deoxyribonucleotides, deoxyribonucleotide analogues, or a combination thereof.

5. The multiplicity of nucleic acid probes of claim 1, wherein the probe nucleic acid sequence complementary to the target nucleic acid sequence is DNA and the 5' and 3' flanking sequences of the probe comprise DNA-analogues.

6. The multiplicity of nucleic acid probes of claim 1, wherein the target nucleic acid sequence is DNA or RNA.

7. The multiplicity of nucleic acid probes of claim 1, wherein said first detection moiety of the first nucleic acid probe is an energizer (type-a probe) and said second detection moiety of the neighboring nucleic acid probe is a molecule capable of energy resonance transfer (type-b probe); or wherein said first detection moiety of the first nucleic acid probe is a molecule capable of energy resonance transfer (type-b probe) and said second detection moiety of the neighboring nucleic acid probe is an energizer (type-a probe).

* * * * *